United States Patent
Mukai et al.

(10) Patent No.: US 9,943,647 B2
(45) Date of Patent: Apr. 17, 2018

(54) PHARMACEUTICAL INJECTION DEVICE, METHOD FOR CONTROLLING PHARMACEUTICAL INJECTION DEVICE, AND RECORDING MEDIUM

(71) Applicant: Panasonic Healthcare Co., Ltd., Ehime (JP)

(72) Inventors: Yasutaka Mukai, Ehime (JP); Seiji Kikuchi, Ehime (JP); Tsuguhiro Kondoh, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 698 days.

(21) Appl. No.: 14/349,913

(22) PCT Filed: Oct. 5, 2012

(86) PCT No.: PCT/JP2012/006452
§ 371 (c)(1),
(2) Date: Apr. 4, 2014

(87) PCT Pub. No.: WO2013/051293
PCT Pub. Date: Apr. 11, 2013

(65) Prior Publication Data
US 2014/0243787 A1 Aug. 28, 2014

(30) Foreign Application Priority Data
Oct. 7, 2011 (JP) .................................. 2011-222483

(51) Int. Cl.
*A61M 5/20* (2006.01)
*A61M 5/315* (2006.01)

(52) U.S. Cl.
CPC .......... *A61M 5/20* (2013.01); *A61M 5/31546* (2013.01); *A61M 5/31568* (2013.01);
(Continued)

(58) Field of Classification Search
CPC .... A61M 2005/14208; A61M 5/31546; A61M 5/168; A61M 5/1684; A61M 5/172; A61M 2205/52; G06F 19/3468
See application file for complete search history.

(56) References Cited

U.S. PATENT DOCUMENTS

| 4,950,246 A | 8/1990 | Muller |
| 2005/0021006 A1* | 1/2005 | Tonnies ................ A61M 5/172 604/890.1 |

(Continued)

FOREIGN PATENT DOCUMENTS

| CN | 88102557 A | 12/1988 |
| CN | 1984690 A | 6/2007 |

(Continued)

OTHER PUBLICATIONS

Chinese Office Action for Application No. 201280046289.X dated May 27, 2015.
(Continued)

*Primary Examiner* — Andrew Gilbert
*Assistant Examiner* — William Frehe
(74) *Attorney, Agent, or Firm* — Pearne & Gordon LLP

(57) ABSTRACT

A pharmaceutical injection device comprises a main body case (2); a pharmaceutical syringe mounting component (3) that is provided inside the main body case (2) and onto which a pharmaceutical syringe (4) is mounted; a piston (5) provided movably with respect to the pharmaceutical syringe (4) mounted onto the pharmaceutical syringe mounting component (3); a drive mechanism (6) for driving the piston (5); a memory (46) that stores a preset pharmaceutical injection schedule; and a controller (7) that resets a current pharmaceutical dose by comparing a planned cumulative pharmaceutical dose, which is a planned cumulative amount of pharmaceutical injected up to the last time on the basis of the pharmaceutical injection schedule stored in the memory, (Continued)

and an actual cumulative pharmaceutical dose, which is a cumulative amount of pharmaceutical actually injected up to the last time.

11 Claims, 50 Drawing Sheets

(52) U.S. Cl.
CPC ............... *A61M 2005/2006* (2013.01); *A61M 2205/3379* (2013.01); *A61M 2205/50* (2013.01); *A61M 2205/502* (2013.01); *A61M 2205/52* (2013.01)

(56) References Cited

U.S. PATENT DOCUMENTS

| | | | |
|---|---|---|---|
| 2009/0030366 A1* | 1/2009 | Hochman | A61M 5/20 604/67 |
| 2009/0131861 A1* | 5/2009 | Braig | A61B 5/1427 604/66 |
| 2009/0131862 A1 | 5/2009 | Buck et al. | |
| 2010/0249561 A1 | 9/2010 | Patek et al. | |
| 2010/0286612 A1* | 11/2010 | Cirillo | A61M 5/31525 604/111 |
| 2010/0292634 A1* | 11/2010 | Kircher, Jr. | A61B 5/14532 604/66 |
| 2011/0004165 A1* | 1/2011 | Iio | A61M 5/20 604/197 |
| 2011/0257602 A1 | 10/2011 | Watanabe et al. | |
| 2013/0336881 A1 | 12/2013 | Buck et al. | |
| 2015/0025296 A1 | 1/2015 | Buck et al. | |

FOREIGN PATENT DOCUMENTS

| | | |
|---|---|---|
| CN | 101868267 A | 10/2010 |
| EP | 0 293 958 A1 | 12/1988 |
| EP | 0 777 123 A2 | 6/1997 |
| JP | 2000-042103 A | 2/2000 |
| JP | 3081305 U | 8/2001 |
| JP | 3081305 U | 11/2001 |
| JP | 2002-336331 A | 11/2002 |
| JP | 2010-531678 A | 9/2010 |
| JP | 2011-501681 A | 1/2011 |
| WO | 2009/067492 A1 | 5/2009 |
| WO | 2009067492 A1 | 5/2009 |
| WO | 2009/125582 A1 | 10/2009 |
| WO | 2010073452 A1 | 7/2010 |
| WO | 2011/117212 A1 | 9/2011 |

OTHER PUBLICATIONS

International Search Report for Application No. PCT/JP2012/006452 dated Dec. 18, 2012.
Chinese Office Action dated Jan. 4, 2016 for Chinese Patent Application No. 201280046289.X.
Extended European Search Report for Application No. 12838934.3 dated May 6, 2015.
Japanese Office Action issued in Japanese Patent Application No. 2016-086429 dated Jan. 31, 2017.

\* cited by examiner

Fig. 16 (a) — 10:15, April 9, 2011 — 35

Fig. 16 (b) — No injection scheduled today. — 35

Fig. 16 (c) — Ready for injection. Dose this time: 1.00 mg — 35

Fig. 16 (d) — Ready for injection. Skipped injection. Dose short by: 1.00 mg Extra 0.30 mg will be injected. Current dose: 1.30 mg — 35

Fig. 16 (e) — Cumulative dose is too low. Please consult a physician. — 35

Fig. 16 (f) — Ready for injection. Dose still short. Dose short by: 1.70 mg Extra 0.30 mg will be injected. Current dose: 1.30 mg — 35

Fig. 16 (g) — Excessive injection. Please consult a physician. — 35

Fig. 16 (h) — Ready for injection Excessive dosage. Dose too high by: 1.00 mg 0.30 mg less will be injected. Current dose: 0.70 mg — 35

Fig. 16 (i) — Ready for injection. Dose still too high. Dose too high by: 0.70 mg 0.30 mg less will be injected. Current dose: 0.70 mg — 35

April 2011

| | Sun | Mon | Tue | Wed | Thu | Fri | Sat |
|---|---|---|---|---|---|---|---|
| | | | | | | 1 | 2 |
| planned | | | | | | 1.00mg | |
| result | | | | | | | |
| | 3 | 4 | 5 | 6 | 7 | 8 | 9 |
| planned | 1.00mg | 1.00mg | 1.00mg | 1.00mg | 1.00mg | 1.00mg | |
| result | | | | | | | |
| | 10 | 11 | 12 | 13 | 14 | 15 | 16 |
| planned | 1.00mg | 1.00mg | 1.00mg | 1.00mg | 1.00mg | 1.00mg | |
| result | | | | | | | |
| | 17 | 18 | 19 | 20 | 21 | 22 | 23 |
| planned | 1.00mg | 1.00mg | 1.00mg | 1.00mg | 1.00mg | 1.00mg | |
| result | | | | | | | |
| | 24 | 25 | 26 | 27 | 28 | 29 | 30 |
| planned | 1.00mg | 1.00mg | 1.00mg | 1.00mg | 1.00mg | 1.00mg | |
| result | | | | | | | |

Note: Example of when the daily planned dose is 1.00 mg.
The date at this point is March 31, 2011, and no injection has been performed.

FIG. 23

April 2011

| | Sun | Mon | Tue | Wed | Thu | Fri | Sat |
|---|---|---|---|---|---|---|---|
| | | | | | | 1 | 2 |
| planned | | | | | | 1.00mg | |
| result | | | | | | 1.00mg | |
| | 3 | 4 | 5 | 6 | 7 | 8 | 9 |
| planned | 1.00mg | 1.00mg | 1.00mg | 1.00mg | 1.00mg | 1.00mg | |
| result | 1.00mg | 1.00mg | 1.00mg | 1.00mg | 1.00mg | 0mg | |
| | 10 | 11 | 12 | 13 | 14 | 15 | 16 |
| planned | 1.00mg | 1.00mg | 1.00mg | 1.00mg | 1.00mg | 1.00mg | |
| result | | | | | | | |
| | 17 | 18 | 19 | 20 | 21 | 22 | 23 |
| planned | 1.00mg | 1.00mg | 1.00mg | 1.00mg | 1.00mg | 1.00mg | |
| result | | | | | | | |
| | 24 | 25 | 26 | 27 | 28 | 29 | 30 |
| planned | 1.00mg | 1.00mg | 1.00mg | 1.00mg | 1.00mg | 1.00mg | |
| result | | | | | | | |

Note: Injection was skipped on April 8, 2011.
The current date is April 10, 2011.
This is the state before correction.

FIG. 24

April 2011

| | Sun | Mon | Tue | Wed | Thu | Fri | Sat |
|---|---|---|---|---|---|---|---|
| | | | | | | 1 | 2 |
| planned | | | | | | 1.00mg | |
| result | | | | | | 1.00mg | |
| | 3 | 4 | 5 | 6 | 7 | 8 | 9 |
| planned | 1.00mg | 1.00mg | 1.00mg | 1.00mg | | 1.00mg | |
| result | 1.00mg | 1.00mg | 1.00mg | 1.00mg | 1.00mg | 0mg | |
| | 10 | 11 | 12 | 13 | 14 | 15 | 16 |
| planned | 1.30mg | 1.30mg | 1.30mg | 1.10mg | 1.00mg | 1.00mg | |
| result | | | | | | | |
| | 17 | 18 | 19 | 20 | 21 | 22 | 23 |
| planned | 1.00mg | 1.00mg | 1.00mg | 1.00mg | 1.00mg | 1.00mg | |
| result | | | | | | | |
| | 24 | 25 | 26 | 27 | 28 | 29 | 30 |
| planned | 1.00mg | 1.00mg | 1.00mg | 1.00mg | 1.00mg | 1.00mg | |
| result | | | | | | | |

Note: Injection was skipped on April 8, 2011.
The current date is April 10, 2011.
This is the state after correction.

FIG. 25

| April 2011 | Sun | Mon | Tue | Wed | Thu | Fri | Sat |
|---|---|---|---|---|---|---|---|
| | | | | | | 1 | 2 |
| planned | | | | | | 1.00mg | |
| result | | | | | | | |
| | 3 | 4 | 5 | 6 | 7 | 8 | 9 |
| planned | | 1.00mg | 1.00mg | 1.00mg | 1.00mg | 1.00mg | |
| result | | | | | | | |
| | 10 | 11 | 12 | 13 | 14 | 15 | 16 |
| planned | | 1.00mg | 1.00mg | 1.00mg | 1.00mg | 1.00mg | |
| result | | | | | | | |
| | 17 | 18 | 19 | 20 | 21 | 22 | 23 |
| planned | | 1.00mg | 1.00mg | 1.00mg | 1.00mg | 1.00mg | |
| result | | | | | | | |
| | 24 | 25 | 26 | 27 | 28 | 29 | 30 |
| planned | | 1.00mg | 1.00mg | 1.00mg | 1.00mg | 1.00mg | |
| result | | | | | | | |

Note: Example of when the daily planned dose is 1.00 mg.
The date at this point is March 31, 2011, and no injection has been performed.

April 2011

| | Sun | Mon | Tue | Wed | Thu | Fri | Sat |
|---|---|---|---|---|---|---|---|
| planned | | | | | | 1 1.00mg | 2 |
| result | | | | | | 1.00mg | |
| planned | 3 | 4 1.00mg | 5 1.00mg | 6 1.00mg | 7 1.00mg | 8 1.00mg | 9 |
| result | | 1.00mg | 1.00mg | 1.00mg | 1.00mg | 0mg | |
| planned | 10 | 11 1.00mg | 12 1.00mg | 13 1.00mg | 14 1.00mg | 15 1.00mg | 16 |
| result | | | | | | | |
| planned | 17 | 18 1.00mg | 19 1.00mg | 20 1.00mg | 21 1.00mg | 22 1.00mg | 23 |
| result | | | | | | | |
| planned | 24 | 25 1.00mg | 26 1.00mg | 27 1.00mg | 28 1.00mg | 29 1.00mg | 30 |
| result | | 1.00mg | 1.00mg | 1.00mg | 1.00mg | 1.00mg | |

Note: Example of when the daily planned dose is 1.00 mg.
The date at this point is April 11, 2011.
This is the state before correction.

April 2011

| | Sun | Mon | Tue | Wed | Thu | Fri | Sat |
|---|---|---|---|---|---|---|---|
| | | | | | | 1 | 2 |
| planned | | | | | | 1.00mg | |
| result | | | | | | 1.00mg | |
| | 3 | 4 | 5 | 6 | 7 | 8 | 9 |
| planned | | 1.00mg | 1.00mg | 1.00mg | 1.00mg | 1.00mg | |
| result | | 1.00mg | 1.00mg | 1.00mg | 1.00mg | 0mg | |
| | 10 | 11 | 12 | 13 | 14 | 15 | 16 |
| planned | | 1.30mg | 1.30mg | 1.30mg | 1.10mg | 1.00mg | |
| result | | | | | | | |
| | 17 | 18 | 19 | 20 | 21 | 22 | 23 |
| planned | | 1.00mg | 1.00mg | 1.00mg | 1.00mg | 1.00mg | |
| result | | | | | | | |
| | 24 | 25 | 26 | 27 | 28 | 29 | 30 |
| planned | | 1.00mg | 1.00mg | 1.00mg | 1.00mg | 1.00mg | |
| result | | | | | | | |

Note: Example of when the daily planned dose is 1.00 mg.
The date at this point is April 11, 2011.
This is the state after correction.

FIG. 28

April 2011

| | Sun | Mon | Tue | Wed | Thu | Fri | Sat |
|---|---|---|---|---|---|---|---|
| | | | | | | 1 | 2 |
| planned | | | | | | 1.00mg | |
| result | | | | | | 1.00mg | |
| | 3 | 4 | 5 | 6 | 7 | 8 | 9 |
| planned | | 1.00mg | 1.00mg | 1.00mg | 1.00mg | 1.00mg | |
| result | | 1.00mg | 1.00mg | 1.00mg | 1.00mg | 1.00mg | |
| | 10 | 11 | 12 | 13 | 14 | 15 | 16 |
| planned | | 1.00mg | | 1.00mg | 1.00mg | 1.00mg | 1.00mg |
| result | | | | | | | |
| | 17 | 18 | 19 | 20 | 21 | 22 | 23 |
| planned | | 1.00mg | 1.00mg | 1.00mg | 1.00mg | 1.00mg | |
| result | | | | | | | |
| | 24 | 25 | 26 | 27 | 28 | 29 | 30 |
| planned | | 1.00mg | 1.00mg | 1.00mg | 1.00mg | 1.00mg | |
| result | | | | | | | |

Note: Example of when the daily planned dose is 1.00 mg.
The date at this point is April 11, 2011.
This is the state before correction.

FIG. 29

April 2011

| | Sun | Mon | Tue | Wed | Thu | Fri | Sat |
|---|---|---|---|---|---|---|---|
| | | | | | | 1 | 2 |
| planned | | | | | | 1.00mg | |
| result | | | | | | 1.00mg | |
| | 3 | 4 | 5 | 6 | 7 | 8 | 9 |
| planned | | 1.00mg | 1.00mg | 1.00mg | 1.00mg | 1.00mg | |
| result | | 1.00mg | 1.00mg | 1.00mg | 1.00mg | 1.00mg | 1.00mg |
| | 10 | 11 | 12 | 13 | 14 | 15 | 16 |
| planned | | 0.70mg | 0.70mg | 0.70mg | 0.90mg | 1.00mg | |
| result | | | | | | | |
| | 17 | 18 | 19 | 20 | 21 | 22 | 23 |
| planned | | 1.00mg | 1.00mg | 1.00mg | 1.00mg | 1.00mg | |
| result | | | | | | | |
| | 24 | 25 | 26 | 27 | 28 | 29 | 30 |
| planned | | 1.00mg | 1.00mg | 1.00mg | 1.00mg | 1.00mg | |
| result | | | | | | | |

Note: Example of when the daily planned dose is 1.00 mg.
The date at this point is April 11, 2011.
This is the state after correction.

Ready for injection.
All of remaining pharmaceutical will be injected to use it up.
Current dose: 0.50 mg

Ready for injection.
Injection has been adjusted. Remaining adjustment dose: 0.00 mg
0.20 mg less will be injected. Current dose: 0.80 mg

Ready for injection.
Injection has been adjusted. Remaining adjustment dose: −0.20 mg
Extra 0.30 mg will be injected. Current dose: 1.30 mg

35

April 2011

| | Sun | Mon | Tue | Wed | Thu | Fri | Sat |
|---|---|---|---|---|---|---|---|
| planned | | | | | | 1 | 2 |
| result | | | | | | 1.00mg | / |
| planned | 3 | 4 | 5 | 6 | 7 | 8 | 9 |
| result | 1.00mg | 1.00mg | 1.00mg | 1.00mg | 1.00mg | 1.00mg | / |
| planned | 10 | 11 | 12 | 13 | 14 | 15 | 16 |
| result | 1.00mg | 1.00mg | 1.00mg | 1.00mg | 1.00mg | 1.00mg | / |
| planned | 17 | 18 | 19 | 20 | 21 | 22 | 23 |
| result | 1.00mg | 1.00mg | 1.00mg | 1.00mg | 1.00mg | 1.00mg | / |
| planned | 24 | 25 | 26 | 27 | 28 | 29 | 30 |
| result | 1.00mg | 1.00mg | 1.00mg | 1.00mg | 1.00mg | 1.00mg | / |

Note: Example of when the daily planned dose is 1.00 mg.
The date at this point is March 31, 2011, and no injection has been performed.

FIG. 34

April 2011

|  | Sun | Mon | Tue | Wed | Thu | Fri | Sat |
|---|---|---|---|---|---|---|---|
|  |  |  |  |  |  | 1 | 2 |
| planned |  |  |  |  |  | 1.00mg |  |
| result |  |  |  |  |  | 1.00mg |  |
|  | 3 | 4 | 5 | 6 | 7 | 8 | 9 |
| planned | 1.00mg | 1.00mg | 1.00mg | 1.00mg | 1.00mg | 1.00mg |  |
| result | 1.00mg | 1.00mg | 1.00mg | 1.00mg | 1.00mg | 0.50mg |  |
|  | 10 | 11 | 12 | 13 | 14 | 15 | 16 |
| planned | 1.00mg | 1.00mg | 1.00mg | 1.00mg | 1.00mg | 1.00mg |  |
| result |  |  |  |  |  |  |  |
|  | 17 | 18 | 19 | 20 | 21 | 22 | 23 |
| planned | 1.00mg | 1.00mg | 1.00mg | 1.00mg | 1.00mg | 1.00mg |  |
| result |  |  |  |  |  |  |  |
|  | 24 | 25 | 26 | 27 | 28 | 29 | 30 |
| planned | 1.00mg | 1.00mg | 1.00mg | 1.00mg | 1.00mg | 1.00mg |  |
| result |  |  |  |  |  |  |  |

Note: Using a formulation with a volume of 6.5 mg, injection was begun on April 1, 2011. Smaller injection was performed by balance method on April 8, 2011 to use up pharmaceutical. The current date is April 10, 2011. This is the state before correction.

FIG. 35

April 2011

| | Sun | Mon | Tue | Wed | Thu | Fri | Sat |
|---|---|---|---|---|---|---|---|
| planned | | | | | | 1 | 2 |
| | | | | | | 1.00mg | |
| result | | | | | | 1.00mg | |
| planned | 3 | 4 | 5 | 6 | 7 | 8 | 9 |
| | 1.00mg | 1.00mg | 1.00mg | 1.00mg | 1.00mg | 1.00mg | |
| result | 1.00mg | 1.00mg | 1.00mg | 1.00mg | 1.00mg | 0.50mg | |
| planned | 10 | 11 | 12 | 13 | 14 | 15 | 16 |
| | 1.30mg | 1.20mg | 1.00mg | 1.00mg | 1.00mg | 1.00mg | |
| result | | | | | | | |
| planned | 17 | 18 | 19 | 20 | 21 | 22 | 23 |
| | 1.00mg | 1.00mg | 1.00mg | 1.00mg | 1.00mg | 1.00mg | |
| result | | | | | | | |
| planned | 24 | 25 | 26 | 27 | 28 | 29 | 30 |
| | 1.00mg | 1.00mg | 1.00mg | 1.00mg | 1.00mg | 1.00mg | |
| result | | | | | | | |

Note: Smaller injection was performed by balance method on April 8, 2011 to use up pharmaceutical. The current date is April 10, 2011. This is the state after correction.

FIG. 36

April 2011

| | Sun | Mon | Tue | Wed | Thu | Fri | Sat |
|---|---|---|---|---|---|---|---|
| | | | | | | 1 | 2 |
| planned | | | | | | 1.00mg | |
| result | | | | | | 1.00mg | |
| | 3 | 4 | 5 | 6 | 7 | 8 | 9 |
| planned | 1.00mg | 1.00mg | 1.00mg | 1.00mg | 1.00mg | 1.00mg | |
| result | 1.00mg | 1.00mg | 1.00mg | 1.00mg | 1.00mg | 1.20mg | |
| | 10 | 11 | 12 | 13 | 14 | 15 | 16 |
| planned | 1.00mg | 1.00mg | 1.00mg | 1.00mg | 1.00mg | 1.00mg | |
| result | | | | | | | |
| | 17 | 18 | 19 | 20 | 21 | 22 | 23 |
| planned | 1.00mg | 1.00mg | 1.00mg | 1.00mg | 1.00mg | 1.00mg | |
| result | | | | | | | |
| | 24 | 25 | 26 | 27 | 28 | 29 | 30 |
| planned | 1.00mg | 1.00mg | 1.00mg | 1.00mg | 1.00mg | 1.00mg | |
| result | | | | | | | |

Note: Larger injection was performed by balance method on April 8, 2011 to use up pharmaceutical. The current date is April 10, 2011. This is the state before correction.

FIG. 37

April 2011

| | Sun | Mon | Tue | Wed | Thu | Fri | Sat |
|---|---|---|---|---|---|---|---|
| | | | | | | 1 | 2 |
| planned | | | | | | 1.00mg | / |
| result | | | | | | 1.00mg | / |
| | 3 | 4 | 5 | 6 | 7 | 8 | 9 |
| planned | 1.00mg | 1.00mg | 1.00mg | 1.00mg | | | / |
| result | 1.00mg | 1.00mg | 1.00mg | 1.00mg | 1.00mg | 1.20mg | / |
| | 10 | 11 | 12 | 13 | 14 | 15 | 16 |
| planned | 0.80mg | 1.00mg | 1.00mg | 1.00mg | 1.00mg | 1.00mg | / |
| result | | | | | | | |
| | 17 | 18 | 19 | 20 | 21 | 22 | 23 |
| planned | 1.00mg | 1.00mg | 1.00mg | 1.00mg | 1.00mg | 1.00mg | / |
| result | | | | | | | |
| | 24 | 25 | 26 | 27 | 28 | 29 | 30 |
| planned | 1.00mg | 1.00mg | 1.00mg | 1.00mg | 1.00mg | 1.00mg | / |
| result | | | | | | | |

Note: Larger injection was performed by balance method on April 8, 2011 to use up pharmaceutical. The current date is April 10, 2011. This is the state after correction.

FIG. 38

April 2011

| | Sun | Mon | Tue | Wed | Thu | Fri | Sat |
|---|---|---|---|---|---|---|---|
| | | | | | | 1 | 2 |
| planned | | | | | | 1.00mg | |
| result | | | | | | 1.00mg | |
| | 3 | 4 | 5 | 6 | 7 | 8 | 9 |
| planned | 1.00mg | 1.00mg | 1.00mg | 1.00mg | 1.00mg | 1.00mg | |
| result | 1.00mg | 1.00mg | 1.00mg | 1.00mg | 1.00mg | 0.50mg | |
| | 10 | 11 | 12 | 13 | 14 | 15 | 16 |
| planned | 1.30mg | 1.20mg | 1.00mg | 1.00mg | 1.00mg | 1.00mg | |
| result | 1.30mg | 0.00mg | | | | | |
| | 17 | 18 | 19 | 20 | 21 | 22 | 23 |
| planned | 1.00mg | 1.00mg | 1.00mg | 1.00mg | 1.00mg | 1.00mg | |
| result | | | | | | | |
| | 24 | 25 | 26 | 27 | 28 | 29 | 30 |
| planned | 1.00mg | 1.00mg | 1.00mg | 1.00mg | 1.00mg | 1.00mg | |
| result | | | | | | | |

Note: Smaller injection was performed by balance method on April 8, 2011 to use up pharmaceutical. Injection was skipped on April 11. The current date is April 12, 2011. This is the state before correction.

FIG. 39

April 2011

| | Sun | Mon | Tue | Wed | Thu | Fri | Sat |
|---|---|---|---|---|---|---|---|
| | | | | | | 1 | 2 |
| planned | | | | | | 1.00mg | |
| result | | | | | | 1.00mg | |
| | 3 | 4 | 5 | 6 | 7 | 8 | 9 |
| planned | 1.00mg | 1.00mg | 1.00mg | 1.00mg | 1.00mg | 1.00mg | |
| result | 1.00mg | 1.00mg | 1.00mg | 1.00mg | 1.00mg | 0.50mg | |
| | 10 | 11 | 12 | 13 | 14 | 15 | 16 |
| planned | 1.30mg | 1.20mg | 1.30mg | 1.30mg | 1.30mg | 1.30mg | |
| result | 1.30mg | 0.00mg | | | | | |
| | 17 | 18 | 19 | 20 | 21 | 22 | 23 |
| planned | 1.00mg | 1.00mg | 1.00mg | 1.00mg | 1.00mg | 1.00mg | |
| result | | | | | | | |
| | 24 | 25 | 26 | 27 | 28 | 29 | 30 |
| planned | 1.00mg | 1.00mg | 1.00mg | 1.00mg | 1.00mg | 1.00mg | |
| result | | | | | | | |

Note: Smaller injection was performed by balance method on April 8, 2011 to use up pharmaceutical. Injection was skipped on April 11. The current date is April 12, 2011. This is the state after correction.

April 2011

| | Sun | Mon | Tue | Wed | Thu | Fri | Sat |
|---|---|---|---|---|---|---|---|
| | | | | | | 1 | 2 |
| planned | | | | | | 1.00mg | |
| result | | | | | | 1.00mg | |
| | 3 | 4 | 5 | 6 | 7 | 8 | 9 |
| planned | 1.00mg | 1.00mg | 1.00mg | 1.00mg | 1.00mg | 1.00mg | |
| result | 1.00mg | 1.00mg | 1.00mg | 1.00mg | 1.00mg | 0mg | |
| | 10 | 11 | 12 | 13 | 14 | 15 | 16 |
| planned | 1.30mg | 1.00mg | 1.00mg | 1.00mg | 1.00mg | 1.00mg | |
| result | | | | | | | |
| | 17 | 18 | 19 | 20 | 21 | 22 | 23 |
| planned | 1.00mg | 1.00mg | 1.00mg | 1.00mg | 1.00mg | 1.00mg | |
| result | | | | | | | |
| | 24 | 25 | 26 | 27 | 28 | 29 | 30 |
| planned | 1.00mg | 1.00mg | 1.00mg | 1.00mg | 1.00mg | 1.00mg | |
| result | | | | | | | |

Note: Injection was skipped on April 8, 2011.
The current date is April 10, 2011.
This is the state after correction.

April 2011

| | Sun | Mon | Tue | Wed | Thu | Fri | Sat |
|---|---|---|---|---|---|---|---|
| planned | | | | | | 1 1.00mg | 2 |
| result | | | | | | 1.00mg | |
| planned | 3 1.00mg | 4 1.00mg | 5 1.00mg | 6 1.00mg | 7 1.00mg | 8 1.00mg | 9 |
| result | 1.00mg | 1.00mg | 1.00mg | 1.00mg | 1.00mg | 0mg | |
| planned | 10 1.30mg | 11 | 12 1.00mg | 13 1.00mg | 14 1.00mg | 15 1.00mg | 16 |
| result | 1.30mg | 1.30mg | | | | | |
| planned | 17 1.00mg | 18 1.00mg | 19 1.00mg | 20 1.00mg | 21 1.00mg | 22 1.00mg | 23 |
| result | | | | | | | |
| planned | 24 1.00mg | 25 1.00mg | 26 1.00mg | 27 1.00mg | 28 1.00mg | 29 1.00mg | 30 |
| result | 1.00mg | 1.00mg | 1.00mg | 1.00mg | 1.00mg | 1.00mg | |

Note: Injection was skipped on April 8, 2011.
The current date is April 11, 2011.
This is the state after correction.

FIG. 44

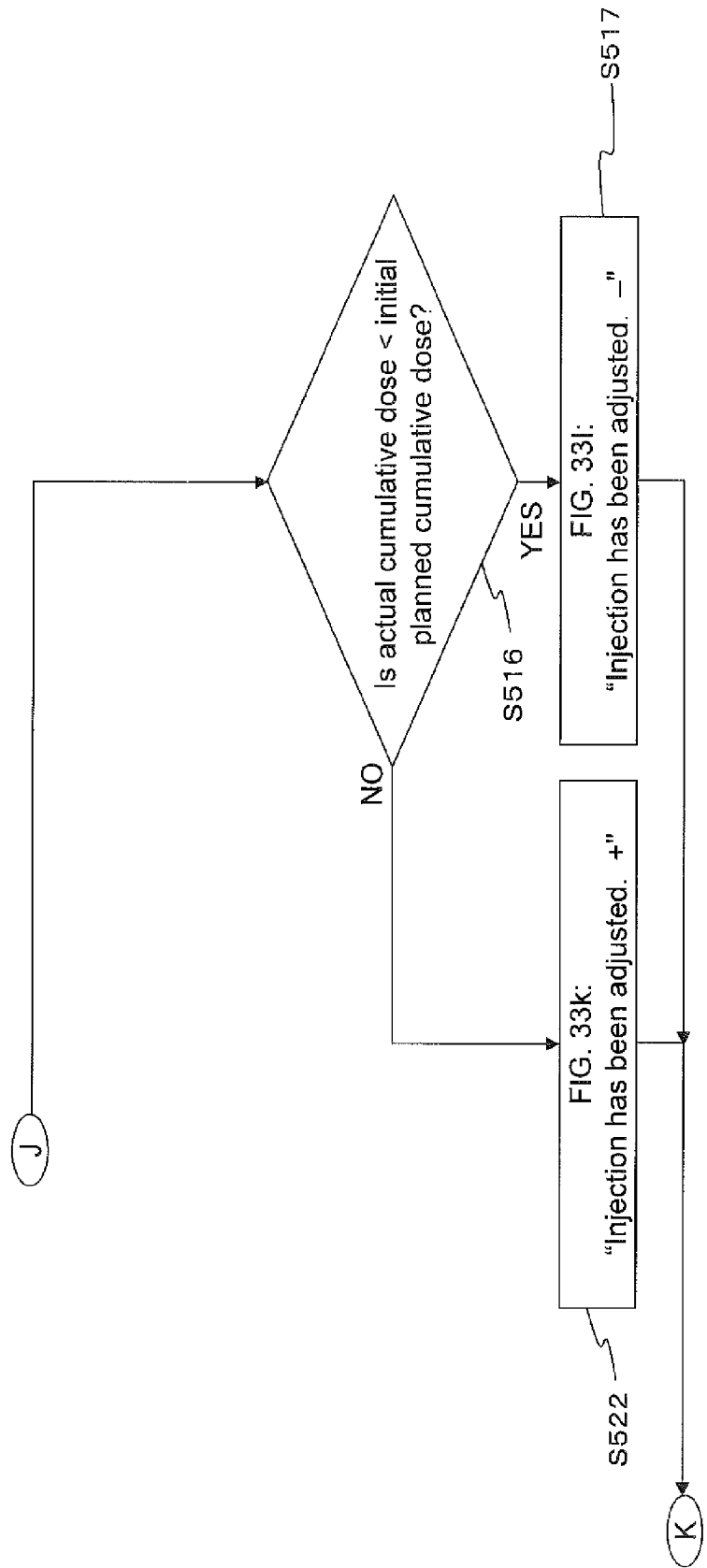

PHARMACEUTICAL INJECTION DEVICE, METHOD FOR CONTROLLING PHARMACEUTICAL INJECTION DEVICE, AND RECORDING MEDIUM

TECHNICAL FIELD

The present invention relates to a pharmaceutical injection device, and to a method for controlling a pharmaceutical injection device.

BACKGROUND ART

A conventional pharmaceutical injection device had a configuration comprising a main body case having an injection needle insertion and retraction opening, a pharmaceutical syringe mounting component provided inside this main body case, a piston provided movably with respect to a pharmaceutical syringe that is mounted onto this pharmaceutical syringe mounting component, a drive mechanism that drives this piston, a controller that is electrically connected to this drive mechanism, and a display component that is electrically connected to this controller.

The pharmaceutical injection performed by the above pharmaceutical injection device is carried out on the basis of a pharmaceutical injection schedule produced in writing by a physician (the following Patent Literature 1 is a prior publication related to this, for example).

CITATION LIST

Patent Literature

Patent Literature 1: Japanese Laid-Open Patent Application 2002-336331

SUMMARY

Technical Problem

In the prior art discussed above, after the pharmaceutical syringe has been mounted to the pharmaceutical syringe mounting component provided inside the main body case, the patient himself pushes a pharmaceutical injection button, which causes a drive mechanism to drive a piston and infuse a specific amount of the pharmaceutical inside the pharmaceutical syringe into the patient's body.

This injection amount is based on the above-mentioned pharmaceutical injection schedule produced by a physician, and if the patient forgets to inject the pharmaceutical, he has to visit the physician and have the pharmaceutical injection schedule reset, which can be very inconvenient to the patient.

In light of the above problem encountered with a conventional pharmaceutical injection device, it is an object of the present invention to provide a more convenient pharmaceutical injection device and method for controlling a pharmaceutical injection device.

Solution to Problem

To achieve this object, the invention has a configuration comprising a main body case that has an opening through which an injection needle is inserted and retracted; a pharmaceutical syringe mounting component that is provided inside the main body case and onto which a pharmaceutical syringe is mounted; a piston that is provided movably with respect to the pharmaceutical syringe mounted onto the pharmaceutical syringe mounting component; a drive mechanism that drives the piston; a display component that displays information related to the injection of a pharmaceutical; and a controller that is electrically connected to the drive mechanism, the display component, and the memory, and resets the current pharmaceutical dose by comparing a planned cumulative pharmaceutical dose, which is the planned cumulative amount of pharmaceutical injected up to the last time on the basis of the pharmaceutical injection schedule stored in the memory, with an actual cumulative pharmaceutical dose, which is the cumulative amount of pharmaceutical actually injected up to the last time. This achieves the stated object.

Specifically, the present invention is configured such that the current pharmaceutical dose is reset by comparing the planned cumulative pharmaceutical dose, which is the planned cumulative amount of pharmaceutical injected up to the last time on the basis of the pharmaceutical injection schedule stored in the memory, with the actual cumulative pharmaceutical dose, which is the cumulative amount of pharmaceutical actually injected up to the last time. Therefore, even if the patient should forget to inject the pharmaceutical, for example, this pharmaceutical injection device will itself reset the current pharmaceutical dose, and as a result there is no need for the patient to visit a physician and have the schedule reset, making the device very convenient to use.

Advantageous Effects

The present invention provides a more convenient pharmaceutical injection device and method for controlling a pharmaceutical injection device.

BRIEF DESCRIPTION OF DRAWINGS

FIGS. 16a to 16i are diagrams of the display component of the pharmaceutical injection device pertaining to Embodiment 1 of the present invention;

FIG. 23 is a diagram of a pharmaceutical injection schedule used with the pharmaceutical injection device pertaining to Embodiment 1 of the present invention;

FIG. 24 is a diagram of a pharmaceutical injection schedule and pharmaceutical injection results for the pharmaceutical injection device pertaining to Embodiment 1 of the present invention;

FIG. 25 is a diagram of a corrected pharmaceutical injection schedule and pharmaceutical injection results for the pharmaceutical injection device pertaining to Embodiment 1 of the present invention;

FIG. 26 is a diagram of a pharmaceutical injection schedule used with the pharmaceutical injection device pertaining to Embodiment 2 of the present invention;

FIG. 27 is a diagram of a pharmaceutical injection schedule and pharmaceutical injection results for the pharmaceutical injection device pertaining to Embodiment 2 of the present invention;

FIG. 28 is a diagram of a corrected pharmaceutical injection schedule and pharmaceutical injection results for the pharmaceutical injection device pertaining to Embodiment 2 of the present invention;

FIG. 29 is a diagram of a pharmaceutical injection schedule and pharmaceutical injection results for the pharmaceutical injection device pertaining to Embodiment 2 of the present invention;

FIG. 30 is a diagram of a corrected pharmaceutical injection schedule and pharmaceutical injection results for the pharmaceutical injection device pertaining to Embodiment 2 of the present invention;

FIGS. 33j to 33l are diagrams of the display component of the pharmaceutical injection device pertaining to Embodiment 3 of the present invention;

FIG. 34 is a diagram of a pharmaceutical injection schedule used with the pharmaceutical injection device pertaining to Embodiment 3 of the present invention;

FIG. 35 is a diagram of a pharmaceutical injection schedule and pharmaceutical injection results for the pharmaceutical injection device pertaining to Embodiment 3 of the present invention;

FIG. 36 is a diagram of a corrected pharmaceutical injection schedule and pharmaceutical injection results for the pharmaceutical injection device pertaining to Embodiment 3 of the present invention;

FIG. 37 is a diagram of a pharmaceutical injection schedule and pharmaceutical injection results for the pharmaceutical injection device pertaining to Embodiment 3 of the present invention;

FIG. 38 is a diagram of a corrected pharmaceutical injection schedule and pharmaceutical injection results for the pharmaceutical injection device pertaining to Embodiment 3 of the present invention;

FIG. 39 is a diagram of a corrected pharmaceutical injection schedule and pharmaceutical injection results for the pharmaceutical injection device pertaining to Embodiment 3 of the present invention;

FIG. 40 is a diagram of a further corrected pharmaceutical injection schedule and pharmaceutical injection results for the pharmaceutical injection device pertaining to Embodiment 3 of the present invention;

FIG. 43 is a diagram of a pharmaceutical injection schedule and pharmaceutical injection results for the pharmaceutical injection device pertaining to a modification example of Embodiment 1 of the present invention;

FIG. 44 is a diagram of a corrected pharmaceutical injection schedule and pharmaceutical injection results for the pharmaceutical injection device pertaining to a modification example of Embodiment 1 of the present invention;

FIG. 50 is a flowchart of the operation of the pharmaceutical injection device pertaining to a modification example of Embodiment 3 of the present invention.

DESCRIPTION OF EMBODIMENTS

Embodiments of the present invention will now be described through reference to the appended drawings.

Embodiment 1

1-1. Configuration of Pharmaceutical Injection Device

Figure 1:
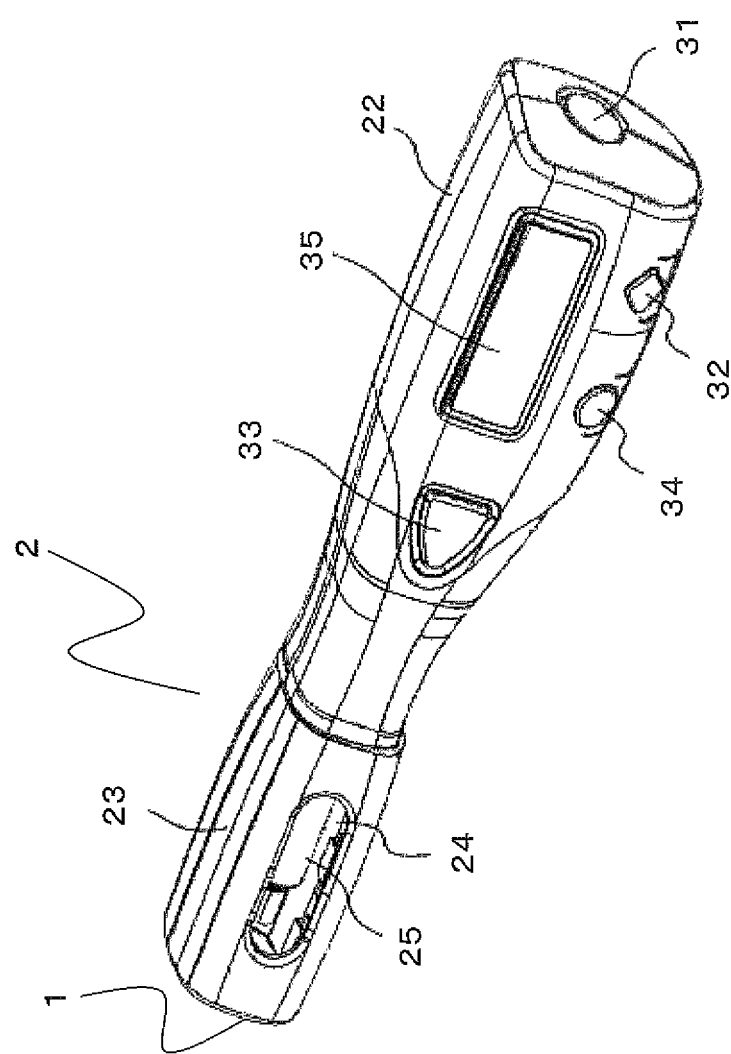
FIG. 1 is an oblique view of the pharmaceutical injection device pertaining to Embodiment 1 of the present invention.
Figure 2:
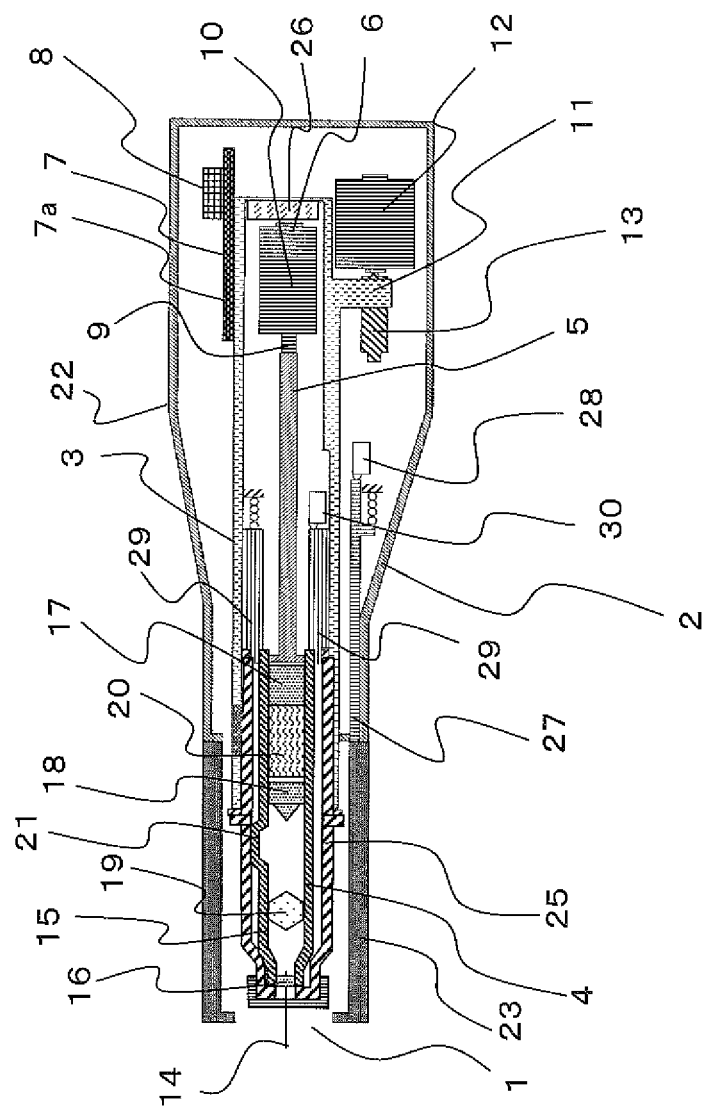
FIG. 2 is a cross section of the pharmaceutical injection device pertaining to Embodiment 1 of the present invention.

FIG. 1 is an oblique view of the pharmaceutical injection device pertaining to Embodiment 1. FIG. 2 is a cross section of the pharmaceutical injection device pertaining to Embodiment 1.

As shown in FIGS. 1 and 2, the pharmaceutical injection device in this embodiment comprises a substantially cylindrical main body case 2 having on the distal end side an injection needle insertion and retraction opening 1 through which an injection needle is inserted and retracted, a pharmaceutical syringe mounting component 3 that is provided inside the main body case 2, a pharmaceutical syringe 4 mounted inside this pharmaceutical syringe mounting component 3, a piston 5 that is provided movably with respect to this pharmaceutical syringe 4, a drive mechanism 6 that drives this piston 5, a controller 7 that is electrically connected to this drive mechanism 6, and an orientation sensor 8 that is electrically connected to this controller 7. The orientation sensor 8 is mounted on a substrate 7a having the controller 7, and is installed so that the substrate 7a will be parallel to the drive direction of the piston 5.

The drive mechanism 6 is made up of a bolt 9 inserted into a rear end opening in the piston 5, and a piston drive motor 10 for driving the bolt 9. Specifically, the drive mechanism 6 is configured so that when the piston drive motor 10 is rotated in one direction, the bolt 9 pushes the piston 5 toward the injection needle insertion and retraction opening 1, and when the piston drive motor 10 is rotated in the other direction, the piston 5 is pulled back toward the piston drive motor 10.

The piston drive motor 10 and the piston 5 are disposed along with the pharmaceutical syringe 4 inside the pharmaceutical syringe mounting component 3, and female threads 11 are provided toward the outside of the rear end of the pharmaceutical syringe mounting component 3. A bolt 13 of a needle insertion and retraction drive motor 12 meshes with these female threads 11. That is, when the needle insertion and retraction drive motor 12 is driven, the female threads 11 and the bolt 13 mesh, causing the pharmaceutical syringe mounting component 3 to move back and forth with respect to the injection needle insertion and retraction opening 1, and this causes an injection needle 14 provided on the distal end side of the pharmaceutical syringe 4 to come out of the injection needle insertion and retraction opening 1.

Figure 9:
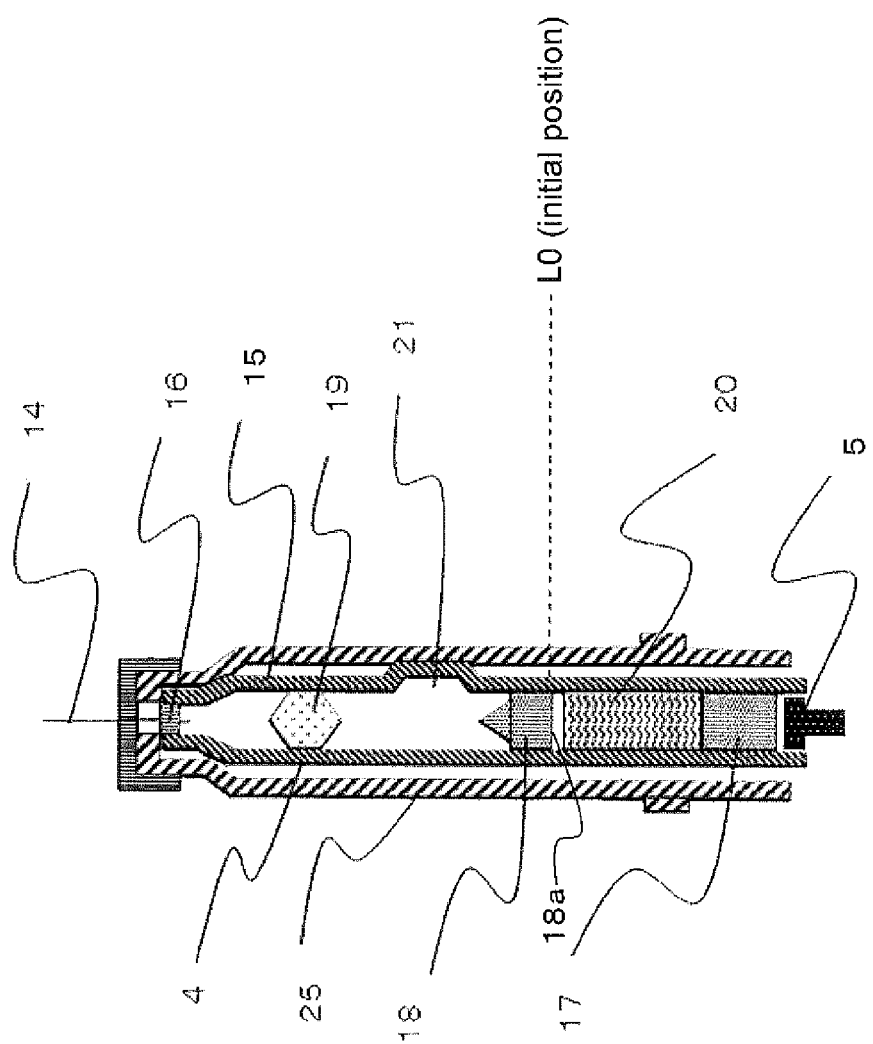
FIG. 9 is a cross section of the operating state during mixing in the pharmaceutical injection device pertaining to Embodiment 1 of the present invention.

FIG. 9 is a cross section of the area around the pharmaceutical syringe 4, and serves to illustrate the operation of the pharmaceutical injection device in Embodiment 1.

As shown in FIGS. 2 and 9, the pharmaceutical syringe 4 has a cylinder 15, a distal end gasket 16 provided on the distal end side inside this cylinder 15, a push-in gasket 17 provided on the rear end side inside the cylinder 15, a separation gasket 18 provided in the middle inside the cylinder 15, a solid pharmaceutical 19 contained inside the cylinder 15 between the distal end gasket 16 and the separation gasket 18, a liquid pharmaceutical 20 contained inside the cylinder 15 between the push-in gasket 17 and the separation gasket 18, and a bypass 21 that protrudes in the outer peripheral direction of the cylinder 15 at the portion of the cylinder 15 between the distal end gasket 16 and the separation gasket 18. The pharmaceutical injection device in Embodiment is configured such that after the orientation has been sensed by the orientation sensor 8, the controller 7 (see FIG. 2) actuates the drive mechanism 6, so that the push-in gasket 17 is pressed by the piston 5 to the distal end gasket 16 side.

Also, the rate at which the push-in gasket 17 is pushed in by the piston 5 is set so that if we let V1 be the push-in rate when the separation gasket 18 reaches the bypass 21, V2 be the push-in rate at the point when the separation gasket 18 goes through the bypass 21, V3 be the push-in rate at the point when air is vented after the separation gasket 18 has gone through the bypass 21, and V4 be the push-in rate at the point when a pharmaceutical is injected after air venting, the push-in rate V2 will be lower than the push-in rate V1.

Returning to FIGS. 1 and 2, the main body case 2 is made up of a housing 22 and a distal end cap 23 on the distal end side of the housing 22. The distal end cap 23 is removably mounted to the housing 22. A conformation window 24 is provided on the outer peripheral part of the distal end cap 23.

After the pharmaceutical syringe 4 has been mounted inside the pharmaceutical syringe mounting component 3, the outer periphery of the pharmaceutical syringe 4 is covered by a syringe cover (25 in FIG. 9), and in this state, the injection needle 14 is mounted to the distal end gasket 16 on the distal end side of the pharmaceutical syringe 4. When the piston 5 pushes the push-in gasket 17 forward, the liquid pharmaceutical 20 goes through the bypass 21 and flows to the solid pharmaceutical 19 side, and when the push-in gasket 17 moves farther forward, the liquid pharmaceutical 20 in which the solid pharmaceutical 19 has been dissolved flows out of the injection needle 14.

The rotation of the piston drive motor 10 is detected by an encoder 26 (see FIG. 2), which senses the amount by which the piston 5 protrudes. The solid pharmaceutical 19 and the liquid pharmaceutical 20 contained inside the pharmaceutical syringe 4 are put in at a pharmaceutical company, etc.

The housing 22 of the main body case 2 also houses a number of switches. More specifically, a distal end cap detector switch 28 is disposed at the rear end of a control rod 27 provided around the outer periphery of the pharmaceutical syringe mounting component 3, and when the distal end cap 23 is mounted to the distal end of the housing 22, the control rod 27 is pushed rearward, and the distal end cap detector switch 28 detects that the distal end cap 23 has been mounted. A control rod 29 is disposed inside the pharmaceutical syringe mounting component 3, and when the control rod 29 is pushed rearward by the syringe cover 25, a syringe cover detector switch 30 detects that the syringe cover 25 has been mounted.

The orientation sensor 8 is mounted on the substrate 7a having the controller 7, and is installed so that the substrate 7a will be parallel to the drive direction of the piston 5, which allows acceleration with respect to the main body case 2 to be sensed more favorably. In this embodiment, the substrate 7a is disposed parallel to the drive direction of the piston 5, but may instead be installed perpendicular to the drive direction of the piston 5.

Returning to FIG. 1, various control buttons and so forth are provided to the outer periphery of the housing 22 of the main body case 2. More specifically, a power button 31 is provided to the rear end of the housing 22. A mix button 32, a pharmaceutical injection button 33, an end button 34, and a display component 35 are provided to the outer periphery of the housing 22. The mix button 32, the pharmaceutical injection button 33, the end button 34, and the display component 35 are electrically connected to the controller 7.

1-2. Electrical Configuration of Pharmaceutical Injection Device

Figure 3:
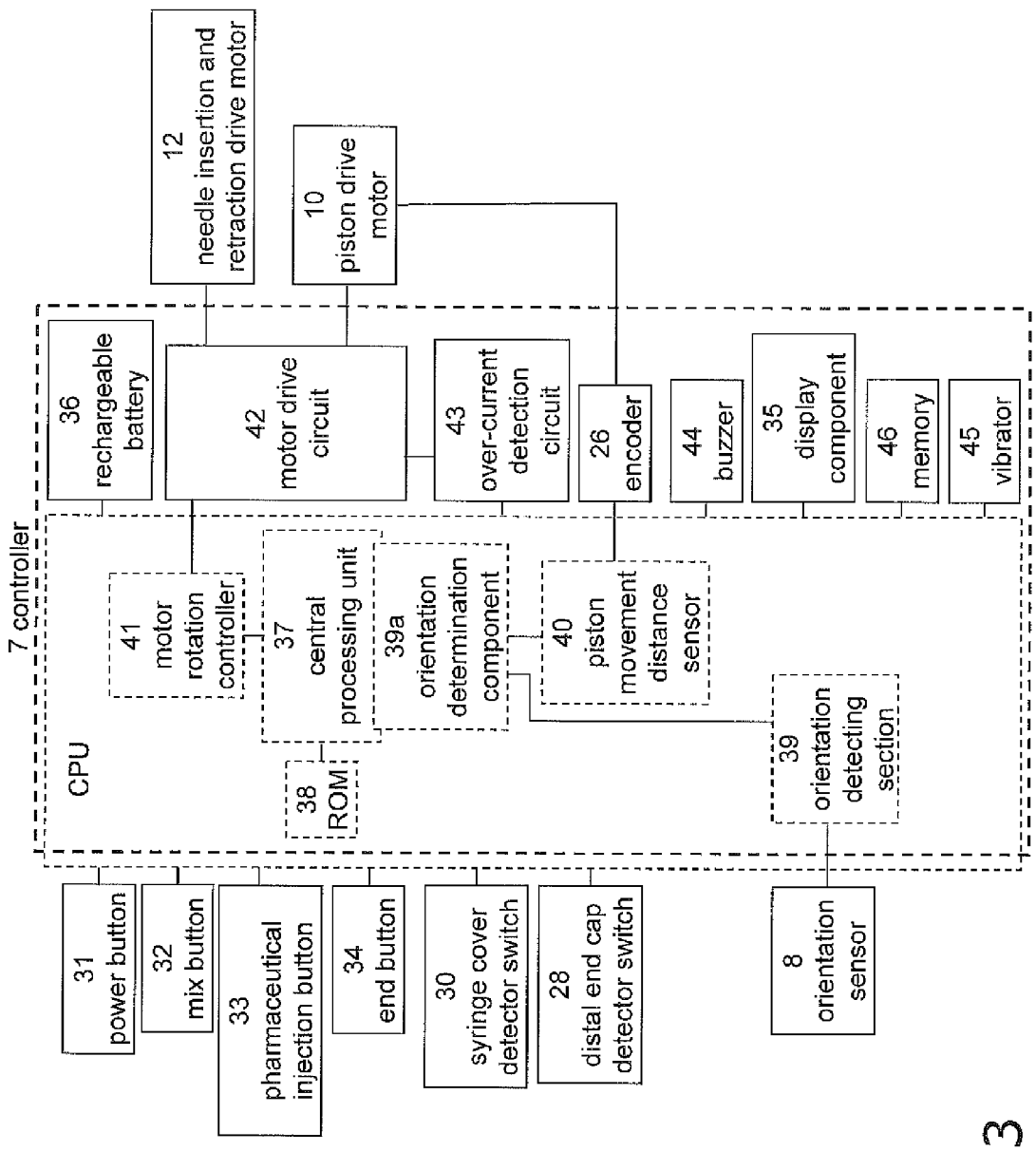
FIG. 3 is a control block diagram of the simplified electrical configuration of the pharmaceutical injection device pertaining to Embodiment 1 of the present invention.

FIG. 3 is a block diagram of the electrical configuration of the pharmaceutical injection device in Embodiment 1. The controller 7 is constituted by a microprocessor, and a rechargeable battery 36 (shown in FIG. 3) is connected to the controller 7 and other electrically driven parts. The electrical connection state of the rechargeable battery 36 and the other electrically driven parts is not shown, to keep FIG. 3 from being too complicated.

A central processing unit 37 is provided inside the controller 7. The central processing unit 37 performs operational control over the various blocks shown in FIG. 3. A program that performs this operational control is written into a ROM 38. An orientation detecting section 39, a piston movement distance sensor 40, and a motor rotation controller 41 are connected to the central processing unit 37. An orientation determination component 39a and the orientation sensor 8 are connected to the orientation detecting section 39, and the orientation sensing result from the orientation sensor 8 is converted into information for determining the orientation at the orientation determination component 39a. The orientation determination component 39a performs various kinds of operational control according to the orientation, such as using the orientation information obtained from the orientation detecting section 39 to compare the inclination sensed by the orientation sensor 8 with a set value, determine whether or not to drive the piston drive motor 10, etc.

The piston movement distance detector 40 is connected to the encoder 26, the encoder 26 is attached to the piston drive motor 10, and the movement distance of the piston 5 is detected by detecting the rotation of the piston drive motor 10.

The motor rotation controller 41 is connected to a motor drive circuit 42, and when the value detected by the piston movement distance detector 40 reaches a set value, the motor drive circuit 42 is controlled to change the movement speed of the piston 5. The piston drive motor 10 and the needle insertion and retraction drive motor 12 are connected to the motor drive circuit 42, and the motor drive circuit 42 is connected to an over-current detection circuit 43.

The motor drive circuit 42 is controlled by the motor rotation controller 41, and drives the piston drive motor 10 and the needle insertion and retraction drive motor 12.

The over-current detection circuit 43 is a circuit that detects the amount of current from the motor drive circuit 42, and detects malfunction in the piston drive motor 10 and the needle insertion and retraction drive motor 12.

The controller 7 is also connected to a buzzer 44 and a vibrator 45 for issuing a warning so as to alert the user to the current usage status of the pharmaceutical injection device in this embodiment.

The controller 7 is also connected to the display component 35, which displays warnings and information for operating the pharmaceutical injection device in this embodiment, and to a memory 46 for recording various kinds of data, including a pharmaceutical injection schedule. The above configuration will now be described through reference to an operational flowchart, and an example of the method for controlling a pharmaceutical injection device of the present invention will also be discussed.

1-3. Pharmaceutical Mixing Operation

Figure 4:
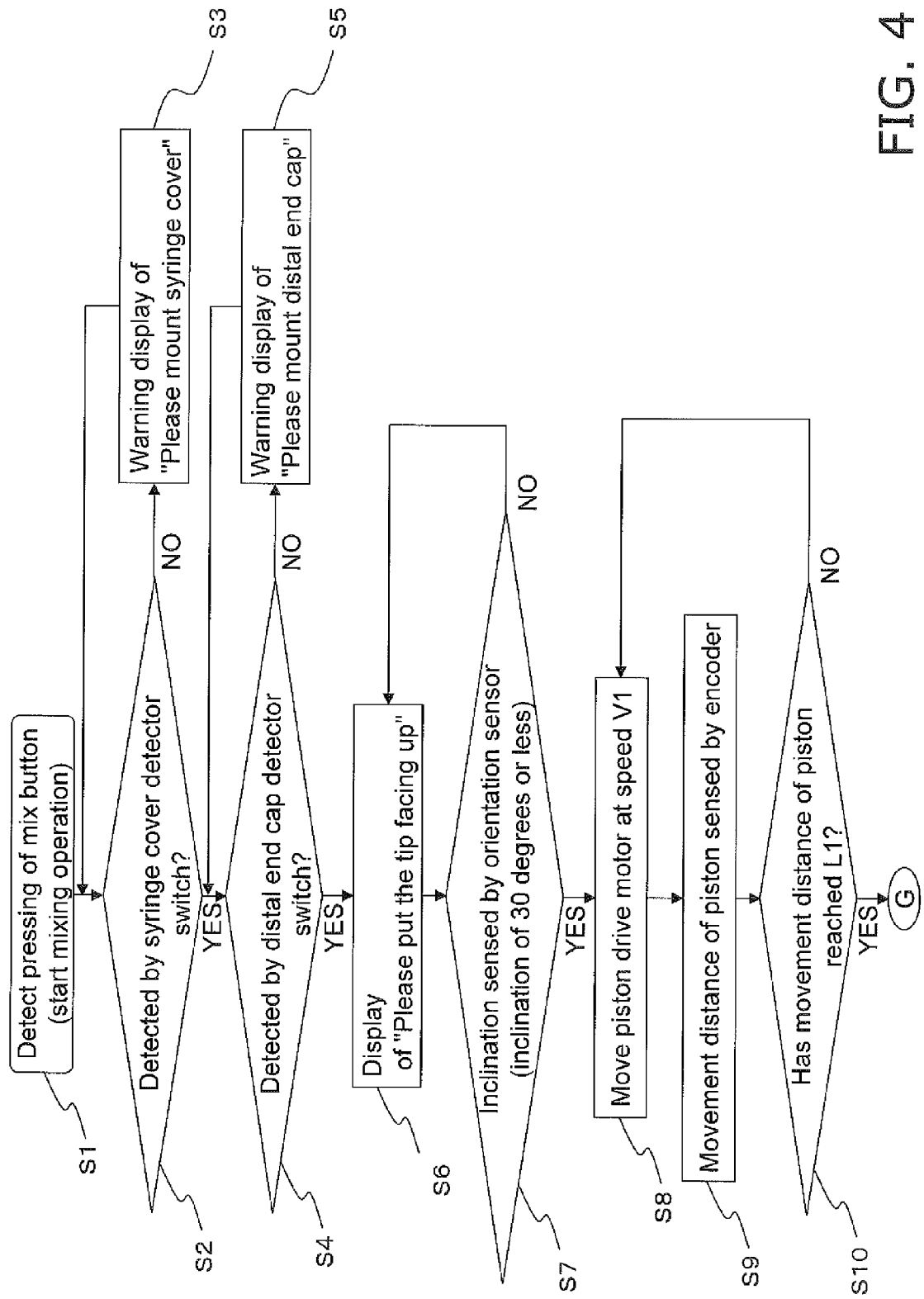
FIG. 4 is a flowchart of the operational control of the pharmaceutical injection device pertaining to Embodiment 1 of the present invention.
Figure 5:
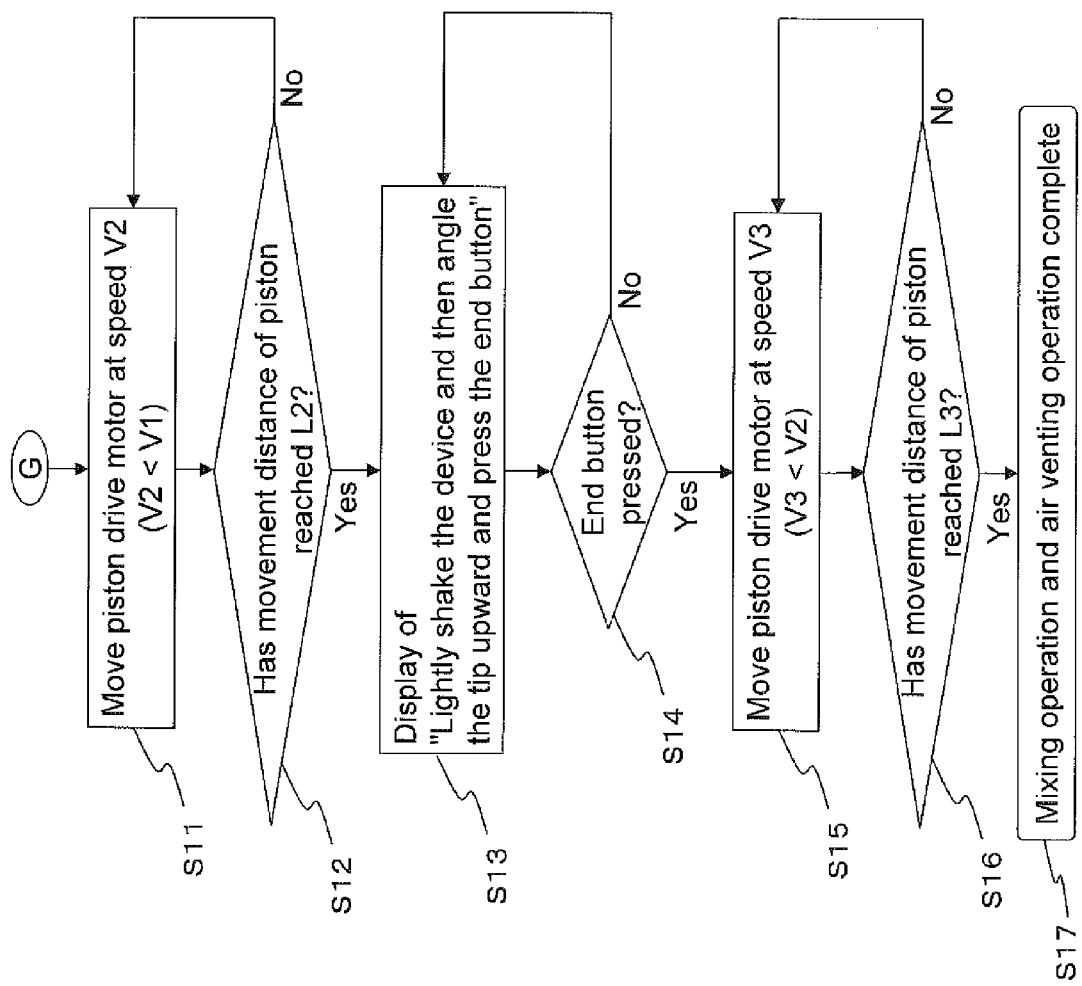
FIG. 5 is a flowchart of the operational control of the pharmaceutical injection device pertaining to Embodiment 1 of the present invention.

FIGS. 4 and 5 are flowcharts of the operational control during mixing the pharmaceutical in the pharmaceutical injection operation of the pharmaceutical injection device pertaining to Embodiment 1.

As shown in S1 in FIG. 4, first the user presses the mix button 32 in FIG. 1. Then, in S2 in FIG. 4, the syringe cover detector switch 30 detects whether or not the syringe cover 25 has been mounted. If the syringe cover 25 has not been mounted, in S3 a warning display of "Please mount syringe cover" is given on the display component 35 (see FIG. 1).

Once the mounting of the syringe cover 25 has been confirmed, the distal end cap detector switch 28 checks whether or not the distal end cap 23 has been mounted, as shown in S4 in FIG. 4. Here again, if the distal end cap 23 has not been mounted, a warning display of "Please mount distal end cap" is given on the display component 35 (see FIG. 1).

The following operation is not performed if the syringe cover 25 and the distal end cap 23 have both been mounted, as shown in S2 and S4.

Once it has been confirmed that the syringe cover 25 and the distal end cap 23 have been mounted in S2 and S4, a display of "Please put the tip facing up" is left on the display component 35 as shown in S6 in FIG. 4 for a specific length of time.

After the display in S6, the inclination is sensed by the orientation sensor 8 in S7. Hereinafter, the inclination will be referred to by using the direction perpendicular to the horizontal plane as zero degrees. If the inclination exceeds a specific value (the set value), the controller 7 halts the operation until the inclination falls back to within the specific value (the set value), and operation is restarted once the inclination has been within the specific value for a specific length of time. When leakage from the injection needle 14 is taken into account, it is preferable for the inclination at which operation is performed to be 30 degrees or less.

Although not discussed in detail here, the inclination is continuously sensed by the orientation sensor 8 during the operation from S7 (FIG. 4) onward.

Figure 7:
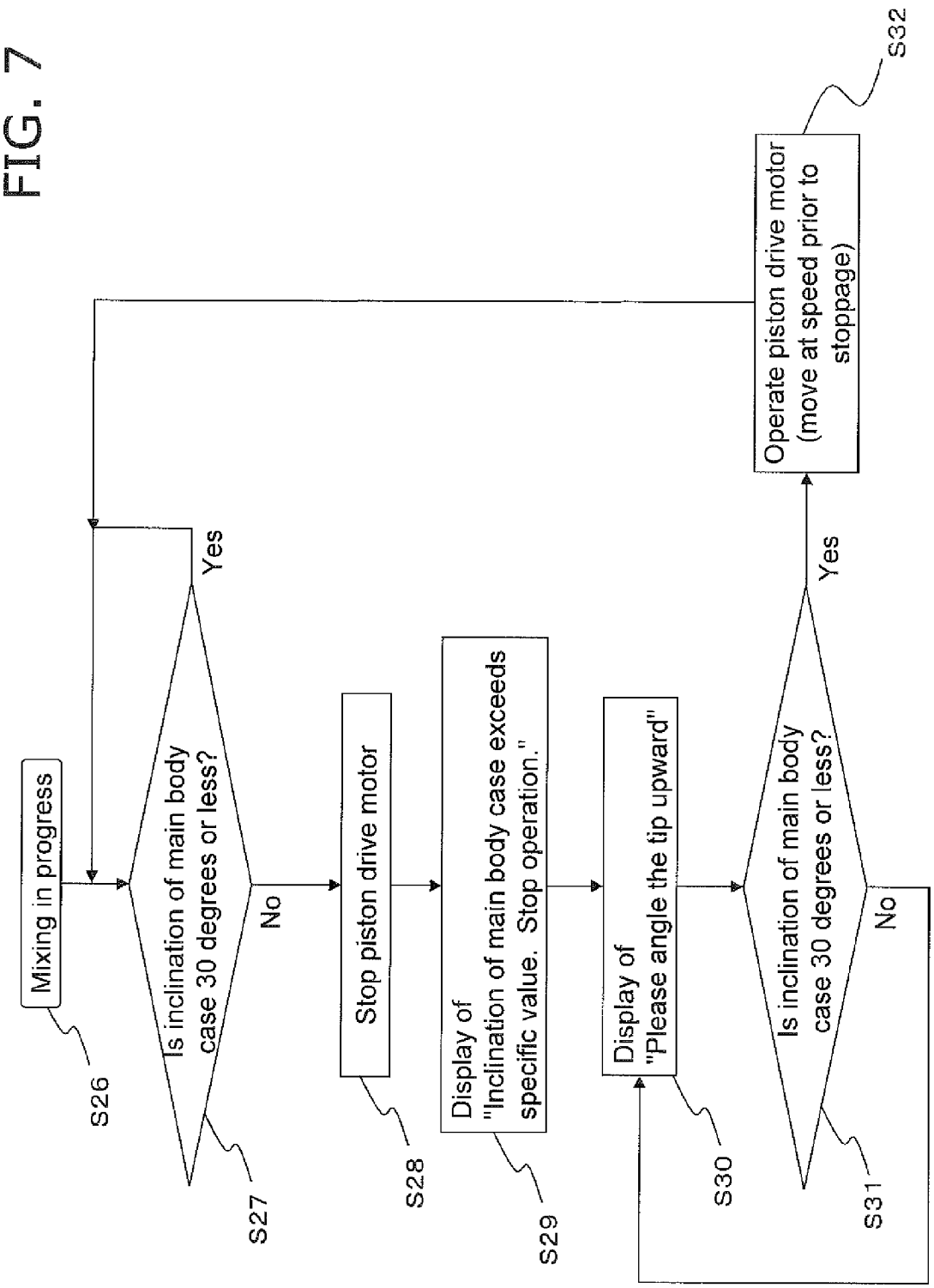
FIG. 7 is a flowchart of the operational control of the pharmaceutical injection device pertaining to Embodiment 1 of the present invention.

FIG. 7 is a flowchart of the operation of sensing the inclination of the pharmaceutical injection device in Embodiment 1. As shown in FIG. 7, the sensing of the inclination by the orientation sensor 8 is continued during the mixing operation (S26). If the inclination of the main body case 2 exceeds 30 degrees (S27), the controller 7 stops the piston drive motor 10 (S28), causes the display component 35 to give a warning display of "Main body case is tilted too far. Operation has been stopped" (S29) and "Please put the tip facing up" (S30), which prompt the user not to tilt the main body case 2. S31 is a loop with S30, and is used to tell the user through a display that the inclination of the main body case 2 has dropped to 30 degrees or less.

S32 is used to restart the operation prior to the stoppage, and return to S8 (see FIG. 4) in the even that it was sensed in S31 that the inclination was 30 degrees or less.

Figure 10:
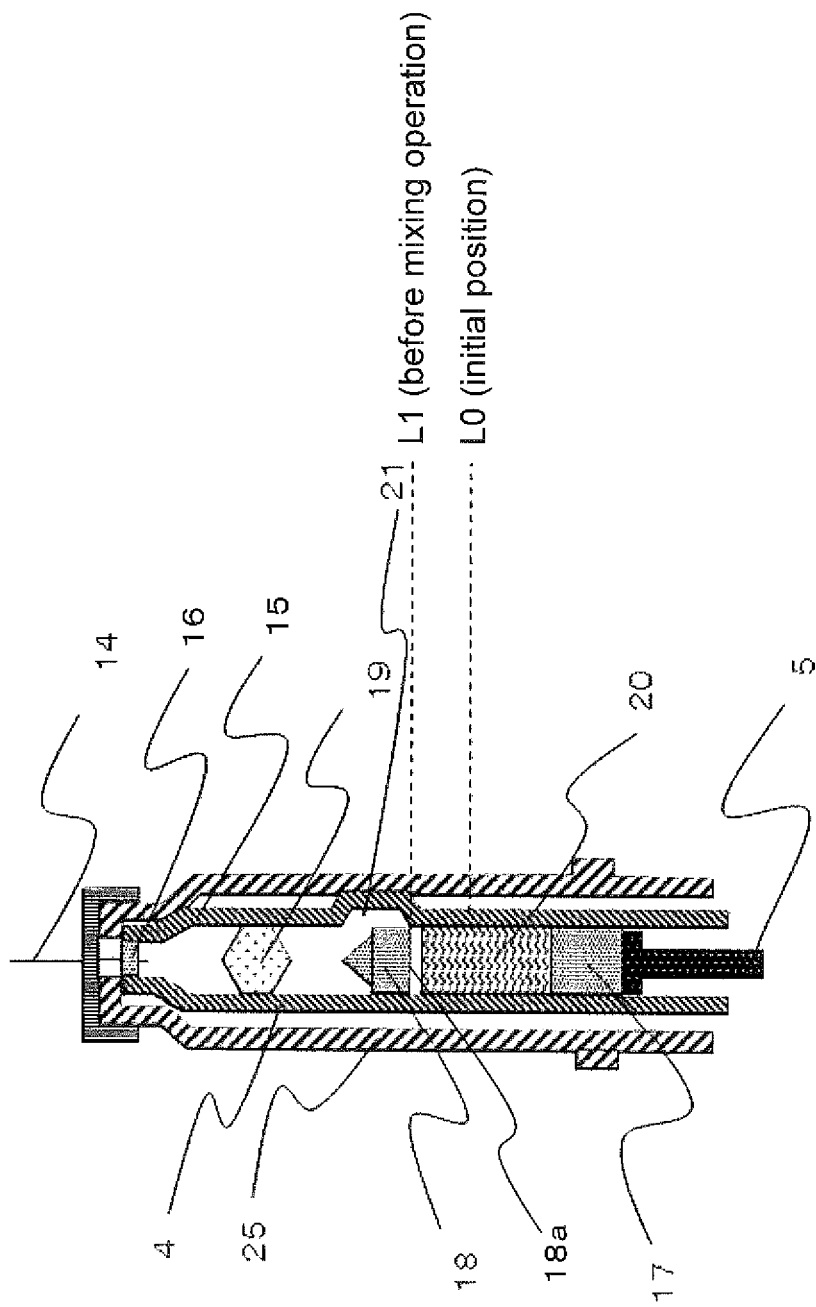
FIG. 10 is a cross section of the operating state during mixing in the pharmaceutical injection device pertaining to Embodiment 1 of the present invention.

In S8, as shown in FIG. 9, the controller 7 drives the piston drive motor 10 from its initial state prior to the mixing operation, at a speed V1 (push-in rate V1). As shown in S9, the movement distance of the piston 5 is calculated by the encoder 26 during drive of the piston 5. Then, as shown in S10, the controller 7 continues to move the piston drive motor 10 at the speed V1 (the push-in rate V1) until the rear end 18a of the separation gasket 18 goes from the initial position L0 in FIG. 10 to the position L1 a specific distance away. As shown in FIG. 10, L1 indicates the position where the rear end 18a of the separation gasket 18 touches the bypass 21, and is position information about the movement distance from L0 to L1, that is, until the rear end 18a of the separation gasket 18 changes from its initial state to a contact state. This L1 position information is stored ahead of time in the memory 46.

When the rear end position of the separation gasket 18 reaches L1, the mixing operation commences, and as shown in S11 in FIG. 5, the push-in rate V2 of the separation gasket by the piston drive motor 10 is switched so as to be lower than the push-in rate V1 (V2<V1).

Figure 11:
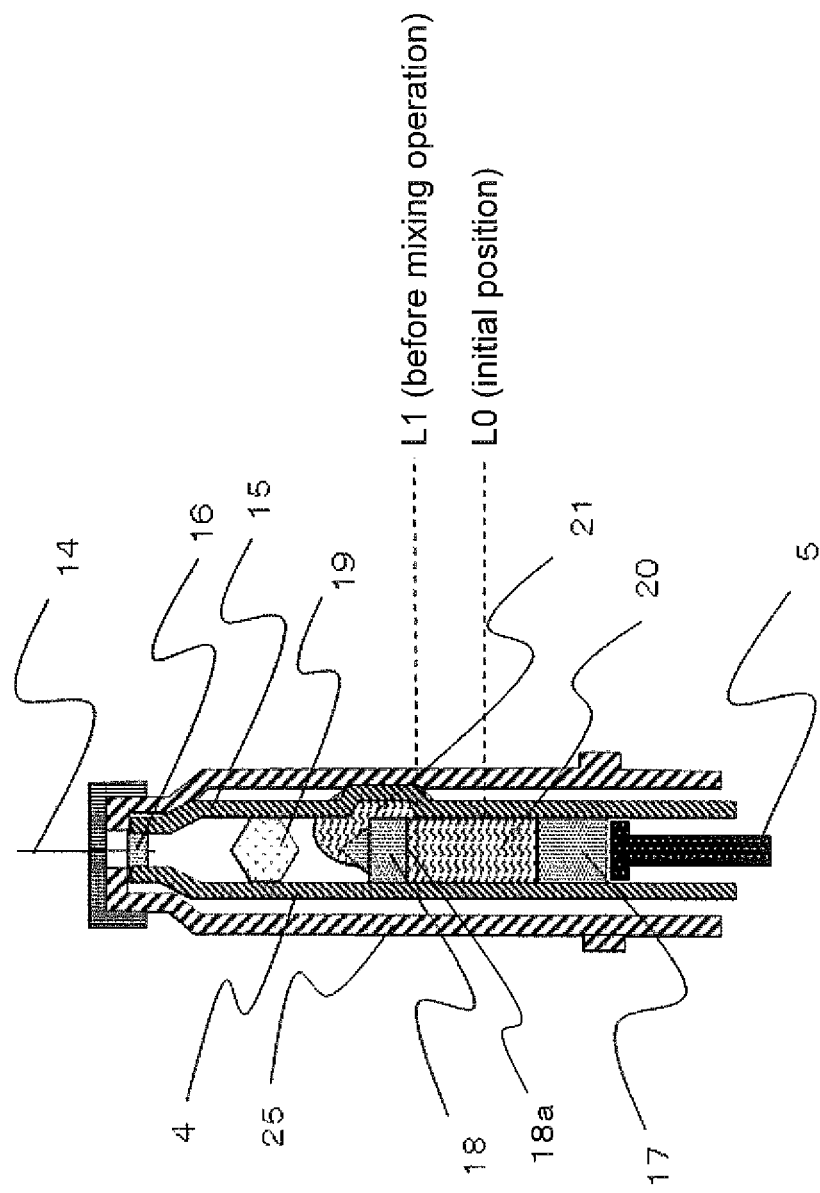
FIG. 11 is a cross section of the operating state during mixing in the pharmaceutical injection device pertaining to Embodiment 1 of the present invention.

As shown in FIG. 11, when the rear end 18a of the separation gasket 18 starts to pass through the bypass 21, the liquid pharmaceutical 20 begins to flow through the bypass 21 to the solid pharmaceutical 19 side, and the mixing operation is commenced.

Figure 12:
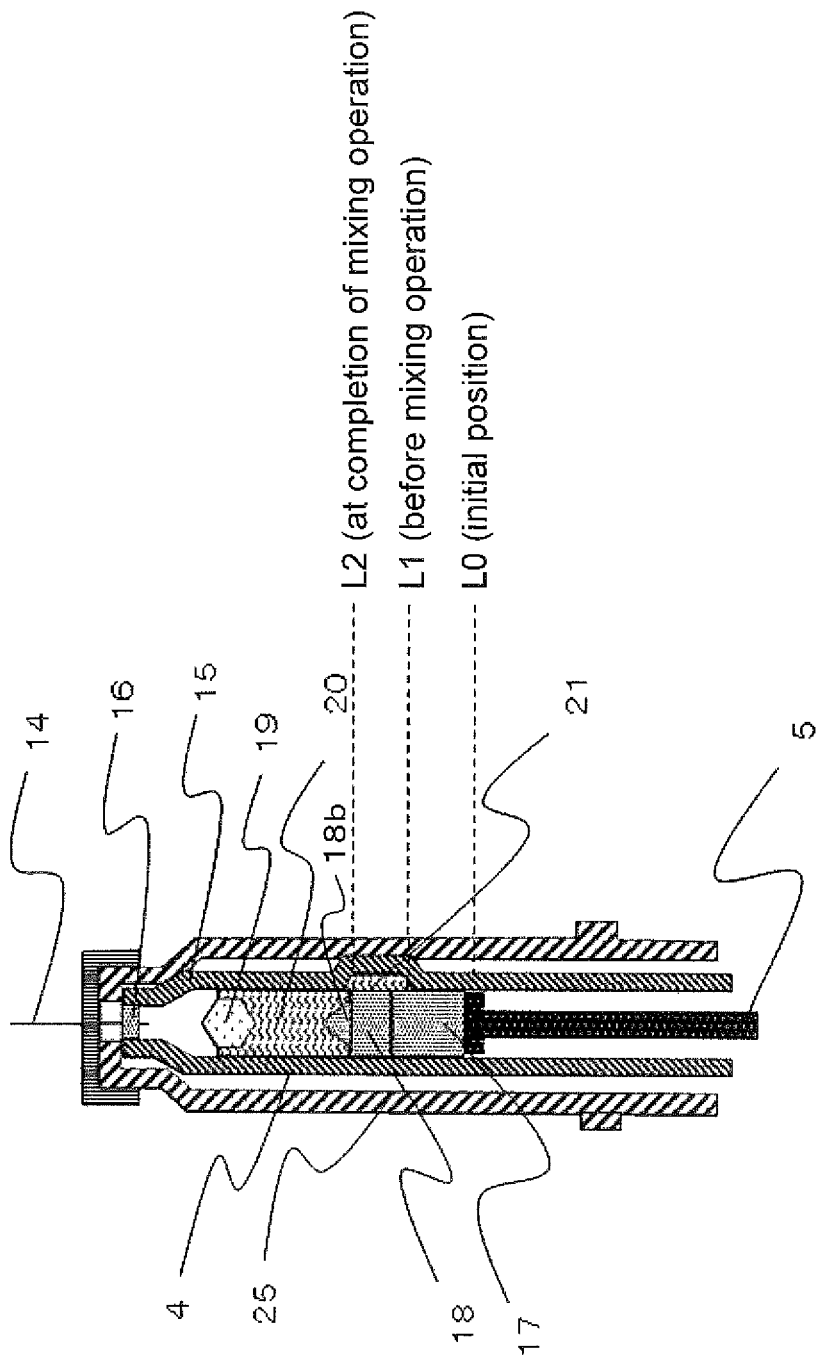
FIG. 12 is a cross section of the operating state during mixing in the pharmaceutical injection device pertaining to Embodiment 1 of the present invention.

Then, in S12, the controller 7 continues to move the piston drive motor 10 at the speed V2 (the push-in rate V2) until the distal end 18b of the separation gasket 18 reaches L2 in FIG. 12. The separation gasket 18 has a cylindrical portion and a conical portion, and in this embodiment the distal end 18b of the separation gasket 18 is the distal end of the cylindrical portion. The movement distance from L1 to L2, as shown in FIG. 12, is the movement distance up until the separation gasket 18 and the push-in gasket 17 come into contact, that is, it is the movement distance until the separation gasket 18 goes from its initial state to a state of being in contact with the push-in gasket 17. This L2 position information is stored ahead of time in the memory 46.

Because the push-in rate V2 of the separation gasket 18 by the piston drive motor 10 is thus set to be lower than the push-in rate V1, it is less likely that there will be a sudden surge in pressure on the solid pharmaceutical 19 side when the liquid pharmaceutical 20 passes through the bypass 21. As a result, this prevents some of the liquid pharmaceutical from squirting out of the distal end of the injection needle 14 mounted to the distal end gasket 16 of the cylinder 15, or from overflowing more than necessary. That is, liquid leakage from the distal end of the injection needle 14 reduced during pharmaceutical mixing, so the mixing operation can be carried out more favorably.

Next, as shown in FIG. 12, when the distal end position of the separation gasket 18 reaches L2, the display component 35 in FIG. 1 displays "Lightly shake the device and then angle the tip upward and press the end button" as shown in S13 in FIG. 5, and the operation of the piston drive motor 10 is temporarily halted. Also, the sensing of orientation is not carried out from the time of the above display until the end button 34 is pressed.

In S14 in FIG. 5, air venting starts when it has been detected that the end button 34 has been pressed as shown in FIG. 1.

1-4. Air Venting

In the air venting operation, while the inclination is being sensed by the orientation sensor 8, the push-in rate of the separation gasket 18 by the piston drive motor 10 is switched to a rate V3 so as to be lower than the push-in rate V1 (V3<V1). More preferably, as in this embodiment, the push-in rate V3 is set to be lower than the push-in rate V2 (V3<V2).

During the air venting operation, since liquid is most apt to leak from the distal end of the injection needle 14, the controller 7 further lowers the speed at which the piston 5 is moved (S15).

Figure 13:
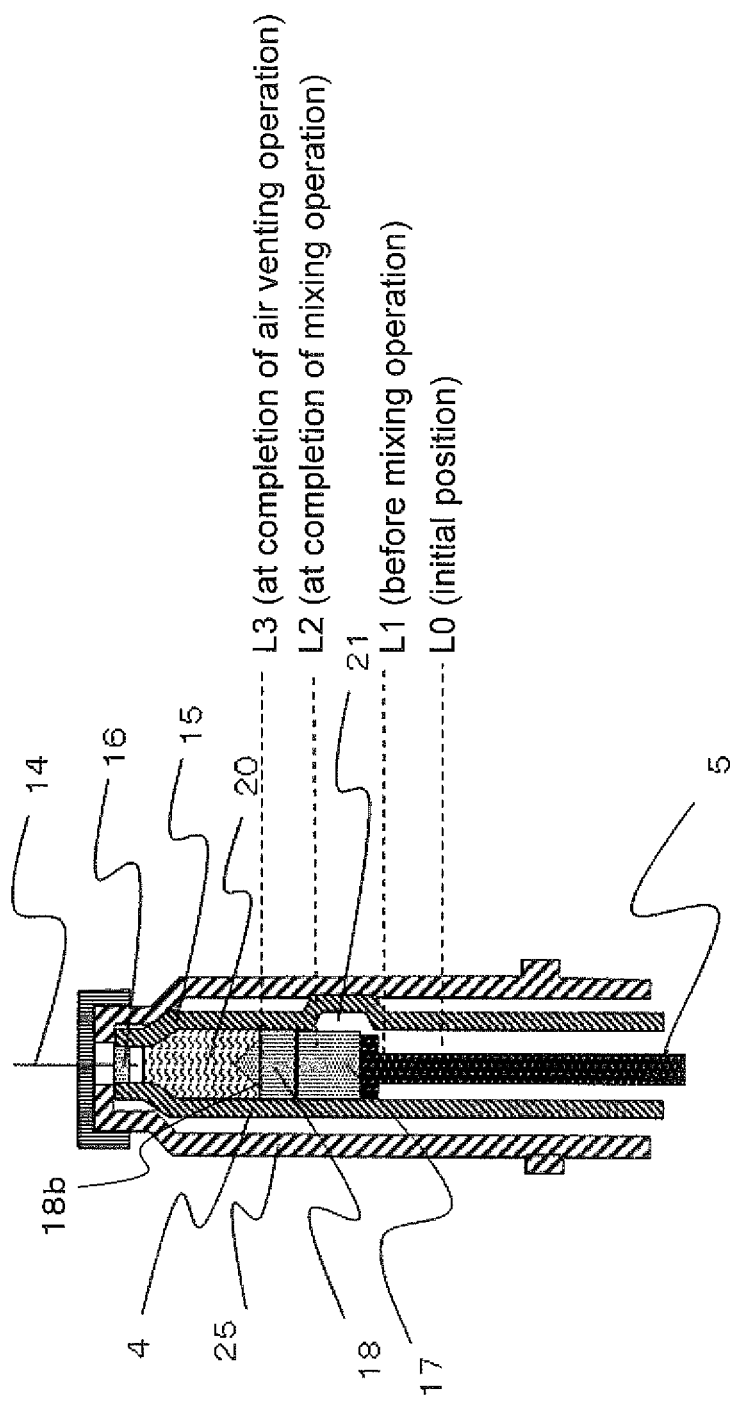
FIG. 13 is a cross section of the operating state during mixing in the pharmaceutical injection device pertaining to Embodiment 1 of the present invention.

Then, in S16, the piston drive motor 10 is actuated at the speed V3 (the push-in rate V3) until the distal end position of the separation gasket 18 arrives at L3. As shown in FIG. 13, the movement distance from L2 to L3 indicates the position after the separation gasket 18 and the push-in gasket 17 have passed through the bypass 21 in a state of being in contact with each other. Position information about L3 is stored ahead of time in the memory 46.

As shown in S17, the air vent operation is ended when the distal end position of the separation gasket 18 reaches L3.

Figure 6:
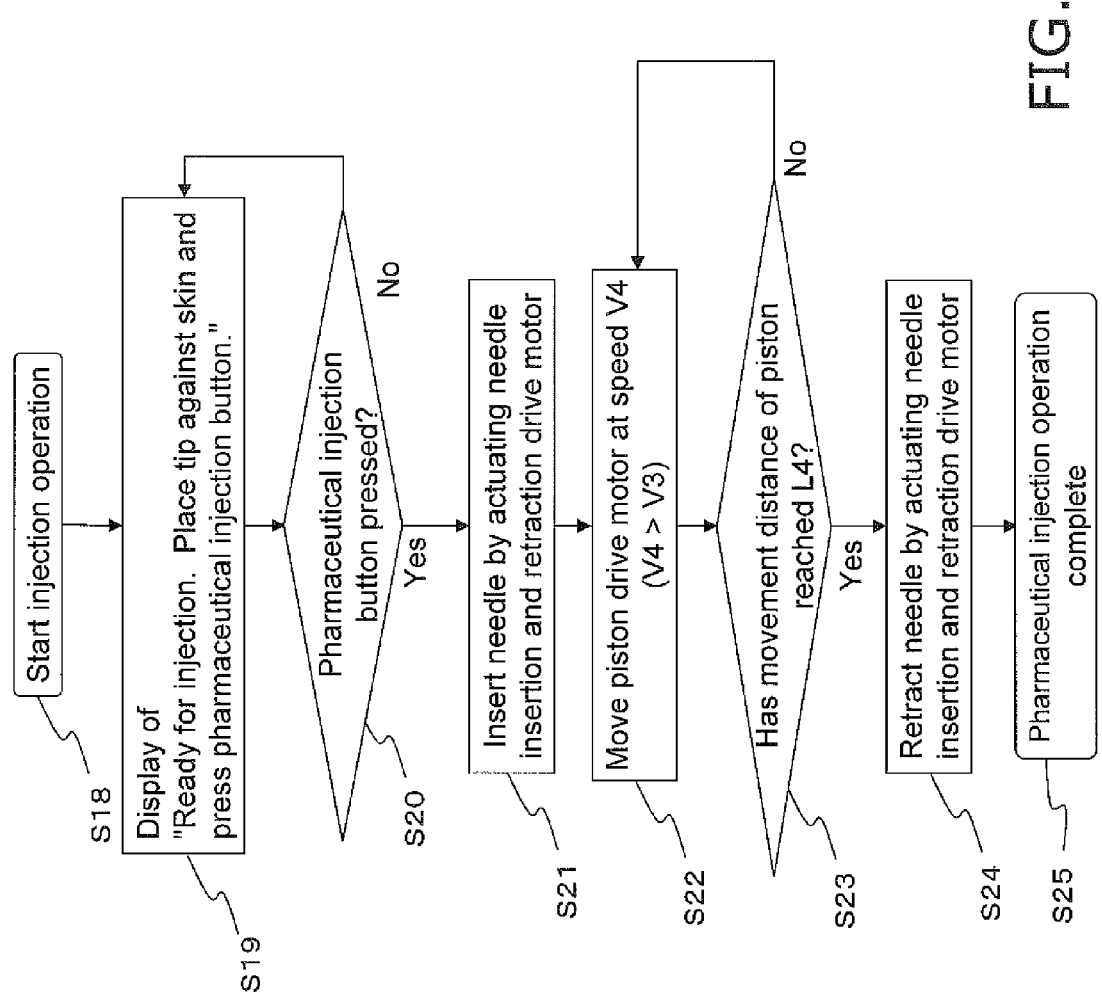
FIG. 6 is a flowchart of the operational control of the pharmaceutical injection device pertaining to Embodiment 1 of the present invention.

The pharmaceutical injection operation shown in S18 in FIG. 6 is then commenced.

1-5. Pharmaceutical Injection Operation

FIG. 6 is a flowchart of the control during pharmaceutical injection operation of the pharmaceutical injection device in Embodiment 1.

When the automatic mixing and air venting operation discussed above is complete, the controller 7 causes the display component 35 in FIG. 1 to display a message of "Ready for injection. Place tip against skin and press pharmaceutical injection button," and the operation of the piston drive motor 10 is temporarily halted.

Next, in S20, the operation of piercing the skin is commenced when it is detected that the pharmaceutical injection button 33 shown in FIG. 1 has been pressed. This needle insertion operation is accomplished by moving the needle insertion and retraction drive motor 12, as shown in S21. This "needle insertion operation" refers to an operation of driving the needle insertion and retraction drive motor 12 to move the pharmaceutical syringe mounting component 3 to the injection needle insertion and retraction opening 1 side, and thereby causing the injection needle 14 to stick out from the injection needle insertion and retraction opening 1.

At this point, since the injection needle insertion and retraction opening 1 is already been pressed against the side on the body where the injection is to be made, the injection needle 14 is moved toward the body, the injection needle 14 is plunged into the body, and the preparatory operation (needle insertion operation) prior to pharmaceutical injection is complete.

Then, when the preparatory operation (needle insertion operation) prior to pharmaceutical injection is complete, as shown in S22, the operation of pharmaceutical injection is commenced.

In the pharmaceutical injection operation, the push-in rate of the separation gasket by the piston drive motor 10 is switched to the rate V4 so as to be higher than the push-in rate V3 (V4>V3).

Since it is unlikely that there will be leakage from the distal end of the injection needle 14 during the pharmaceutical injection operation, the speed at which the piston 5 is moved can be increased.

Figure 14:
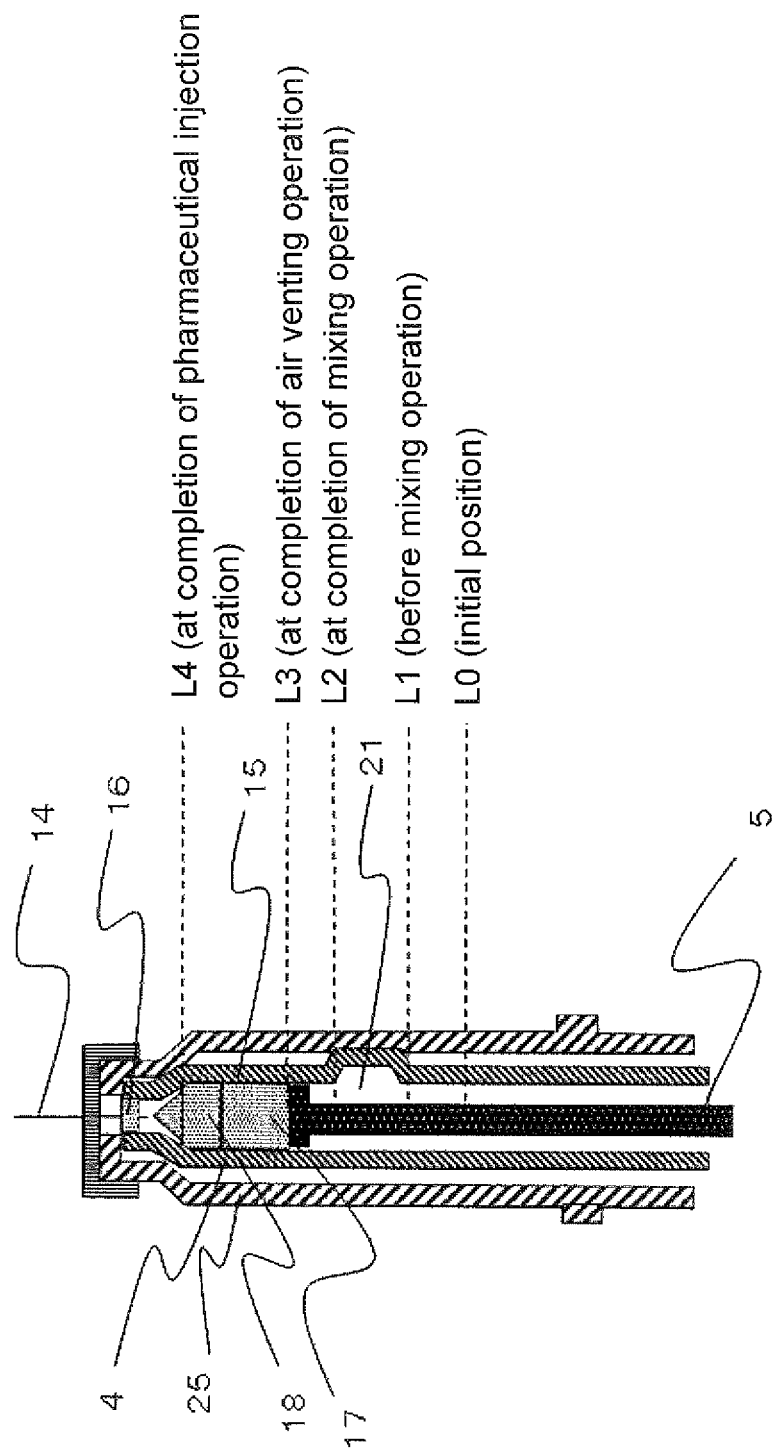
FIG. 14 is a cross section of the operating state during mixing in the pharmaceutical injection device pertaining to Embodiment 1 of the present invention.

Then, in S23, the controller 7 continues to move the piston drive motor 10 at the speed V4 (the push-in rate V4) until the distal end position of the separation gasket 18 reaches L4. As shown in FIG. 14, the movement distance from L3 to L4 indicates the position up to where the separation gasket 18 reaches the inclined portion of the distal end of the pharmaceutical syringe 4, and position information about this movement distance L4 is stored ahead of time in the memory 46.

Finally, when the distal end position of the separation gasket 18 reaches L4, the needle refraction operation is commenced. As shown in S24, in the needle retraction operation, the piston drive motor 10 is halted and the needle insertion and retraction drive motor 12 is moved.

This needle retraction operation involves driving the needle insertion and retraction drive motor 12 to move the pharmaceutical syringe mounting component 3 to the rear end side, and thereby stowing the injection needle 14 inside the injection needle insertion and refraction opening 1.

After this, as shown in S25, when the pharmaceutical syringe mounting component 3 reaches its initial position prior to the needle insertion operation, the needle retraction operation is complete, and the operation of pharmaceutical injection into the body is ended.

Figure 8:
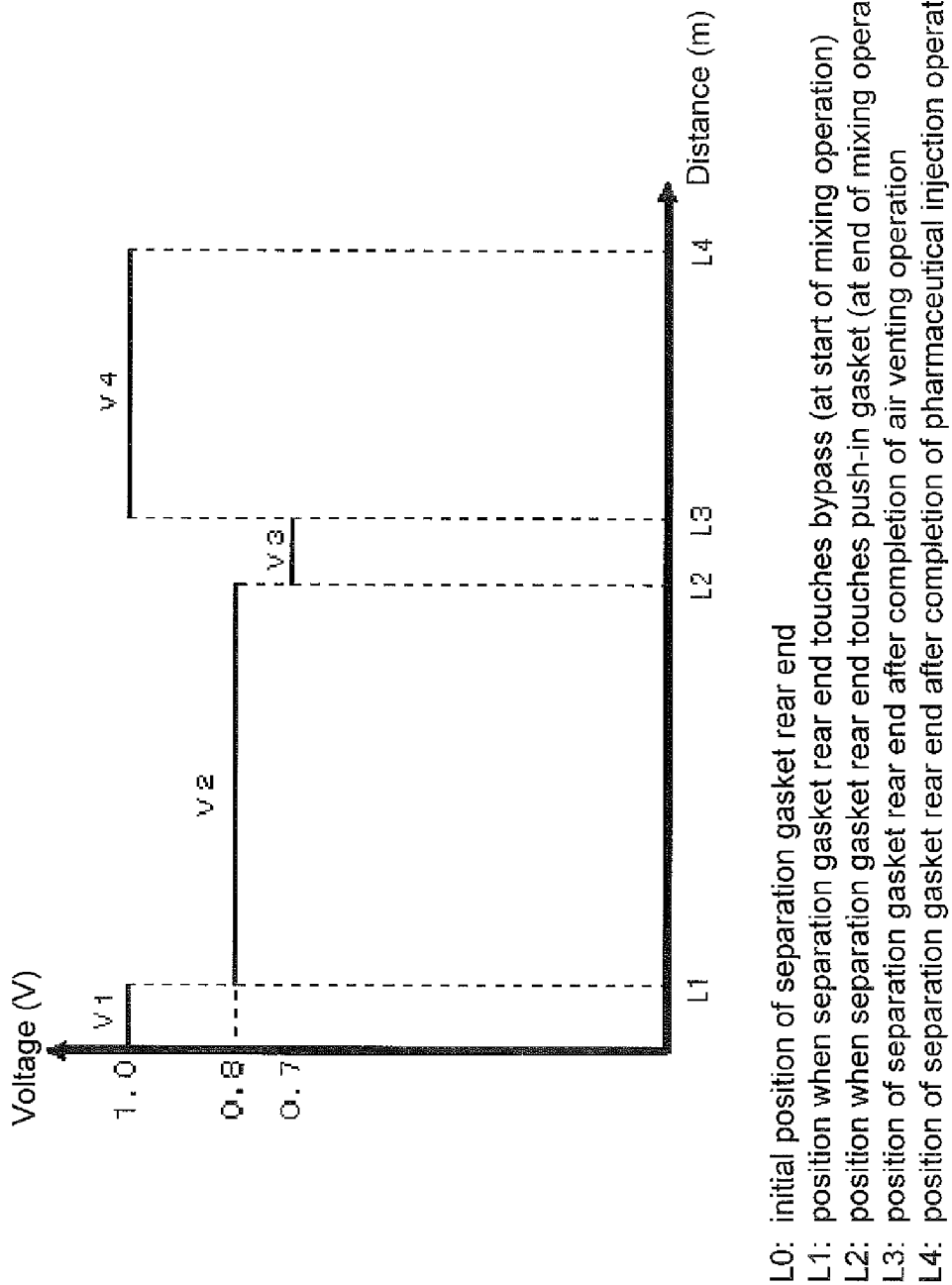
FIG. 8 is a graph of the operating state during mixing in the pharmaceutical injection device pertaining to Embodiment 1 of the present invention.

FIG. 8 is a graph of the operating state during mixing and injection with this pharmaceutical injection device. The vertical axis is the applied voltage (value) to a motor driver (not shown) for driving the piston drive motor 10, and the horizontal axis is the rear end position or distal end position of the separation gasket 18, showing a simulation of the flow of the operation at the above-mentioned push-in rates (V1, V2, V3, and V4). This was discussed in more specific terms above, but to resummarize about L0, L1, L2, L3, and L4, L0 is the initial position of the rear end 18a of the separation gasket 18. L1 is the position where the rear end 18a of the separation gasket 18 comes into contact with the bypass 21, and shows the position at the start of the mixing operation. L2 is the position where the rear end 18a of the separation gasket 18 comes into contact with the push-in gasket 17, and shows the position at the end of the mixing operation. L3 is the position of the distal end 18b of the separation gasket 18 after the air venting operation. L4 is the position of the distal end 18b of the separation gasket 18 after completion of the pharmaceutical injection operation.

Although not discussed detail above, the above-mentioned push-in rates are determined by changing the voltage values of a piston speed control signal (such as 1.0 volt for V1 and V4, 0.8 volt for V2, and 0.7 volt for V3). It can be seen that as the piston 5 is moved, the push-in rate V2 when the liquid pharmaceutical 20 passes through the bypass 21 is lower than the initial push-in rate V1, the push-in rate V3 during air venting is lower than the push-in rate V2, and the push-in rate V4 during pharmaceutical injection is higher than the push-in rate V3.

FIG. 8 is just one example of an embodiment, and a waiting period for user manipulation selection can be allocated as needed, such as between V2 and V3, or between V3 and V4, and in this case the mixing operation can be temporarily halted so that the various speeds are all zero. This is generally how the settings are made.

In the above description, position information about L0, L1, L2, L3, and L4 indicated the distal end position or rear end position of the separation gasket 18, but may be controlled with the movement distance of the piston 5 at a separate stage.

As discussed above, the pharmaceutical injection device in this embodiment is such that in the pharmaceutical mixing operation, the push-in rate V2 at the point when the separation gasket 18 passes through the bypass 21 is set lower than the push-in rate V1 when the separation gasket 18 is pushed in until it comes into contact with the bypass 21, so the liquid pharmaceutical 20 flows gently through the bypass 21 to the solid pharmaceutical 19 side. As a result, leakage from the distal end gasket 16 side can be reduced during this pharmaceutical mixing operation, the surroundings can be kept clean, without the pharmaceutical splashing onto the surrounding area when the pharmaceutical injection device is operated by the user, and the automatic mixing of the pharmaceuticals can be carried out easily and safely.

Next, the most salient features of this embodiment will be described.

1-6. Pharmaceutical Injection Schedule

In the above description, as illustrated in FIGS. 9 to 14, an example was described in which the pharmaceuticals inside the pharmaceutical syringe 4 were entirely injected into the patient by a single injection operation, but depending on the pharmaceuticals in the pharmaceutical syringe 4, they are sometimes divided up into a plurality of injections. As an example of this, we will describe an example in which the pharmaceuticals are injected on six consecutive days, namely, Sunday, Monday, Tuesday, Wednesday, Thursday, and Friday, with no pharmaceutical injection on Saturday. Here again, the operations illustrated in FIGS. 1 to 9 are carried out, but in order to keep the description from being overly complicated, redundant operations will be left out whenever possible.

FIG. 23 is a diagram of a pharmaceutical injection schedule. The pharmaceutical injection schedule shown in FIG. 23 is set up by a physician, who decides on the pharmaceutical injection days and the dosage. This pharmaceutical injection schedule is stored in the memory 46 (FIG. 3) as a pharmaceutical injection schedule preset by a physician. The pharmaceutical injection schedule shown in FIG. 23 involved injecting the pharmaceutical on six consecutive days, namely, Sundays, Mondays, Tuesdays, Wednesdays, Thursdays, and Fridays, with no pharmaceutical injection on Saturdays, in April 2011, with the planned pharmaceutical dose per day being 1.00 mg. No pharmaceutical had been injected as of Mar. 31, 2011.

As a result, the control program stored in the ROM 38 thereafter executed the operation while referring to the pharmaceutical injection schedule stored in the memory 46.

Figure 15:
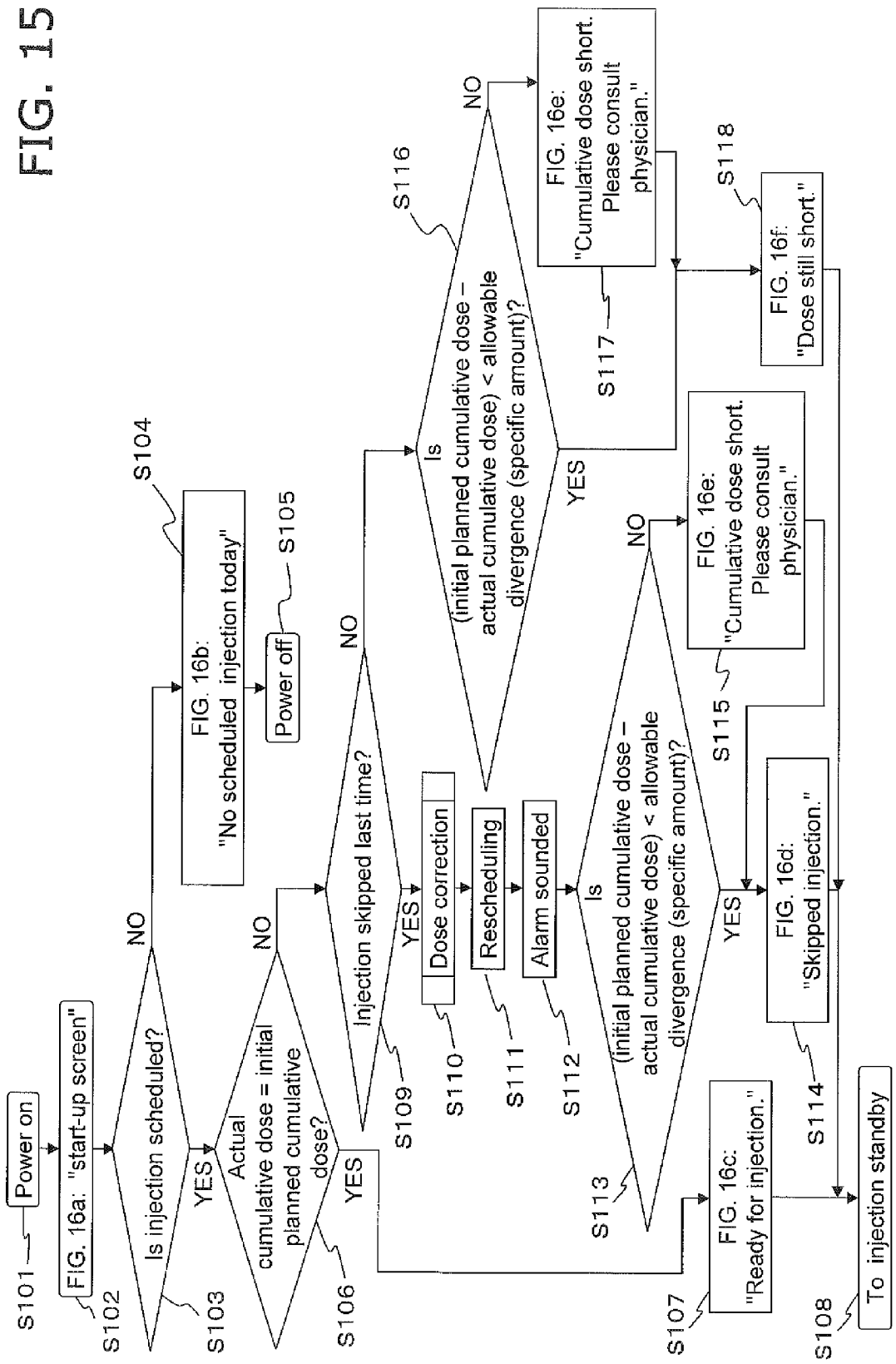
FIG. 15 is a flowchart of the operation of the pharmaceutical injection device pertaining to Embodiment 1 of the present invention.

Therefore, the pharmaceutical syringe 4 was mounted to the pharmaceutical syringe mounting component 3 as shown in FIGS. 1 and 2, and when the power button 31 was pressed in this state (S101 in FIG. 15), the pharmaceutical injection preparatory operation shown in FIG. 15 was carried out. This pharmaceutical injection preparatory operation involved checking the pharmaceutical injection days, the dose, and so forth on the basis of the pharmaceutical injection schedule prior to performing the pharmaceutical injection operation, correcting the dose, and so forth.

1-7. Pharmaceutical Injection Preparatory Operation 1-7-1. Overall Description of Pharmaceutical Injection Preparatory Operation The pharmaceutical injection preparatory operation performed by the pharmaceutical injection device in this embodiment will now be described. FIG. 15 is a flowchart of the pharmaceutical injection preparatory operation. FIGS. 16a to 16i are diagrams of display examples of the display component in the pharmaceutical injection device.

More specifically, when the power button 31 is pressed in S101, the starting screen shown in FIG. 16a is displayed on the display component 35 in S102 (S102 in FIG. 15). As shown in FIG. 16a, an example of a starting screen is a display on the display component 35 of the current time when the power button is pressed. As seen in FIG. 16a, today is Apr. 10, 2011, and the time is 10:15 in the morning.

Next, the pharmaceutical injection schedule is checked to see if injection is scheduled (S103 in FIG. 15).

At this point, as shown in the pharmaceutical injection schedule in FIG. 23, Apr. 9, 2011, is a Saturday, and the pharmaceutical injection schedule indicates no pharmaceutical injection that day. Therefore, as shown in FIG. 16b, a message of "No scheduled injection today" is displayed on the display component 35 (S104 in FIG. 15), and the power is switched off (S105 in FIG. 15).

If the day is a pharmaceutical injection day on the pharmaceutical injection schedule, then the controller 7 performs a comparison of the cumulative planned pharmaceutical dose up to the last time based on the pharmaceutical injection schedule preset by the physician, and the actual cumulative pharmaceutical dose up to the last time (also called the actual cumulative amount of pharmaceutical injected) (S106 in FIG. 15). Here, the cumulative planned pharmaceutical dose up to the last time based on the pharmaceutical injection schedule preset by the physician is what was initially set up by the physician, not what is on the pharmaceutical injection schedule reset by the pharmaceutical injection device (discussed below), so this will hereinafter also be referred to as the initial cumulative planned pharmaceutical dose.

That is, if the pharmaceutical has been injected according to the pharmaceutical injection schedule shown in FIG. 23, since the pharmaceutical injection results will have been recorded to the memory 46 as shown in FIG. 24, so as mentioned above, the controller 7 compares the cumulative planned pharmaceutical dose up to the last time based on the preset pharmaceutical injection schedule, with the actual cumulative pharmaceutical dose up to the last time. As shown in FIG. 24, in this example April 8 is scheduled for the injection of 1.00 mg of pharmaceutical, but the result for April 8 is recorded as 0 mg as a result of the user having skipped a pharmaceutical injection.

If the comparison by the controller 7 reveals that the cumulative planned pharmaceutical dose up to the last time based on the preset pharmaceutical injection schedule stored in the memory 46 is the same as the actual cumulative pharmaceutical dose up to the last time, that is, that the pharmaceutical has been injected as planned (from April 1 to April 7), then a message of "Ready for injection. Dose this time: 1.00 mg" is displayed on the display component 35 as shown in FIG. 16c (S107 in FIG. 15), and the device then goes into injection standby mode (S108 in FIG. 15).

Therefore, if the end button 34 is pressed in this state, air venting is performed, and if the pharmaceutical injection button 33 in FIG. 1 is then pressed, as discussed above, the needle insertion and retraction drive motor 12 will be driven, the injection needle 14 is inserted into the body, the piston drive motor 10 is driven in this state, and the above-mentioned 1.00 mg of pharmaceutical is injected. The air venting is an optional operation, and is carried out as needed. The air venting operation is also carried out as needed in the following embodiments.

After this injection, the needle insertion and retraction drive motor 12 and the piston drive motor 10 are driven in reverse to pull out the needle and retract the piston 5 from the pharmaceutical syringe 4.

Therefore, the patient removes the injection needle 14 from the pharmaceutical syringe 4, then pulls the pharmaceutical syringe 4 out of the pharmaceutical syringe mounting component 3, and puts it in a refrigerator. The next day, this pharmaceutical syringe 4 is again mounted to the pharmaceutical syringe mounting component 3, then the injection needle 14 is attached to the pharmaceutical syringe 4, and pharmaceutical injection is performed on the basis of that day's schedule.

In this pharmaceutical injection the next day, after the user has pressed the power button 31, and after the pharmaceutical injection preparatory operation in FIG. 15 has ended, and the pharmaceutical injection device has entered its injection standby mode (S108), the user presses the end button 34. Air venting is then performed as shown in FIG. 9. After this, the pharmaceutical injection button 33 is pressed to perform pharmaceutical injection according to that day's schedule. During this air venting, part of the pharmaceutical is squirted outside through the injection needle 14, so this squirt amount is factored into the schedule when setting the overall pharmaceutical dose mentioned above.

If an error occurs in the above-mentioned S106, that is, in the comparison of the cumulative planned pharmaceutical dose up to the last time based on the preset pharmaceutical injection schedule stored in the memory 46, and the actual cumulative pharmaceutical dose up to the last time (the user realized prior to the pharmaceutical injection on April 10 that he had skipped the pharmaceutical injection on April 8), then the controller 7 in S109 determines whether or not injection was skipped the last time. As discussed above, since the pharmaceutical injection results are recorded daily in the memory 46, whether or not the last injection was skipped can be determined from the pharmaceutical injection results stored in the memory 46.

If injection was skipped the last time, the controller 7 resets the future pharmaceutical injection schedule as shown in FIG. 25 in order to correct the dose related to the pharmaceutical injection this time (S110 and S111 in FIG. 15).

More specifically, when injection is started on Apr. 1, 2011, the initial cumulative planned pharmaceutical dose up to Apr. 8, 2011 (the last time before Apr. 10, 2011) is 7.00 mg. Meanwhile, the actual cumulative pharmaceutical dose from Apr. 1, 2011 until Apr. 8, 2011 is only 6.00 mg since the user skipped the injection on April 8. Therefore, there is a discrepancy between the initial cumulative planned pharmaceutical dose up to the last time and the actual cumulative pharmaceutical dose up to the last time, and control moves from S106 to S109. Since the user skipped the injection on Apr. 8, 2011, the pharmaceutical injection schedule is reset in S110 and S111. S110 and S111 will be discussed in detail below.

When the pharmaceutical injection schedule is reset, the buzzer 44 emits an alarm sound to notify the user that the pharmaceutical injection schedule has been reset (S112 in FIG. 15).

The controller 7 then determines whether or not the remainder obtained by subtracting the actual cumulative pharmaceutical dose up to the last time from the planned cumulative pharmaceutical dose up to the last time based on the pharmaceutical injection schedule preset by the physician is less than a specific value (S113 in FIG. 15).

If the remainder obtained by subtracting the actual cumulative pharmaceutical dose up to the last time from the planned cumulative pharmaceutical dose up to the last time based on the pharmaceutical injection schedule preset by the physician is less than a specific value, the controller 7 causes the display component 35 to give the display shown in FIG. 16d (S114 in FIG. 15). This S113 is provided in order to prompt the user in S115 to consult with a physician if the difference is great between the initial cumulative planned pharmaceutical dose and the actual cumulative pharmaceutical dose. This specific amount (allowable divergence) can be set to 1.50 mg, for example. This specific amount is varied as dictated by the type of pharmaceutical.

As shown in FIG. 16d, the display at this point is "Ready for injection," "Skipped injection," "Dose short by: 1.00 mg," "Extra 0.30 mg will be injected," and "Current dose: 1.30 mg," and since one injection was skipped, the display tells the user that the dose will be slightly higher this time, for example.

Therefore, if the pharmaceutical injection button 33 in FIG. 1 is pressed after the air venting operation, the needle insertion and retraction drive motor 12 is driven, the injection needle 14 is inserted into the body, the piston drive motor 10 is driven in this state, and 1.30 mg of pharmaceutical is injected on April 10 as shown in FIG. 25, on the basis of the reset pharmaceutical injection schedule. From April 11 onward, the pharmaceutical injection will be carried out according to this reset pharmaceutical injection schedule. Specifically, from April 11 to April 12, the above-mentioned 1.30 mg of pharmaceutical will be injected. On April 13, 1.10 mg of pharmaceutical will be injected. The calculation of these pharmaceutical doses will be discussed in detail in section 1-7-2, "Dose Correction Operation and Rescheduling Operation."

As discussed above, when pharmaceutical injection is performed subsequent to the resetting of the pharmaceutical injection schedule, on the injection days corrected from the initial planned pharmaceutical dose (such as April 11 to 13), in S106 there is a discrepancy between the initial cumulative planned pharmaceutical dose (see FIG. 23) and the actual cumulative pharmaceutical dose, so control proceeds to S109, but since pharmaceutical injection was performed the last time, control proceeds to S116. In S116, just as in S113, if the difference between the initial cumulative planned pharmaceutical dose and the actual cumulative pharmaceutical dose is greater than the allowable divergence, then after the display shown in FIG. 16e is given in S117, control proceeds to S118, a display similar to that in FIG. 16f is given, and the system switches to the injection standby mode of S108. A display that is similar to that in FIG. 16f is "Ready for injection," "Dose still short," "Dose short by: 0.70 mg," "Extra 0.30 mg will be injected," and "Current dose: 1.30 mg."

On the day when the initial pharmaceutical dose preset by the physician becomes the same as the injected dose (such as April 14), in S106 the actual cumulative pharmaceutical dose and the initial cumulative planned pharmaceutical dose are equal, so control proceeds to S107 and S108, and the pharmaceutical injection device enters the injection standby mode. The pharmaceutical injection preparatory operation from April 11 onward will be discussed in detail in section 1-7-3, "Pharmaceutical Injection Preparatory Operation from Schedule Resetting Onward."

In S113, if the remainder obtained by subtracting the actual cumulative pharmaceutical dose up to the last time from the planned cumulative pharmaceutical dose up to the last time based on the pharmaceutical injection schedule preset by the physician is at least a specific value, the controller 7 gives the display shown in FIG. 16e on the display component 35 (S115 in FIG. 15).

At this point, if two injections have been skipped, for example, the display is of "Cumulative dose is too low" and "Please consult a physician," as shown in FIG. 16e, and the controller 7 causes the display component 35 to display a message recommending consultation with a physician. For example, with the pharmaceutical injection schedule shown in FIG. 23, if injection has been skipped twice in a row, the actual cumulative pharmaceutical dose will be 2.00 mg short of the initial planned cumulative pharmaceutical dose, so in S113 the shortage will be greater than the 1.5 mg specific value, which is the allowable divergence, and control will proceed to S115.

However, since the pharmaceutical this time is a growth hormone, it is preferably injected without interruption, and at this point control proceeds to S114. In S114 the display shown in FIG. 16d is given, after which 1.30 mg of the pharmaceutical is injected.

Thus, when injection has been skipped two times, even in injection the next day control will proceed from S109 via S116 to S117, and the display in FIG. 16e will be given just as on the previous day. Control then proceeds to S118, and the display in FIG. 16f is given on the display component 35. To describe this in more specific terms, even through 1.30 mg of the pharmaceutical was injected on the last injection day, this only makes up for 0.3 mg of the shortage, so on the next injection day the actual cumulative pharmaceutical dose is still 1.70 mg short of the initial planned cumulative pharmaceutical dose. Accordingly, control proceeds from S109 to S116 and S117, and the display shown in FIG. 16e is given.

As shown in FIG. 16f, the display in S118 is "Ready for injection," "Dose still short," "Dose short by: 1.70 mg," "Extra 0.30 mg will be injected," and "Current dose: 1.30 mg," and again this time, the display indicates that the dosage will be increased slightly in order to make up for the amount that could not be made up for the last time (1.7 mg).

Thus, when injection is skipped, the schedule is updated so as to increase the next dose slightly in order to make up for the shortage, but if the injection has been skipped many times, it will take a long time to make up for this, so the user is urged to consult a physician.

In this embodiment, Saturday was a day of no injection, so this non-injection day may be used to update the schedule and make up the shortage in the dosage all at once.

1-7-2. Dose Correction Operation and Rescheduling Operation

1-7-2-1. Overview

Figure 17:
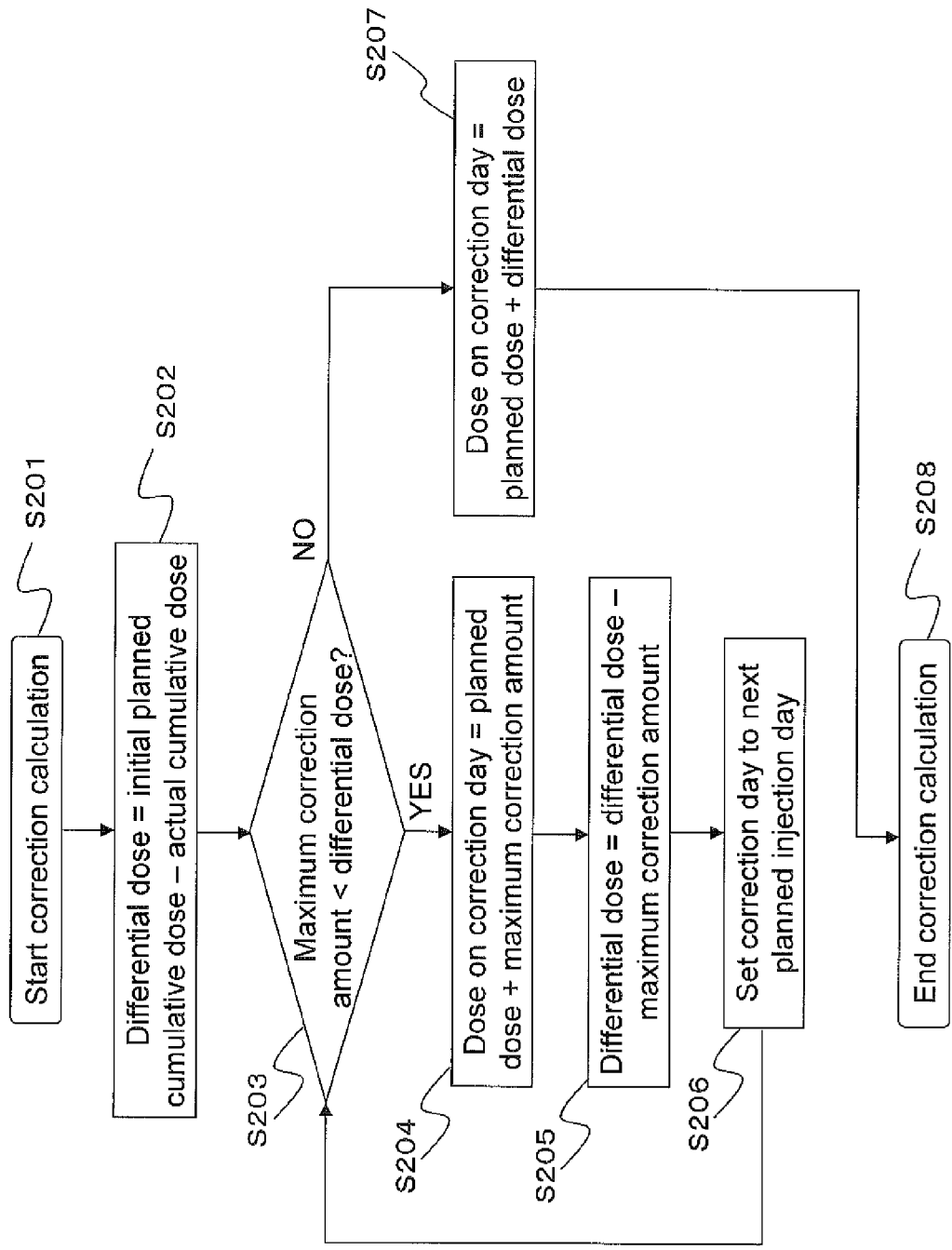
FIG. 17 is a flowchart of the operation of the pharmaceutical injection device pertaining to Embodiment 1 of the present invention.

Next, the pharmaceutical dose correction operation shown in S110 will be described. FIG. 17 illustrates in detail the dose correction of S110 in FIG. 15.

First, in S201, the controller 7 starts correction calculation. In this correction calculation, the remainder obtained by subtracting the actual cumulative pharmaceutical dose from the planned cumulative pharmaceutical dose (the initial planned cumulative pharmaceutical dose) based on the pharmaceutical injection schedule predetermined by a physician, is calculated as the differential dose (S202 in FIG. 17).

Then, the controller 7 calculates whether or not the differential dose is greater than the maximum correction amount (0.30 mg in this embodiment) (S203 in FIG. 17). If the differential dose is greater than the maximum correction amount (0.30 mg in this embodiment), then 1.30 mg is calculated as discussed above as the current dose on a correction day, using the formula of the planned pharmaceutical dose (1.00 mg in this embodiment)+the maximum correction amount (0.30 mg in this embodiment) (S204 in FIG. 17).

Next, in S205 the controller 7 sets the remainder obtained by subtracting the maximum correction amount from the differential dose as the new differential dose.

Next, in S206 the controller 7 sets the correction day as the next planned injection day.

The control flow then returns to S203, it is determined whether or not the newly set differential dose is greater than the maximum correction amount, and steps S203 to S206 are repeated until the differential dose is at or under the maximum correction amount.

In S203, if the differential dose is at or under the maximum correction amount (0.30 mg in this embodiment), the current dose is calculated to be 1.20 mg from the planned dose (1.00 mg in this embodiment)+the differential dose (such as 0.20 mg) (S207 in FIG. 17), and the correction calculation is ended (S208 in FIG. 17).

The result of the above operation is that when an injection is skipped, the pharmaceutical whose injection was skipped is allocated to other injection days so as not to exceed the maximum correction amount, and the corrected amount is calculated.

In S111, the corrected amount is factored into the reset schedule, which is stored in the memory 46. The pharmaceutical injection schedule preset by the physician is also stored in the memory 46.

1-7-2-2. Description by Specific Example

An example of the pharmaceutical injection schedule in FIG. 24 and data about pharmaceutical injection results will now be used to describe the above-mentioned dose correction operation in more specific terms.

As shown in FIG. 24, if the pharmaceutical injection is started on Apr. 1, 2011, the planned cumulative pharmaceutical dose up to Apr. 8, 2011 (the last time before Apr. 10, 2011) is 7.00 mg. On the other hand, because injection was skipped on April 8, the actual cumulative pharmaceutical dose from April 1 to Apr. 8, 2011 is 6.00 mg. Therefore, in S202 the differential dose is calculated as 1.0 mg.

Next, in S203, since the differential dose is 1.0 mg and is greater than the maximum correction amount (0.30 mg), control proceeds to S204. In S204, the corrected amount for the correction day (Apr. 10, 2011) is calculated as 1.30 mg.

Next, in S205, since the differential dose is 1.00 mg and the maximum correction amount is 0.30 mg, 0.70 mg is calculated as the new differential dose.

Then, in S206, the correction day is set to Apr. 11, 2011, which is the next planned injection day.

The control then returns to S203. Since the newly calculated differential dose is 0.70 mg, and the maximum correction amount is 0.30 mg, control proceeds to S204, and the correction amount for the correction day (Apr. 11, 2011) is calculated as 1.30 mg.

Next, in S205, since the differential dose is 0.70 mg and the maximum correction amount is 0.30 mg, 0.40 mg is calculated as the new differential dose. Then, in S206, the correction day is set to Apr. 12, 2011, which is the next planned injection day.

The control then returns to S203. Since the newly calculated differential dose is 0.40 mg, and the maximum correction amount is 0.30 mg, control proceeds to S204, and the correction amount for the correction day (Apr. 12, 2011) is calculated as 1.30 mg. Then, in S205, since the differential dose is 0.40 mg and the maximum correction amount is 0.30 mg, 0.10 mg is calculated as the new differential dose. Then, in S206, the correction day is set to Apr. 13, 2011, which is the next planned injection day.

Next, control returns to S203, but since the differential dose is 0.10 mg, which is less than the 0.30 mg that is the maximum correction amount, control moves on to S207. In S207 the correction amount for the correction day (Apr. 13, 2011) is calculated as the sum (1.10 mg) of the planned pharmaceutical dose (1.00 mg) and the differential dose (0.10 mg).

Next, control proceeds to S208, and the correction amount calculation operation ends. Specifically, as a result of this correction amount calculation operation, the planned pharmaceutical doses for April 10, 11, 12, and 13 are corrected to 1.30 mg, 1.30 mg, 1.30 mg, and 1.10 mg from the initial planned pharmaceutical doses set by the physician.

Then, in S111, the corrected planned pharmaceutical dose is used to reset the schedule as shown in FIG. 25, which is stored in the memory 46. The dose for the days after the days corrected from the initial planned pharmaceutical dose set by the physician do not differ from the initial planned pharmaceutical dose.

As discussed above, in a state in which a pharmaceutical injection schedule preset by a physician has been recorded to a memory, the pharmaceutical injection schedule reset by the controller 7 is recorded to the memory 46.

1-7-3. Pharmaceutical Injection Preparatory Operation After Schedule Resetting

A brief summary of the pharmaceutical injection preparatory operation on the planned pharmaceutical injection days following the resetting of the schedule was given above, but this shall now be described in detail by giving a specific example.

As discussed above, on Apr. 10, 2011 the pharmaceutical injection schedule shown in FIG. 25 was reset from the pharmaceutical injection schedule shown in FIG. 23 and preset by a physician, so on April 11 1.30 mg of the pharmaceutical is scheduled to be injected.

As shown in FIG. 15, if the patient switches on the power to the pharmaceutical injection device (S101) on April 11, which is a planned injection day after the resetting of the schedule, control proceeds to S102, S103, and S106.

In S106, it is determined whether or not the planned cumulative pharmaceutical dose based on the pharmaceutical injection schedule preset by the physician is the same as the actual cumulative pharmaceutical dose. Here, the actual cumulative pharmaceutical dose up to the last time before April 11 (April 10) is 7.30 mg. Meanwhile, the initial planned cumulative pharmaceutical dose is 8.00 mg on the pharmaceutical injection schedule in FIG. 24. Thus, the actual cumulative pharmaceutical dose is not the same as the initial planned cumulative pharmaceutical dose, so control proceeds to S109.

Next, in S109 it is determined by the controller 7 whether or not the injection was skipped the last time. If injection was not skipped the last time before April 11 (April 10), control proceeds to S116. Then, in S116, if the remainder obtained by subtracting the actual cumulative pharmaceutical dose up to the last time from the planned cumulative pharmaceutical dose up to the last time is at or above a specific value, in S117 the controller 7 causes the display component 35 to give the display shown in FIG. 16e, and a message recommending consultation with a physician is displayed. Prior to the pharmaceutical injection on April 11, the actual cumulative pharmaceutical dose was 7.30 mg, as mentioned above, and the initial planned cumulative pharmaceutical dose was 8.00 mg, so the difference between the two is 0.70 mg, which is less than the 1.50 mg that is the allowable divergence. Therefore, control does not proceed to S117, and instead proceeds from S116 to S118, and a display similar to that in FIG. 16f is given. More specifically, the displayed messages are "Ready for injection," "Dose still short," "Dose short by: 0.70 mg," "Extra 0.30 mg will be injected," and "Current dose: 1.30 mg."

Control then proceeds to S108, and the pharmaceutical injection device goes into injection standby mode. When air venting is performing in this state and the pharmaceutical injection button 33 is pressed, the injection of 1.30 mg of pharmaceutical is executed on the basis of the pharmaceutical injection schedule reset on April 10 (see FIG. 25).

In the pharmaceutical injection on April 12, messages of "Ready for injection," "Dose still short," "Dose short by: 0.40 mg," "Extra 0.30 mg will be injected," and "Current dose: 1.30 mg" are given, and 1.30 mg of pharmaceutical is injected.

In the pharmaceutical injection on April 13, messages of "Ready for injection," "Dose still short," "Dose short by: 0.10 mg," "Extra 0.10 mg will be injected," and "Current dose: 1.10 mg" are given, and 1.10 mg of pharmaceutical is injected.

As shown in FIG. 25, in the pharmaceutical injection on April 14, the actual cumulative pharmaceutical dose up to the last time is 11.00 mg, and the planned cumulative pharmaceutical dose initially set up to the last time is 11.00 mg, so control proceeds to S107, the display of "Ready for injection. Current dose: 1.00 mg" shown in FIG. 16c is given, and the pharmaceutical injection device enters its injection standby mode (S108).

As discussed above, the pharmaceutical injection device in this embodiment is such that even if pharmaceutical injection cannot be performed according to the pharmaceutical injection schedule set by a physician, such as when the user skips an injection, the pharmaceutical injection schedule can be reset automatically, so the user does not have to visit a physician to have the pharmaceutical injection schedule reset, which makes the device more convenient to use.

Furthermore, in Embodiment 1, the description was of resetting the pharmaceutical injection schedule from a pharmaceutical injection schedule preset by a physician, but if an injection is skipped while following a reset pharmaceutical injection schedule, further resetting is performed according to the control flow in FIGS. 15 and 17. This further resetting is executed even if pharmaceutical injection was skipped during the corrected injection period for the reset pharmaceutical dose (the period of a dose that differs from the pharmaceutical dose set by the physician, such as the period from April 11 to April 13 in FIG. 25). In this case, the pharmaceutical injection schedule reset by the controller 7 may be updated to the further reset pharmaceutical injection schedule and deleted from the memory 46, but the pharmaceutical injection schedule set by the physician will remain stored in the memory 46.

Embodiment 2

FIGS. 18 to 22 show the control flow in Embodiment 2 of the present invention. In Embodiment 2, those components shown in FIGS. 1 to 9 and used in Embodiment 1 above are exactly the same, and therefore will not be described again.

To give a brief summary of the pharmaceutical injection device in Embodiment 2, a pharmaceutical can be injected with the pharmaceutical injection device of Embodiment 2 even on days other than the planned pharmaceutical injection days set by a physician, and when pharmaceutical injection is performed on a day other than a planned injection day, control is performed to reset the pharmaceutical injection schedule.

2-1. Pharmaceutical Injection Schedule

In Embodiment 2, a different operation is performed from that in Embodiment 1 above, and to this end the operating program thereof is stored in the controller 7, and particularly in the ROM 38, in FIG. 3. More specifically, in Embodiment 2, the pharmaceutical contained in the pharmaceutical syringe 4 is injected, for example, on Monday, Tuesday, Wednesday, Thursday, and Friday during a week, with Saturday and Sunday set as non-injection days.

The pharmaceutical injection schedule here is set by a physician, as are the pharmaceutical injection days and doses. This pharmaceutical injection schedule is stored in the memory 46 in FIG. 3, as a pharmaceutical injection schedule that has been preset by a physician. FIG. 26 shows the pharmaceutical injection schedule preset by a physician in Embodiment 2. With the pharmaceutical injection schedule shown in FIG. 26, as mentioned above, Monday, Tuesday, Wednesday, Thursday, and Friday are injection days, while Saturday and Sunday are non-injection days. The daily pharmaceutical dose is set at 1.00 mg. At the point of Mar. 31, 2011, no pharmaceutical injection has been performed.

As a result, the control program stored in the ROM 38 executes the subsequent operation while referring to the pharmaceutical injection schedule stored in the memory 46.

Figure 18:
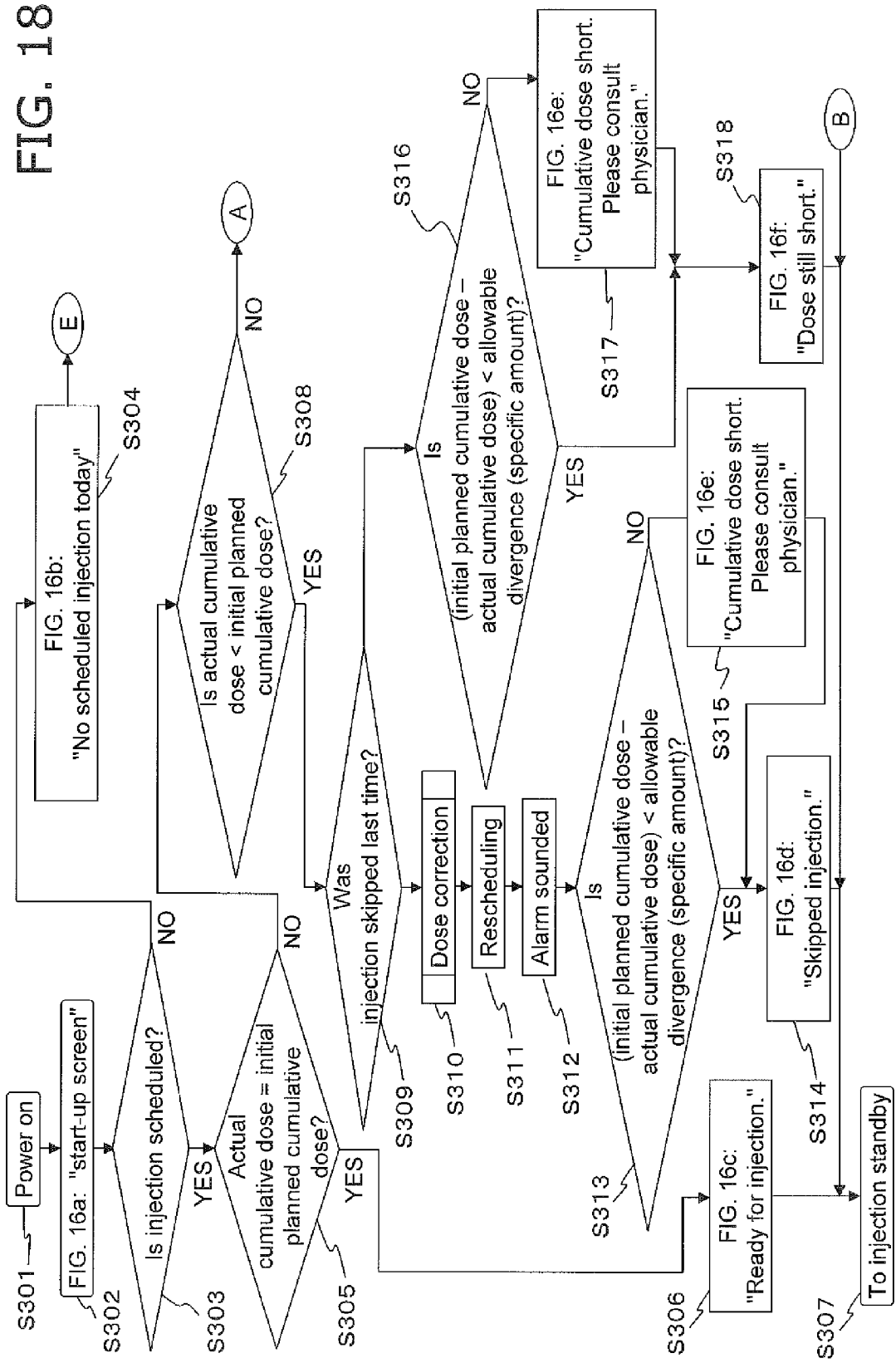
FIG. 18 is a flowchart of the operation of the pharmaceutical injection device pertaining to Embodiment 2 of the present invention.

Therefore, as shown in FIGS. 1 and 2, when the power button 31 is pressed in a state in which the pharmaceutical syringe 4 has been mounted to the pharmaceutical syringe mounting component 3 (S301 in FIG. 18), the pharmaceutical injection preparatory operation shown in FIG. 18 is carried out. This pharmaceutical injection preparatory operation checks the pharmaceutical injection days, dose, and so forth on the basis of the pharmaceutical injection schedule prior to performing the pharmaceutical injection operation, corrects the pharmaceutical dose, and performs other such operations.

2-2. Pharmaceutical Injection Preparatory Operation 2-2-1. Overall Description of Pharmaceutical Injection Preparatory Operation The pharmaceutical injection preparatory operation in the pharmaceutical injection device of this embodiment will now be described. FIG. 18 shows the control flow of the pharmaceutical injection preparatory operation.

More specifically, when the power button 31 is pressed in S301, the start-up screen shown in FIG. 16a is disposed on the display component 35 (S302 in FIG. 18). As shown in FIG. 16a, as an example of a start-up screen, the date and time at which the power button was pressed (such as 10:15 on Apr. 9, 2011) are displayed on the display component 35.

Next, whether or not there is a planned injection according to the pharmaceutical injection schedule is confirmed (S303 in FIG. 18).

At this point, since Apr. 9, 2011 is a Saturday, as shown in the pharmaceutical injection schedule in FIG. 26, no pharmaceutical injection is planned on the pharmaceutical injection schedule. Therefore, as shown in FIG. 16b, the message "No injection scheduled today" is displayed on the display component 35 (S304 in FIG. 18).

Figure 19:
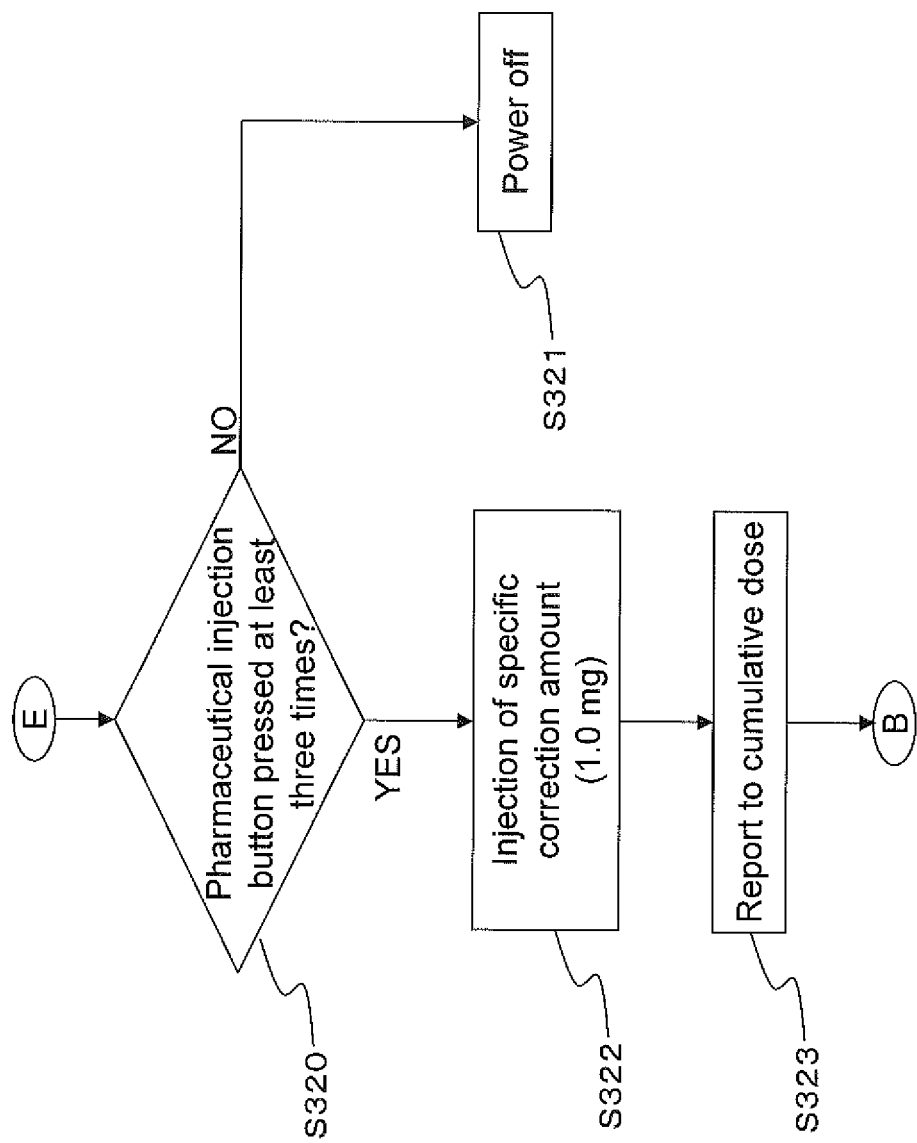
FIG. 19 is a flowchart of the operation of the pharmaceutical injection device pertaining to Embodiment 2 of the present invention.

Next, the controller 7 determines whether or not the pharmaceutical injection button 33 has been pressed at least three times (S320 in FIG. 19), and if the pharmaceutical injection button 33 has not been pressed at least three times, the power supply is switched off (S321 in FIG. 19). If the pharmaceutical injection button 33 has been pressed at least three times, control proceeds to S322 and S323. This operation will be discussed in detail below. FIG. 19, as discussed in detail below, shows the control flow of the operation for performing pharmaceutical injection other than on planned injection days.

As shown in FIG. 26, Monday of the next week is a pharmaceutical injection day on the pharmaceutical injection schedule, so when the power button 31 is pressed, control proceeds to S301, S302, S303, and S305. In S305 the controller 7 compares the actual cumulative pharmaceutical dose up to the last time with the planned cumulative pharmaceutical dose up to the last time on the basis of the pharmaceutical injection schedule stored in the memory 46 and preset by a physician (S305 in FIG. 18).

If this comparison reveals that the actual cumulative pharmaceutical dose up to the last time with the planned cumulative pharmaceutical dose up to the last time on the basis of the preset pharmaceutical injection schedule stored in the memory 46 are the same, that is, that the pharmaceutical has been injected according to schedule, then messages of "Ready for injection" and "Dose this time: 1.00 mg" are displayed on the display component 35 as shown FIG. 16c (S306 in FIG. 18), and the device then enters its injection standby mode (S307 in FIG. 18).

Therefore, when air venting is performed in this state and the pharmaceutical injection button 33 in FIG. 1 is pressed, as discussed above, the needle insertion and retraction drive motor 12 is driven, the injection needle 14 is inserted into the body, the piston drive motor 10 is driven in this state, and the above-mentioned 1.00 mg of pharmaceutical is injected.

After this injection, the needle insertion and retraction drive motor 12 and the piston drive motor 10 are driven in reverse to pull out the needle and retract the piston 5 from the pharmaceutical syringe 4.

Therefore, the patient removes the injection needle 14 from the pharmaceutical syringe 4, then pulls the pharmaceutical syringe 4 out of the pharmaceutical syringe mounting component 3 and stores it in a refrigerator. The next day, the pharmaceutical syringe 4 is again mounted to the pharmaceutical syringe mounting component 3, then the injection needle 14 is attached to the pharmaceutical syringe 4, and the pharmaceutical is injected according to the schedule for that day.

In this pharmaceutical injection the next day, after the patient has pressed the power button 31 and the pharmaceutical injection preparatory operation shown in FIG. 18 is ended, the pharmaceutical injection device goes into injection standby (S307), after which the user presses the end button 34. This results in the air venting shown in FIG. 9. After this, the user presses the pharmaceutical injection button 33 to perform pharmaceutical injection according to the schedule for that day. During this air venting, part of the pharmaceutical is squirted out through the injection needle 14, so this squirted amount is taken into account in setting the above-mentioned total pharmaceutical doses on the schedule.

In the above-mentioned S305, that is, in the comparison of the cumulative planned pharmaceutical dose up to the last time based on the preset pharmaceutical injection schedule stored in the memory 46, and the actual cumulative pharmaceutical dose up to the last time, if there is a discrepancy, the controller 7 determines whether or not the actual cumulative pharmaceutical dose is less than the planned cumulative pharmaceutical dose (S308 in FIG. 18). If this determination is that the actual cumulative pharmaceutical dose is less than the planned cumulative pharmaceutical dose, the controller 7 determines in S309 whether or not the pharmaceutical injection was skipped the last time. Since the pharmaceutical injection results are recorded as mentioned above in the memory 46 on a daily basis, whether or not the last pharmaceutical injection was skipped can be determined from the pharmaceutical injection results stored in the memory 46.

If injection was skipped the last time, the controller 7 corrects the dose related to the current pharmaceutical injection, and resets the future pharmaceutical injection schedule (S310 and S311 in FIG. 18). These steps S310 and S311 will be discussed in detail below.

More specifically, if the pharmaceutical injection results and the pharmaceutical injection schedule in FIG. 27 indicate that injection was started on Apr. 1, 2011, the initial planned cumulative pharmaceutical dose up to Apr. 8, 2011 (the last time before Apr. 11, 2011) is 6.00 mg. On the other hand, because injection was skipped on April 8, the actual cumulative pharmaceutical dose from April 1 to Apr. 8, 2011 is 5.00 mg. Accordingly, there is a discrepancy between the initial planned cumulative pharmaceutical dose up to the last time and the actual cumulative pharmaceutical dose up to the last time, and control proceeds from S305 to S308. Since the actual cumulative pharmaceutical dose up to the last time is less than the initial planned cumulative pharmaceutical dose up to the last time, control proceeds to S309, and because injection was skipped the last time (Apr. 8, 2011), the future pharmaceutical injection schedule is reset (S310, S311).

When the pharmaceutical injection schedule is reset, an alarm sound is emitted from the buzzer 44 to notify the user that the pharmaceutical injection schedule has been reset (S312 in FIG. 18).

The controller 7 then determines whether or not the remainder obtained by subtracting the actual cumulative pharmaceutical dose up to the last time from the planned cumulative pharmaceutical dose up to the last time based on the pharmaceutical injection schedule preset by the physician is less than a specific value (S313 in FIG. 18).

If the remainder obtained by subtracting the actual cumulative pharmaceutical dose up to the last time from the planned cumulative pharmaceutical dose up to the last time based on the pharmaceutical injection schedule preset by the physician is less than a specific value (allowable divergence), the controller 7 causes the display component 35 to give the display shown in FIG. 16d (S314 in FIG. 18). This step S313 is provided in order to recommend consultation with a physician if the difference is great between the initial cumulative planned pharmaceutical dose and the actual cumulative pharmaceutical dose, and this allowable divergence can be set at 1.50 mg, for example. This value can be suitably changed as dictated by the type of pharmaceutical.

As shown in FIG. 16d, the display at this point is "Ready for injection," "Skipped injection," "Dose short by: 1.00 mg," "Extra 0.30 mg will be injected," and "Current dose: 1.30 mg," and since one injection was skipped, the display tells the user that the dose will be slightly higher this time, for example.

Therefore, if the pharmaceutical injection button 33 in FIG. 1 is pressed in this state, the needle insertion and retraction drive motor 12 is driven, the injection needle 14 is inserted into the body, the piston drive motor 10 is driven in this state, and the above-mentioned 1.30 mg of pharmaceutical is injected.

In S313, if the remainder obtained by subtracting the actual cumulative pharmaceutical dose up to the last time from the planned cumulative pharmaceutical dose up to the last time based on the pharmaceutical injection schedule preset by the physician is less than a specific value (allowable divergence), the controller 7 causes the display component 35 to give the display shown in FIG. 16e (S315 in FIG. 18).

At this point, if injection has been skipped twice, for example, the display is of "Cumulative dose is too low" and "Please consult a physician," as shown in FIG. 16e, and the controller 7 causes the display component 35 to display a message recommending consultation with a physician. For example, with the pharmaceutical injection schedule shown in FIG. 26, if injection has been skipped twice, the actual cumulative pharmaceutical dose will be 2.00 mg short of the initial planned cumulative pharmaceutical dose, so in S313 the shortage will be greater than the 1.5 mg specific value, which is the allowable divergence, and control will proceed to S315.

However, since the pharmaceutical this time is a growth hormone, it is preferably injected without interruption, and at this point control proceeds to S314. In S314 the display shown in FIG. 16d is given, after which control proceeds to S307, and 1.30 mg of the pharmaceutical is injected. Control may also be performed so that the operation is halted without recommending uninterrupted injection.

As discussed above, when injection has been skipped two times, in injection the next day control will proceed from S301 via S316 to S317, and the display in FIG. 16e will be given just as on the previous day. Control then proceeds to S318, and the display in FIG. 16f is given on the display component 35. For example, even through 1.30 mg of the pharmaceutical was injected on the last injection day, this only makes up for 0.3 mg of the shortage, so on the next injection day the actual cumulative pharmaceutical dose is still 1.70 mg short of the initial planned cumulative pharmaceutical dose. Accordingly, control proceeds from S309 to S316, the display shown in FIG. 16e is given, and then control proceeds to S317, and the display shown in FIG. 16f is given.

As shown in FIG. 16f, the display here is "Ready for injection," "Dose still short," "Dose short by: 1.70 mg," "Extra 0.30 mg will be injected," and "Current dose: 1.30 mg," and again this time, the display indicates that the dosage will be increased slightly in order to make up for the amount that could not be made up for the last time (1.7 mg).

Thus, when injection is skipped, the schedule is updated so as to increase the next dose slightly in order to make up for the shortage, but if the injection has been skipped many times, it will take a long time to make up for this, so the user is urged to consult a physician.

In Embodiment 2, Saturday and Sunday were days of no injection, so these non-injection days may be used to update the schedule and make up the shortage in the dosage all at once.

2-2-2. Dose Correction Operation and Rescheduling Operation after Skipped Injection 2-2-2-1. Overview Next, the pharmaceutical dose correction operation shown in S310 will be described.

Figure 20:
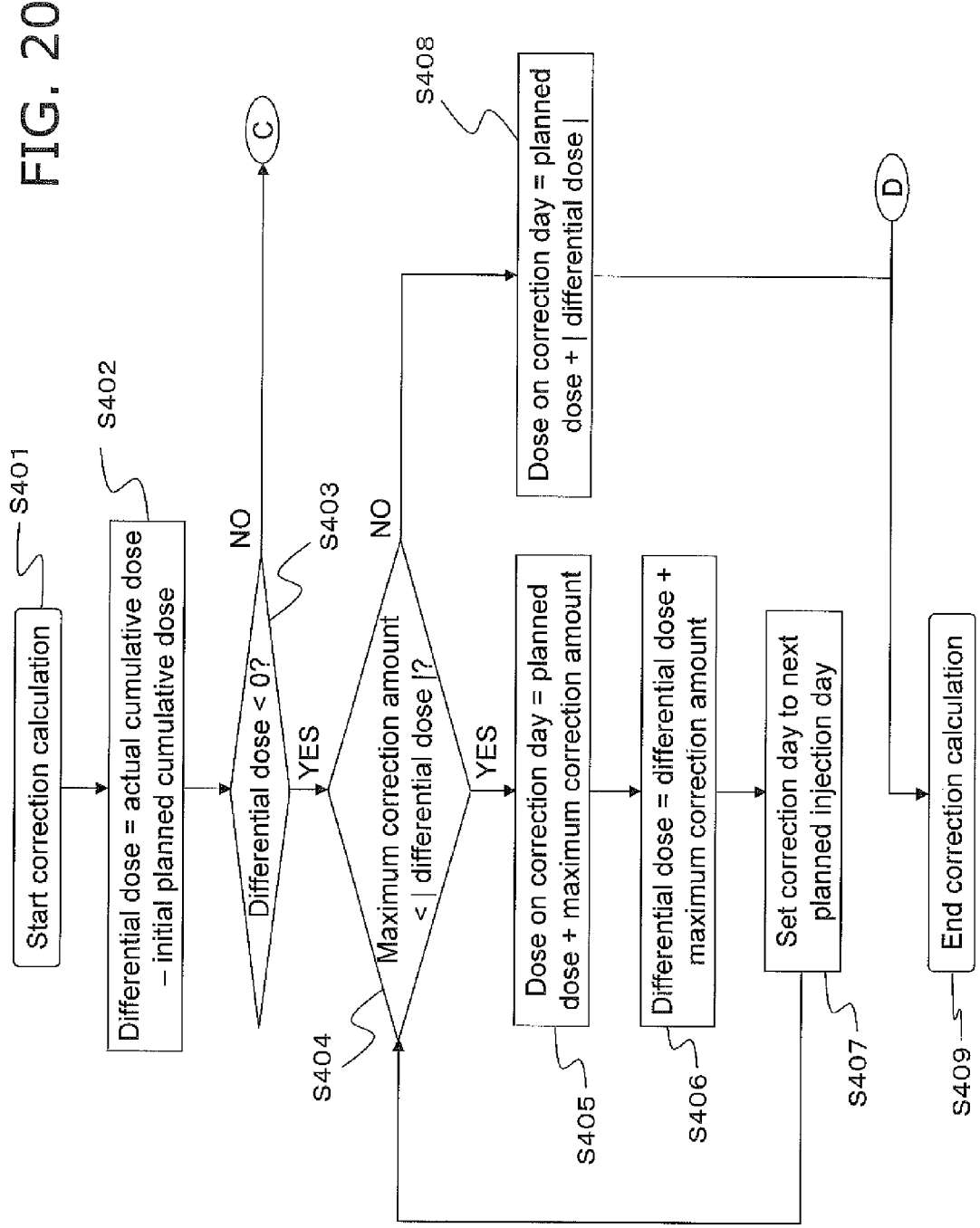
FIG. 20 is a flowchart of the operation of the pharmaceutical injection device pertaining to Embodiment 2 of the present invention.
Figure 21:
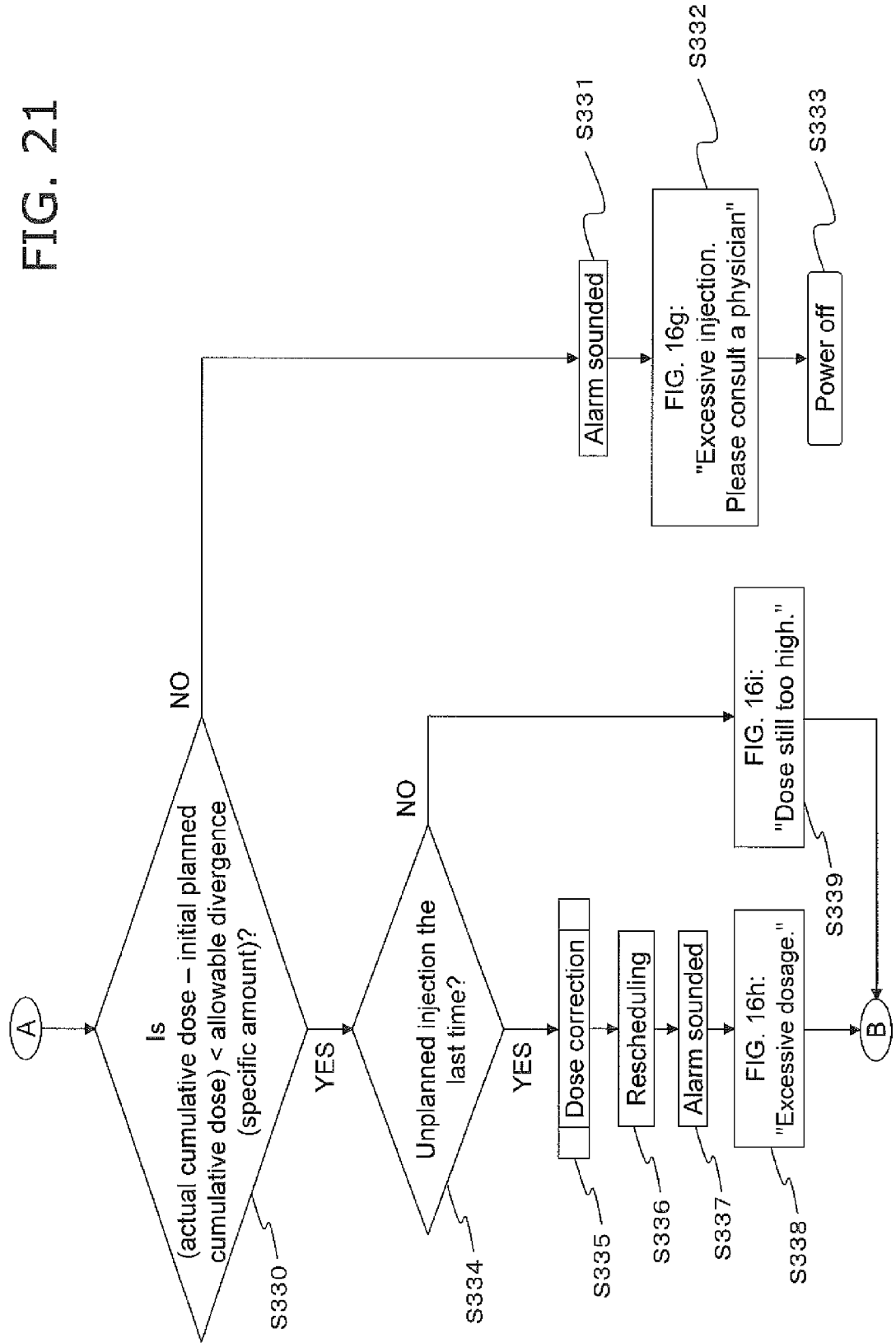
FIG. 21 is a flowchart of the operation of the pharmaceutical injection device pertaining to Embodiment 2 of the present invention.

FIG. 20 illustrates in detail the dose correction of S310 in FIG. 18 and part of step S335 in FIG. 21. FIG. 27 is a diagram of an initial pharmaceutical injection schedule determined by a physician and pharmaceutical injection results, and FIG. 28 is a diagram of a reset pharmaceutical injection schedule.

First, in S401, the controller 7 starts correction calculation. In this correction calculation, the remainder obtained by subtracting the planned cumulative pharmaceutical dose based on the pharmaceutical injection schedule predetermined by a physician from the actual cumulative pharmaceutical dose is calculated as a differential dose (S202 in FIG. 17).

In S308 in FIG. 18, if the actual cumulative pharmaceutical dose is less than the initial planned cumulative pharmaceutical dose, that is, if injection has been skipped, control proceeds to S309 and S310, and then proceeds to S401, S402, S403, and S404 in FIG. 20. Specifically, in S402, since the differential dose is found by subtracting the initial planned cumulative pharmaceutical dose from the actual cumulative pharmaceutical dose, if injection has been skipped, the differential dose will be a negative value. Accordingly, in the subsequent step S403, control proceeds to S404. In S404 it is determined whether or not the absolute value of the differential dose is greater than the maximum correction amount (0.30 mg in this embodiment).

If the absolute value of this differential dose is greater than the maximum correction amount (0.30 mg in this embodiment), then the current dose (the dose for today, which is a correction day) is calculated by using the formula of the planned pharmaceutical dose (1.00 mg in this embodiment)+the maximum correction amount (0.30 mg in this embodiment). As discussed above, 1.30 mg is calculated as the dose for today (S405 in FIG. 20).

Then, in S406, the controller 7 calculates the sum of adding the maximum correction amount to the differential dose as the new differential dose.

Then, in S407, the controller 7 sets the correction day as the next planned injection day.

The control then returns to S404, in which it is determined whether or not the absolute value of the newly calculated differential dose is greater than the maximum correction amount, and steps S404 to S407 are repeated until the absolute value of the differential dose is at or under the maximum correction amount.

In S404, if this differential dose is at or under the maximum correction amount (0.30 mg in this embodiment), then the dose for today is calculated as the planned dose (1.00 mg in this embodiment)+the absolute value of the differential dose (such as 0.20 mg), which gives 1.20 mg (S408 in FIG. 20), and the correction calculation is ended (S409 in FIG. 20).

As a result of the above operation, if injection has been skipped, then the amount of pharmaceutical corresponding to the skipped injection is allocated to another injection day or days so as not to exceed the maximum correction amount, and the correction amount is calculated.

In S311 (see FIG. 18), the correction amount is included in the resetting of the schedule, which is stored in the memory 46.

2-2-2-2. Specific Example

The above-mentioned dose correction operation will now be described in more detail by giving an example of the pharmaceutical injection schedule in FIG. 27 and of data for pharmaceutical injection results.

As shown in FIG. 27, when injection is started on Apr. 1, 2011, the initial cumulative planned pharmaceutical dose up to Apr. 8, 2011 (the last time before Apr. 11, 2011) is 6.00 mg. Meanwhile, the actual cumulative pharmaceutical dose from Apr. 1, 2011 until Apr. 8, 2011 is only 5.00 mg since the user skipped the injection on April 8. Therefore, the differential dose is calculated as −1.0 mg in S402.

Then, in S403, since the differential dose is −1.0 mg, control proceeds to S404.

Then, in S404, since the differential dose is −1.0 mg and the absolute value of the differential dose (1.0 mg) is greater than the maximum correction amount (0.30 mg), control proceeds to S405. In S405, since the planned dose is 1.0 mg and the maximum correction amount is 0.30 mg, the correction amount on the correction day (Apr. 11, 2011) is calculated as 1.30 mg using the formula of the planned dose+the maximum correction amount.

Then, in S406, since the differential dose is −1.0 mg and the maximum correction amount is 0.30 mg, −0.70 is calculated as the new differential dose.

Then, in S407, the correction day is set to Apr. 12, 2011, which is the next planned injection day.

Control then returns to S404. Since the newly calculated differential dose is −0.70 mg and the maximum correction amount is 0.30 mg, control proceeds to S405, and the correction amount for the correction day (Apr. 12, 2011) is calculated as 1.30 mg.

Then, in S406, since the differential dose is −0.70 mg and the maximum correction amount is 0.30 mg, −0.40 mg is calculated as the new differential dose. Then, in S407, the correction day is set to Apr. 13, 2011, which is the next planned injection day.

The control then returns to S404. Since the newly calculated differential dose is −0.40 mg and the maximum correction amount is 0.30 mg, control proceeds to S405, and 1.30 mg is calculated as the correction amount for the correction day (Apr. 13, 2011). Then, in S406, since the differential dose is −0.40 mg and the maximum correction amount is 0.30 mg, −0.10 mg is calculated as the new differential dose. Then, in S406, the correction day is set to Apr. 14, 2011, which is the next planned injection day.

The control then returns to S404, but since the differential dose is −0.10 mg, the absolute value thereof is less than the maximum correction amount (0.30 mg), and control proceeds to S408. Then, in S408, the correction amount for the correction day (Apr. 14, 2011) is calculated as the sum (1.10 mg) of the planned dose (1.00 mg) and the absolute value (0.10 mg) of the differential dose (−0.10 mg).

Then, control proceeds to S409, and the correction calculation operation is ended. Specifically, the result of this correction calculation operation is that the planned doses for April, 11, 12, 13, and 14 are respectively corrected as 1.30 mg, 1.30 mg, 1.30 mg, and 1.10 mg.

Then, in S311 (see FIG. 18), the corrected planned dose is used to reset the schedule as shown in FIG. 28, and this schedule is stored in the memory 46. The dose on days other than the correction days is the same as the dose on the reset schedule. The pharmaceutical injection schedule set by the physician (see FIG. 25) is also stored in the memory 46.

2-2-3. Unplanned Injection Operation

We will now describe a case in which a pharmaceutical is to be injected on a Saturday, on which is no pharmaceutical injection is planned.

This scenario could include, for example, a situation in which injection could not be performed on a Monday, such as when the patient was travelling. If this happens, the patient turns on the power button 31 (S301 in FIG. 18), whereupon it is determined in S303, via S302, whether or not it is a planned injection day. In this case, since it is a Saturday, control proceeds from S303 to S320 in FIG. 19, via S304, and the operations are carried out successively.

Here, if the patient presses the pharmaceutical injection button 33 three or more times, the controller 7 executes the injection of 1.0 mg of the pharmaceutical as the specific correction amount. As a result, the cumulative dose of 1.0 mg is stored in the memory 46 (S322 and S323 in FIG. 19).

Also, even though the pharmaceutical was thus injected on a Saturday, on which no pharmaceutical injection was planned, if the patient tries to inject the pharmaceutical again on Sunday by turning on the power button 31 on Sunday (S301 in FIG. 18), it will again be determined in S303, via S302, whether or not it is a planned injection day. At this point a message of "No injection planned for today" is displayed on the display screen 35, but if the patient presses the pharmaceutical injection button 33 three or more times, the controller 7 will execute the injection of 1.0 mg of pharmaceutical (1.0 mg pharmaceutical injection). As a result, the cumulative dose will be stored as the current pharmaceutical dose of a total of 2.0 mg, which is obtained by adding the 1.0 mg for today (Sunday) to the 1.0 mg of the yesterday (Saturday) (S322 and S323 in FIG. 19).

In this state, if the patient turns on the power button 31 in an attempt to inject the pharmaceutical on Monday (S301 in FIG. 18), it will again be determined in S303, via S302, whether or not it is a planned injection day. Since this Monday is a planned injection day, control proceeds to S305, and the controller 7 compares the initial planned cumulative pharmaceutical dose up to the last time stored in the memory 46 with the actual cumulative pharmaceutical dose up to the last time (S305 in FIG. 18).

In this case, as discussed above, since pharmaceutical injection was performed on Saturday and Sunday, which are not planned injection days, control proceeds to S308. In S308, since the actual cumulative pharmaceutical dose is greater than the initial planned cumulative pharmaceutical dose, control proceeds to S330 in FIG. 21.

In S330, the controller 7 determines whether or not the remainder obtained by subtracting the initial planned cumulative pharmaceutical dose from the actual cumulative pharmaceutical dose up to the last time is less than a specific amount (allowable divergence). The specific value in S330 here is 1.5 mg, so as discussed above, if a total pharmaceutical injection of 2.0 mg was performed on Saturday and Sunday, control proceeds to S331, and an alarm sound is emitted from the buzzer 44. This specific amount (allowable divergence) is provided in order to recommend consultation with a physician if there is a large difference between the planned cumulative pharmaceutical dose and the actual cumulative pharmaceutical dose, and is set to 1.50 mg in this embodiment, but may be suitably changed as dictated by the type of pharmaceutical.

Then, in S332, the controller 7 causes the display component 35 to display "Excessive injection" and "Please consult a physician" as shown in FIG. 16g, and the power is shut off in S333.

We will now describe a case in which, unlike in this example, 1.0 mg of pharmaceutical was injected only on Saturday, as discussed above. FIG. 29 is a diagram of a pharmaceutical injection schedule determined by a physician, and pharmaceutical injection results.

As shown in FIG. 29, when 1.0 mg of pharmaceutical is injected only on Saturday, and the patient turns on the power button 31 in an attempt to inject the pharmaceutical on Monday, control proceeds to S305 via S301, S302, and S303 in FIG. 18. In S305, the controller 7 compares the planned cumulative pharmaceutical dose up to the last time based on the pharmaceutical injection schedule set by the physician, with the actual cumulative pharmaceutical dose up to the last time.

In this case, since an unplanned 1.0 mg of pharmaceutical was injected on Saturday, control proceeds to S308, and in S308, since the actual cumulative pharmaceutical dose is greater than the planned cumulative pharmaceutical dose, control proceeds to S330 in FIG. 21. In S330, the controller 7 determines whether or not the remainder obtained by subtracting the planned cumulative pharmaceutical dose up to the last time based on the pharmaceutical injection schedule predetermined by the physician from the actual cumulative pharmaceutical dose up to the last time is less than a specific value (allowable divergence).

As mentioned above, since the specific value (allowable divergence) in S330 is 1.5 mg, when 1.0 mg of pharmaceutical is injected only on Saturday, since this amount is less than the specific value, control proceeds to S334. In S334 it is determined whether or not injection was performed outside the planned previous times. Since injection was performed on Saturday, that means that injection was performed outside the planned previous times as of the pharmaceutical injection on Monday, and the controller 7 resets a future pharmaceutical injection schedule in order to perform dose correction related to the current pharmaceutical injection (S335 and S336 in FIG. 21). Steps S335 and S336 will be discussed in detail below.

When the pharmaceutical injection schedule is reset, the buzzer 44 emits an alarm sound to notify the user that the pharmaceutical injection schedule has been reset (S337 in FIG. 21).

The control then proceeds to S338 and causes the display in FIG. 16h to be given on the display component 35. More specifically, the display component 35 displays "Ready for injection," "Excessive dosage," "Dose too high by: 1.00 mg," "0.30 mg less will be injected," and "Current dose: 0.70 mg," and in this state control proceeds to S307 in FIG. 18.

That is, in this state, if air venting is performed and the pharmaceutical injection button 33 in FIG. 1 is pressed, the needle insertion and retraction drive motor 12 is driven, the injection needle 14 is inserted into the body, the piston drive motor 10 is driven in this state, and the above-mentioned 0.70 mg of pharmaceutical is injected. The calculation of this 0.70 mg will be discussed in detail below.

In this state, if the patient turns on the power button 31 the next day (Tuesday) in order to perform pharmaceutical injection according to schedule, the control switches to S305, via S301, S302, and S303 in FIG. 18. At this point, since 1.00 mg was injected on Saturday, which was unplanned, as mentioned above, the dose for Monday was reduced by 0.30 mg from 1.0 mg to 0.70 mg, but this still leaves an excess injection of 0.70 mg. Therefore, on Tuesday, control proceeds to S308, S330, and S334. However, since the pharmaceutical injection on the previous day (Monday) was unplanned, control proceeds to S339, and the controller 7 causes the display component 35 to give the display shown in FIG. 16i.

More specifically, the display component 35 displays "Ready for injection," "Dose still too high," "Dose too high by: 0.70 mg," "0.30 mg less will be injected," and "Current dose: 0.70 mg," and in this state, control proceeds to S307 in FIG. 18, and the devices goes into injection standby mode. That is, in this state, when the pharmaceutical injection button 33 in FIG. 1 is pressed after air venting, as discussed above, the needle insertion and refraction drive motor 12 is driven, the injection needle 14 is inserted into the body, the piston drive motor 10 is driven in this state, and the above-mentioned 0.70 mg of pharmaceutical is injected.

The same operation as on Tuesday is then carried out on Wednesday, with 0.70 mg of pharmaceutical being injected.

However, on Wednesday the display component 35 displays "Ready for injection," "Dose still too high," "Dose too high by: 0.40 mg," "0.30 mg less will be injected," and "Current dose: 0.70 mg," and in this state, control proceeds to S307 in FIG. 18. That is, in this state, when the pharmaceutical injection button 33 in FIG. 1 is pressed after air venting, as discussed above, the needle insertion and retraction drive motor 12 is driven, the injection needle 14 is inserted into the body, the piston drive motor 10 is driven in this state, and the above-mentioned 0.70 mg of pharmaceutical is injected.

Then, on Thursday the operation as on Wednesday is performed, and 0.90 mg of pharmaceutical is injected. However, on Thursday the display component 35 displays "Ready for injection," "Dose still too high," "Dose too high by: 0.10 mg," "0.10 mg less will be injected," and "Current dose: 0.90 mg," and in this state, control proceeds to S307 in FIG. 18. That is, in this state, when the pharmaceutical injection button 33 in FIG. 1 is pressed after air venting, as discussed above, the needle insertion and retraction drive motor 12 is driven, the injection needle 14 is inserted into the body, the piston drive motor 10 is driven in this state, and the above-mentioned 0.90 mg of pharmaceutical is injected.

2-2-4. Dose Correction for Unplanned Injection, and Rescheduling

Figure 22:
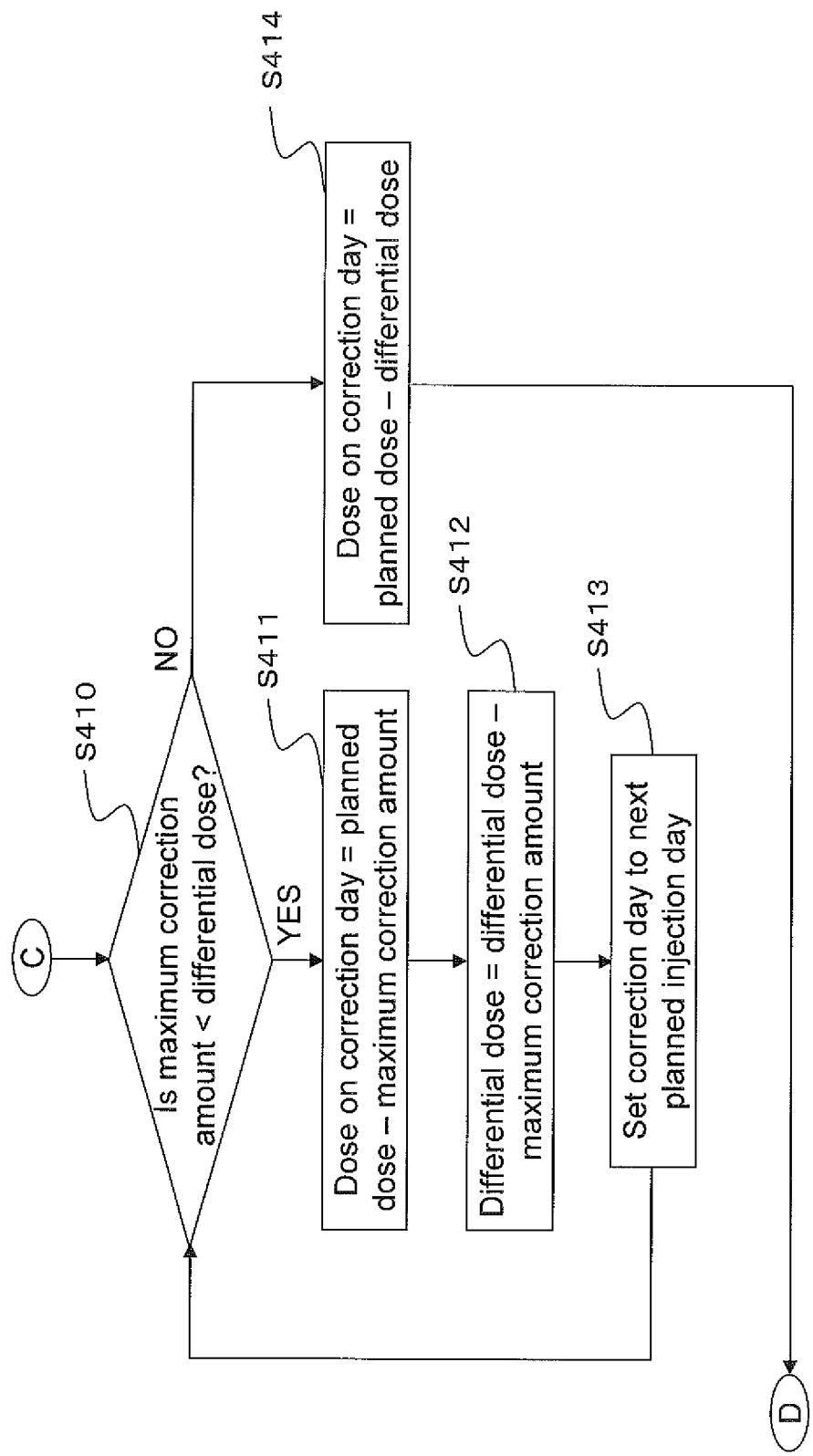
FIG. 22 is a flowchart of the operation of the pharmaceutical injection device pertaining to Embodiment 2 of the present invention.

FIG. 22 is a flowchart of the control over the dose correction operation performed when there is an unplanned injection (excess injection).

When unplanned pharmaceutical injection is performed, control proceeds to S410 shown in FIG. 22, via S401, S402, and S403 shown in FIG. 20. That is, when excess injection is performed by injection on a Saturday, which is not a planned injection day, the actual cumulative dose is greater than the initial planned cumulative dose based on the pharmaceutical injection schedule set by the physician at the outset, and the differential dose is 1.0 mg, so control moves to S410 in FIG. 22.

In S410, the controller 7 determines whether or not the differential dose is greater than the maximum correction amount, and if the differential dose is greater than the maximum correction amount, in S411 the remainder obtained by subtracting the maximum correction amount (0.30 mg) from the planned dose (1.00 mg) as the current (Monday) dose (0.70 mg).

Next, in S412, the controller 7 calculates the new differential dose as the remainder obtained by subtracting the maximum correction amount from the differential dose. More specifically, since the differential dose is 1.0 mg, the new differential dose is calculated as 0.70 mg.

Next, in S413, the controller 7 sets the correction day as the next planned injection day. If it is Monday this time, then Tuesday, the next planned injection day, is set as the new correction day.

The control then returns to S410, in which it is determined whether or not the newly calculated differential dose is greater than the maximum correction amount. Since the differential dose is 0.7 mg and is greater than the maximum correction amount (0.30 mg), control proceeds to S411, and the dose for Tuesday (the correction day) is the remainder (0.70 mg) obtained by subtracting the maximum correction amount (0.30 mg) from the planned dose (1.00 mg). Then, in S412, the new differential dose is set to 0.40 mg, from the differential dose (0.70 mg)–the maximum correction amount (0.30 mg), and Wednesday, which is the next planned injection day, is set as the correction day in S413. The control again proceeds to S410, but since the differential dose is 0.40 mg, it is still greater than the maximum correction amount (0.30 mg), so control proceeds to S411, and the dose for Wednesday (the correction day) is calculated as 0.70 mg. Then, in S412 the new differential dose is calculated as 0.10 mg (0.40 mg-0.30 mg), and in S413 Thursday is set as the next correction day.

The control then returns to S410, but since the differential dose this time is 0.10 mg, it is less than the maximum correction amount (0.30 mg), so control proceeds to S414. Then, in S414 the correction amount for Thursday is calculated as 0.90 mg by subtracting the differential dose (0.10 mg) from the planned dose (1.00 mg).

The situations on Monday, Tuesday, and Wednesday (in which the dose is 0.70 mg) are as discussed above.

Also, as discussed above, if the differential dose is less than the maximum correction amount in S410, then in S414 the remainder obtained by subtracting the differential dose from the planned dose (1.00 mg) is set as the current dose. That is, we have the above-mentioned situation for Thursday (in which the dose is 0.90 mg) (S414 in FIG. 22).

Then, in S336, the corrected planned dose is used to reset the schedule as shown in FIG. 30, which is stored in the memory 46. The dose for uncorrected days is the same as that on the schedule prior to being reset. The pharmaceutical injection schedule initially set by the physician (FIG. 26) is stored in the memory 46.

2-2-5. Pharmaceutical Injection Preparatory Operation from Schedule Resetting Onward The pharmaceutical injection preparatory operation on the planned pharmaceutical injection days following the resetting of the schedule will now be described by giving a specific example.

2-2-5-1. When Injection is Skipped (Insufficient Dose)

As discussed above, since the pharmaceutical injection schedule shown in FIG. 26 and set by the physician at the outset was reset on Apr. 11, 2011 to the pharmaceutical injection schedule shown in FIG. 28, the injection of 1.30 mg of pharmaceutical is planned for April 12.

As shown in FIG. 18, when the patient turns on the power to the pharmaceutical injection device (S301) on April 12, which is a planned pharmaceutical injection day following the resetting of the schedule, control proceeds to S302, S303, and S305.

Then, in S305, it is determined whether or not the actual cumulative pharmaceutical dose is the same as the initial planned cumulative pharmaceutical dose. Here, the actual cumulative pharmaceutical dose up to the last time before April 12 (April 11) is 6.30 mg. On the other hand, the initial planned cumulative pharmaceutical dose, as given in the pharmaceutical injection schedule in FIG. 26, is 7.00 mg. Since the actual cumulative pharmaceutical dose is thus less than the initial planned cumulative pharmaceutical dose, control proceeds to S305, S308, and S309.

Next, in S309, it is determined by the controller 7 whether or not the last injection was skipped. Since injection was not skipped on the last time before April 12 (April 11), control proceeds to S316. Then, in S316, if the remainder obtained by subtracting the actual cumulative pharmaceutical dose up to the last time from the initial planned cumulative pharmaceutical dose up to the last time on the basis of the pharmaceutical injection schedule set at the outset is at or above the allowable divergence, in S317 the controller 7 causes the display component 35 to give the display shown in FIG. 16e, and displays a message recommending consultation with a physician. However, at the point of injection on April 12, as discussed above, the actual cumulative pharmaceutical dose is 7.30 mg, while the planned cumulative pharmaceutical dose set at the outset is 8.00 mg, so the discrepancy is 0.70 mg, which is less than the allowable divergence of 1.50 mg. Therefore, control does not proceed to S317, and instead proceeds from S316 to S318, in which a display similar to that in FIG. 16f is given. More specifically, "Ready for injection," "Dose still short," "Dose short by: 0.70 mg," "Extra 0.30 mg will be injected," and "Current dose: 1.30 mg" are displayed.

Then, control proceeds to S307, and the pharmaceutical injection device enters its injection standby mode. When air venting is performing in this state and the pharmaceutical injection button 33 is then pressed, the injection of 1.30 mg of pharmaceutical is executed on the basis of the pharmaceutical injection schedule reset on April 11 (see FIG. 28).

As shown in FIG. 28, in the pharmaceutical injection on April 15, the actual cumulative pharmaceutical dose up to the last time is 10.00 mg, and the planned cumulative pharmaceutical dose up to the last time is also 10.00 mg, so control proceeds to S306, the displays of "Ready for injection" and "Current dose: 1.00 mg" shown in FIG. 16c are given, the pharmaceutical injection device goes into injection standby mode (S307), and when the pharmaceutical injection button 33 is pressed after air venting, 1.00 mg of pharmaceutical is injected.

2-2-5-2. When there is Unplanned Injection (Excessive Dose)

As discussed above, since unplanned injection was performed on Saturday, the pharmaceutical injection schedule shown in FIG. 26 and preset by the physician was reset on Apr. 11, 2011 to the pharmaceutical injection schedule shown in FIG. 30, so injection of 0.70 mg of pharmaceutical on April 12 is planned.

As shown in FIG. 18, if the patient turns on the power to the pharmaceutical injection device (S301) on April 12, which is a planned injection day after the resetting of the schedule, control proceeds to S302, S303, and S305.

Then, in S305, it is determined whether or not the actual cumulative pharmaceutical dose is the same as the initial planned cumulative pharmaceutical dose. Here, the actual cumulative pharmaceutical dose up to the last time before April 12 (April 11) is 7.70 mg. On the other hand, the initial planned cumulative pharmaceutical dose, as given in the pharmaceutical injection schedule in FIG. 26, is 7.00 mg. Since the actual cumulative pharmaceutical dose is thus greater than the initial planned cumulative pharmaceutical dose, control proceeds to S305, S308, and S330 (see FIG. 21). In S330, it is determined whether or not the difference between the actual cumulative pharmaceutical dose and the initial planned cumulative pharmaceutical dose is less than the allowable divergence, and since the allowable divergence is 1.50 mg, control proceeds to S334. In S334, since pharmaceutical injection has been performed as planned on April 11 (the last time), control proceeds to S339. Then, in S339, the controller 7 gives the displays "Ready for injection," "Dose still too high," "Dose too high by: 0.70 mg,"

"0.30 mg less will be injected," and "Current dose: 0.70 mg" as shown in FIG. 16i, and control proceeds to S307.

In the pharmaceutical injection on April 13, "Dose still too high," "Dose too high by: 0.40 mg," "0.30 mg less will be injected," and "Current dose: 0.70 mg" are displayed, and pharmaceutical injection of 0.70 mg is performed.

Also, in the pharmaceutical injection on April 14, "Dose still too high," "Dose too high by: 0.10 mg," "0.10 mg less will be injected," and "Current dose: 0.90 mg" are displayed, and pharmaceutical injection of 0.90 mg is performed.

As shown in FIG. 30, in the pharmaceutical injection on April 15, since the actual cumulative pharmaceutical dose up to the last time is 10.00 mg and the initial planned cumulative pharmaceutical dose up to the last time is 10.00 mg, control proceeds from S305 to S306, the display of "Ready for injection. Current dose: 1.00 mg" shown in FIG. 16c is given, and the pharmaceutical injection device enters its injection standby mode (S307).

As discussed above, in Embodiments 1 and 2 of the present invention, the configuration is such that the memory 46 (which stores a pharmaceutical injection schedule) connected to the controller 7 is provided inside the main body case 2, the controller 7 compares the actual cumulative pharmaceutical dose up to the last time with the planned cumulative pharmaceutical dose up to the last time based on the pharmaceutical injection schedule preset by the physician, and the future pharmaceutical injection schedule is reset accordingly. Therefore, even if the user skips a pharmaceutical injection, for example, the pharmaceutical injection device itself will reset the future pharmaceutical injection schedule, and as a result there is no need for the user to visit a physician and have the schedule reset, which makes the device more convenient to use.

In Embodiment 2, the description was of resetting the pharmaceutical injection schedule preset by the physician to a new pharmaceutical injection schedule, but if pharmaceutical injection is skipped, adjusted, etc., in the course of the reset pharmaceutical injection schedule, the schedule is further reset according to the control flow in FIGS. 18 to 22. This further resetting is executed when pharmaceutical injection is skipped or adjusted during a corrected injection period for a reset pharmaceutical dose (the period of a dose that differs from the pharmaceutical dose set by the physician). In this case, the pharmaceutical injection schedule reset by the controller 7 may be updated to the further reset pharmaceutical injection schedule and deleted from the memory 46, but the pharmaceutical injection schedule set by the physician will remain stored in the memory 46.

Embodiment 3

FIGS. 31 to 40 illustrate Embodiment 3 of the present invention. In this embodiment, priority is given to using up all of the pharmaceutical inside the pharmaceutical syringe 4. As will be understood from the description of Embodiment 2 above, when the pharmaceutical to be injected is one that is injected in a specific amount within a specific period of time, that is, a pharmaceutical with which it is acceptable to inject an extra amount on the next day to make up for injection skipped on one day, such as a growth hormone, then it is sometimes a priority to use up all of the pharmaceutical in the pharmaceutical syringe 4 as in Embodiment 3. Also, growth hormones are expensive, which is another reason for recommending that all of the pharmaceutical in the pharmaceutical syringe 4 be used up.

With the pharmaceutical injection device in Embodiment 3, the pharmaceutical injection schedule is reset in order to adjust a pharmaceutical dose that is either too high or too low as a result of thus using up all of the pharmaceutical.

3-1. Pharmaceutical Injection Schedule

Again in Embodiment 3, the injection of the pharmaceutical in the pharmaceutical syringe 4 is divided up into a number of times. In one example, the pharmaceutical is injected for six days in a row on Sunday, Monday, Tuesday, Wednesday, Thursday, and Friday, and not injected on Saturday. FIG. 34 shows this pharmaceutical injection schedule.

The pharmaceutical injection schedule shown in FIG. 34 was set by a physician, and in which the pharmaceutical injection days and doses are set, and this pharmaceutical injection schedule is stored in the memory 46 in FIG. 3 as the pharmaceutical injection schedule set at the outset.

As a result, a control program stored in the ROM 38 thereafter executes operations while referring to the pharmaceutical injection schedule stored in the memory 46.

Figure 31:
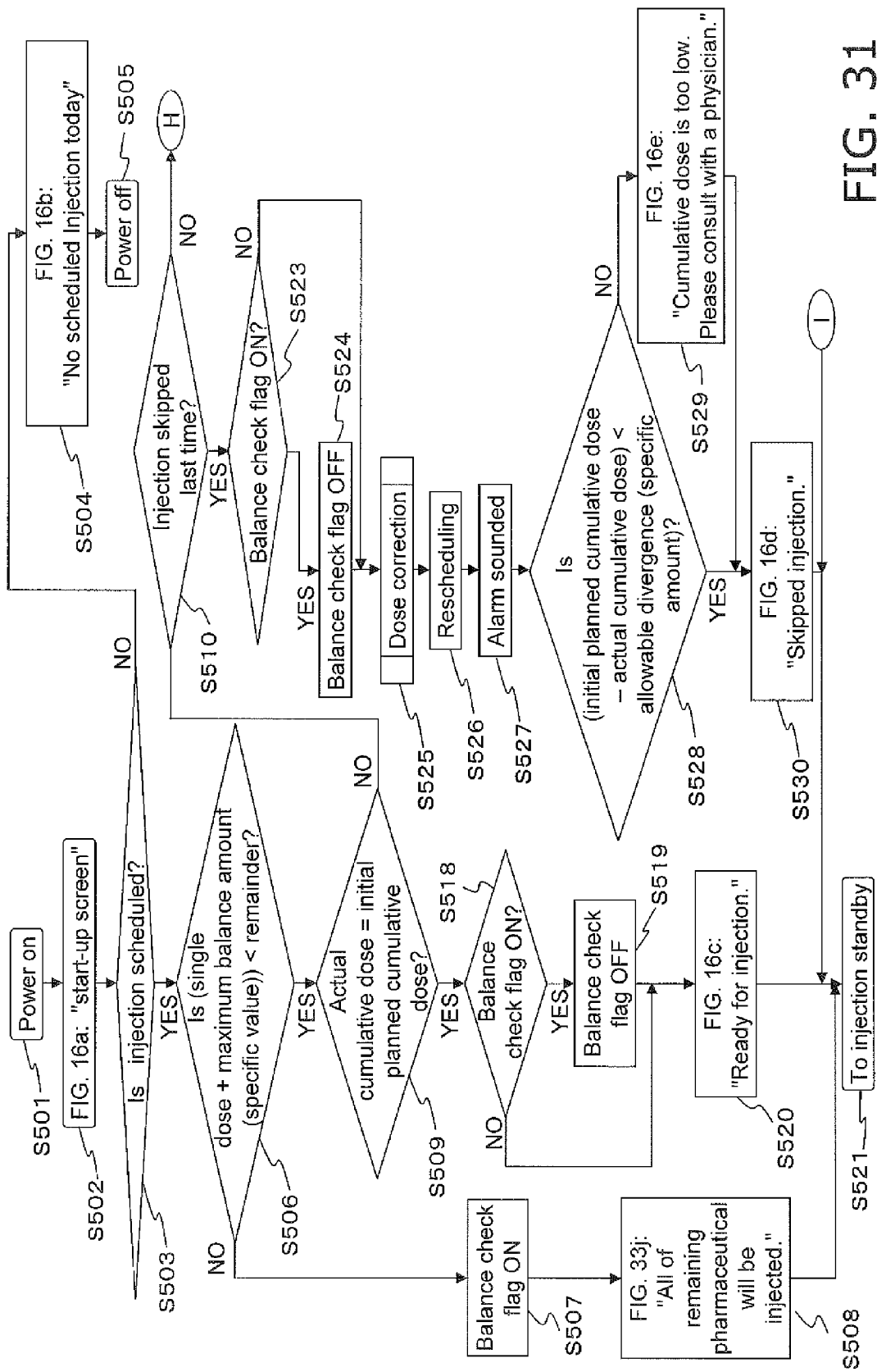
FIG. 31 is a flowchart of the operation of the pharmaceutical injection device pertaining to Embodiment 3 of the present invention.
Figure 32:
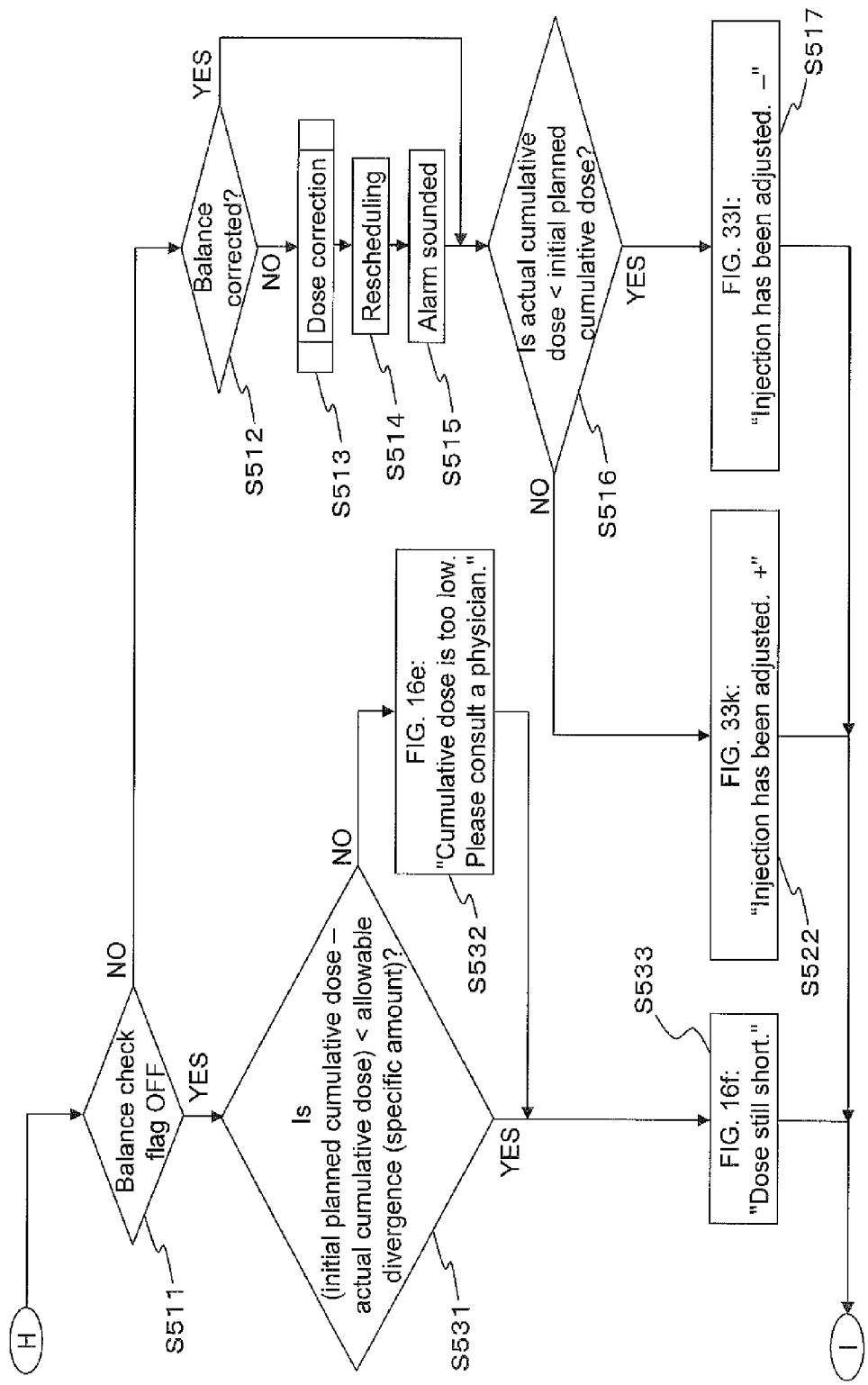
FIG. 32 is a flowchart of the operation of the pharmaceutical injection device pertaining to Embodiment 3 of the present invention.

Accordingly, as shown in FIGS. 1 and 2, when the power button 31 is pressed (S501 in FIG. 31) in a state in which the pharmaceutical syringe 4 has been mounted to the pharmaceutical syringe mounting component 3, the pharmaceutical injection preparatory operation shown in FIGS. 31 and 32 is carried out. This pharmaceutical injection preparatory operation involves checking the pharmaceutical injection days, pharmaceutical doses, and so forth, correcting the pharmaceutical doses, and performing other such operations on the basis of the pharmaceutical injection schedule prior to performing the pharmaceutical injection operation.

3-2. Pharmaceutical Injection Preparatory Operation

The pharmaceutical injection preparatory operation performed by the pharmaceutical injection device in this embodiment will now be described. FIGS. 31 and 32 show the control flow of the pharmaceutical injection preparatory operation.

3-2-1. Insufficient Dose Due to Adjusted Injection

In specific terms, when the power button 31 is pressed (S501 in FIG. 31), the display component 35 displays the start-up screen shown in FIG. 16a (S502 in FIG. 31). Next, it is confirmed whether or not injection is planned on the pharmaceutical injection schedule (S503 in FIG. 31).

At this point, as is clear from the pharmaceutical injection schedule in FIG. 34, Apr. 9, 2011 is a Saturday, and no pharmaceutical injection is planned on this pharmaceutical injection schedule. Therefore, as shown in FIG. 16b, the display component 35 displays "No scheduled injection today" (S504 in FIG. 31), and the power is switched off (S505 in FIG. 31).

Also, if it is a pharmaceutical injection day set on the pharmaceutical injection schedule, then it is determined whether or not the value obtained by adding a maximum balance amount to the single dose set in the pharmaceutical injection schedule is greater or less than the remaining amount of pharmaceutical in the pharmaceutical syringe 4 (S506 in FIG. 31).

More specifically, as shown in FIG. 34, the single dose set in the pharmaceutical injection schedule is 1.0 mg, and the maximum balance (borrowing and lending) amount is 0.30 mg. In this embodiment, the maximum balance amount and the maximum correction amount are both 0.30 mg, but the maximum balance amount may instead be set to 0.50 mg.

In this state, if 6.50 mg of pharmaceutical was contained in the pharmaceutical syringe 4, then on April 8 in FIG. 35 only 0.50 mg remains in the pharmaceutical syringe 4, so 0.50 mg is injected on April 8 to use up the rest of the pharmaceutical in the pharmaceutical syringe 4. FIG. 35 shows the pharmaceutical injection results of using up the pharmaceutical by the pharmaceutical injection schedule and the balance method.

This state is on the "No" side in S506 in FIG. 31, and at this point the controller 7 switches the balance check flag in the memory 46 to the ON state (S507 in FIG. 31), the display component 35 displays "Ready for injection. All of remaining pharmaceutical will be injected to use it up. Current dose: 0.50 mg" (S508 in FIG. 31), and the pharmaceutical injection operation is executed.

When the pharmaceutical injection operation of April 10 shown in FIG. 35 is executed in this state, control goes through S502 and S503 in FIG. 31, and reaches S506, where it is determined whether the value obtained by adding the maximum balance amount to the single dose set in the pharmaceutical injection schedule is greater or less than the remaining amount of pharmaceutical in the pharmaceutical syringe 4. On April 10, since a new pharmaceutical syringe 4 has been mounted, 6.50 mg of pharmaceutical still remains in it.

Therefore, in S506, the state is Yes, and then in S509, the controller 7 compares the actual cumulative pharmaceutical dose up to the last time with the planned cumulative pharmaceutical dose up to the last time based on the pharmaceutical injection schedule preset by the physician and stored in the memory 46.

That is, when the pharmaceutical injection is carried out according to the pharmaceutical injection schedule shown in FIG. 34, as shown in FIG. 35, the pharmaceutical injection results are recorded to the memory 46 on a daily basis, so the controller 7 compares the actual cumulative pharmaceutical dose up to the last time with the planned cumulative pharmaceutical dose up to the last time based on the pharmaceutical injection schedule preset by the physician and stored in the memory 46 as mentioned above.

In this state, on April 8 only 0.50 mg of pharmaceutical remains in the pharmaceutical syringe 4, so in the determination on April 10 in S509, the actual cumulative pharmaceutical dose up to the last time and the planned cumulative pharmaceutical dose up to the last time are not equal, so the flow moves to S510.

In S510, it is determined whether or not injection was skipped the last time. Since injection was performed on April 8, control proceeds to S511 (see FIG. 32). This step S510 is provided to prioritize the resetting of the pharmaceutical injection schedule due to skipped injection over the resetting of the pharmaceutical injection schedule due to all of the pharmaceutical having been used up.

In S511, it is determined whether or not the balance check flag is OFF. Since the balance check flag is in its ON state on April 8, control proceeds to S512, and it is determined whether or not correction due to balance (discussed below) has been performed. Since the pharmaceutical injection schedule has not been corrected from the injection on April 1, control proceeds to S513, and the controller 7 resets the pharmaceutical injection schedule from April 10 onward, as shown in FIG. 36 (S513 and S514). In S513, the future pharmaceutical dose is corrected, and in S514 the pharmaceutical injection schedule is reset due to the corrected pharmaceutical dose. The dose correction in S513 is the same as the dose correction in FIGS. 20 and 22 and described in Embodiment 2, and will therefore not be described again. FIG. 36 shows the pharmaceutical injection schedule after resetting. The correction of pharmaceutical dose due to adjusted injection having been performed for using up the pharmaceutical is also called balance correction.

When the pharmaceutical injection schedule is reset, the buzzer 44 emits an alarm sound to notify the user that the pharmaceutical injection schedule has been reset (S515 in FIG. 32).

Next, control proceeds to S516, and it is determined whether or not the actual cumulative pharmaceutical dose is less than the initial planned cumulative pharmaceutical dose. Since only 0.50 mg is injected on April 8, the actual cumulative dose is less than the initial planned cumulative dose, so the flow goes through YES and reaches S517. In S517 the controller 7 causes the display component 35 to display "Ready for injection. Injection has been adjusted. Extra 0.30 mg will be injected. Remaining adjustment dose: −0.20 mg. Current dose: 1.30 mg," and the pharmaceutical injection operation is executed.

As shown in FIG. 36, in S514 since the pharmaceutical injection schedule has been reset, on the next day (April 11), 1.20 mg of pharmaceutical is injected.

3-2-2. Pharmaceutical Injection Preparatory Operation After Schedule Resetting When the injection operation is performed on April 11, control proceeds to S501, S502, S503, S506, S509, S510, S511, and S512, but since balance correction is being performed, dose correction is not performed, control proceeds to S516, and it is determined whether or not the actual cumulative dose is less than the planned cumulative dose. Because the dose was short by 0.50 mg in the pharmaceutical injection on April 8, 1.30 mg is injected on April 10, which makes up for 0.30 mg, but the dose is still 0.20 mg short. Accordingly, the actual cumulative dose is still less than the planned cumulative dose, control proceeds to S517, and in S517 a display is given indicating "Ready for injection. Injection has been adjusted. Extra 0.20 mg will be injected. Remaining adjustment dose: −0.00 mg. Current dose: 1.20 mg."

The planned dose on April 12 is the same as the initial planned dose (1.00 mg), but the control flow here will be described. Since the dose correction up to today is complete at this point, the power is switched on in S501, after which control proceeds to S502, S503, and S506. The amount of pharmaceutical contained in the pharmaceutical syringe 4 is 6.50 mg, and since a new pharmaceutical syringe 4 is used on April 10, the remaining amount is 4.00 mg. Accordingly, control proceeds to S509, and it is determined whether or not the actual cumulative dose is the same as the initial planned cumulative dose. Here, in the pharmaceutical injection on April 12, since the actual cumulative dose and the initial planned cumulative dose are the same, control proceeds to S518. In S518, it is determined whether or not the balance check flag is in its ON state, and if the balance check flag is in its ON state, it is switched to OFF in S519.

In the specific example shown in FIG. 36, since the balance check flag is in its ON state on April 8, in S519 the balance check flag is in its OFF state. Then, in S520, the display of "Ready for injection. Current dose: 1.00 mg" shown in FIG. 16c is given, and the flow moves to the injection standby mode of S521.

3-2-3. Excess Dose Due to Adjustment Injection

If there was 7.20 mg of pharmaceutical contained in the pharmaceutical syringe 4, then 1.20 mg of pharmaceutical will remain in the pharmaceutical syringe 4 on April 8.

If there is thus 1.20 mg of pharmaceutical remaining in the pharmaceutical syringe 4, all of it may be injected on April 8 as in FIG. 37, for example. That is, the purpose of this is to avoid a situation in which the amount of pharmaceutical remaining in the pharmaceutical syringe 4 is less than the maximum balance amount (±0.30 mg in this embodiment). At this point, all of the pharmaceutical is injected via steps S501, S502, S503, S506, S507, and S508.

At this point the display component 35 gives a display of "Ready for injection. All of remaining pharmaceutical will be injected to use it up. Current dose: 1.20 mg" (S508 in FIG. 31), and the pharmaceutical injection operation is executed.

If this state is in effect when April 10 arrives, just as when the dose is insufficient due to adjustment injection, the control goes through S501, S502, S503, S506, S509, S510, S511, and S512, thus reaching S513, and in S513 the pharmaceutical injection schedule is reset. In this resetting, unlike when the dose was insufficient due to adjustment injection, the pharmaceutical injection dose is reduced below what was preset by the physician.

That is, on April 10, the pharmaceutical dose is reset to 0.80 mg, and the buzzer 44 emits an alarm sound to notify the user that the pharmaceutical injection schedule has been reset (S515 in FIG. 32). FIG. 38 shows the reset schedule.

The control then moves to S516, and since this time the actual cumulative dose is greater than the planned cumulative dose, the flow moves to S522, and the display component 35 gives the display in FIG. 33k. That is, the display of "Ready for injection. Injection has been adjusted. 0.20 mg less will be injected. Remaining adjustment dose: 0 mg. Current dose: 0.80 mg," the device goes into injection standby mode (S521), and the pharmaceutical injection preparatory operation is executed. The pharmaceutical injection preparatory operation on April 11 shown in FIG. 38 is controlled the same as the above-mentioned operation on April 12 shown in FIG. 36.

3-2-4. Pharmaceutical Injection Skipped During Correction Period

We will now describe a case in which an injection is skipped during the period of injection by corrected amount after schedule resetting following adjustment injection (a different period from that of the pharmaceutical dose preset by the physician).

More specifically, a case was described in which pharmaceutical injection was skipped on April 11 after 0.50 mg of pharmaceutical was injected due to adjustment injection on April 8, and the pharmaceutical injection schedule was reset on April 10. The pharmaceutical injection schedule and pharmaceutical injection results in this case are shown in FIG. 39.

In this state, when the power is turned on to the pharmaceutical injection device on April 12, control proceeds to S501, S502, S503, and S506. At this point the remaining amount is 5.20 mg (6.50 mg-1.30 mg), and since the sum of the maximum balance amount and the single dose set by the physician is 1.30 mg, control proceeds to S509 and S510. Then, in S510, since injection was skipped the last time (April 11), control proceeds to S523. Here, if the balance check flag is ON, it is switched off in S524, control proceeds to S525 and S526, and the correction amount is calculated and the schedule reset. In the example shown in FIG. 39, the balance check flag is in its ON state on April 10, so the correction amount is calculated and the schedule is reset once the balance check flag has been set to OFF.

This calculation of the correction amount is the same as the dose correction in FIG. 17 and described in Embodiment 1. Prior to the pharmaceutical injection on April 12, the initial planned cumulative dose is 9.00 mg (1.00 mg×9 days), the actual cumulative dose is 7.80 mg (1.00 mg×6 days+0.50 mg+1.30 mg+0.00 mg), and the differential dose is −1.20 mg. Accordingly, the schedule after correction is reset as shown in FIG. 40. The pharmaceutical injection schedule shown in FIG. 39 and stored in the memory 46 is then updated to the pharmaceutical injection schedule shown in FIG. 40. The initial pharmaceutical injection schedule shown in FIG. 34 and set by the physician is kept in the memory 46.

When the schedule is reset in this way, the buzzer 44 emits an alarm sound to notify the user that the pharmaceutical injection schedule has been reset (S527 in FIG. 31).

Next, if the remainder obtained by subtracting the actual cumulative pharmaceutical dose up to the last time from the initial planned cumulative pharmaceutical dose up to the last time based on the pharmaceutical injection schedule set at the outset by a physician is at or above a specific value (allowable divergence), the controller 7 gives the display shown in FIG. 16e in S529, and displays a message recommending a consultation with a physician. In the example shown in FIG. 40, the remainder is 1.20 mg, which is less than the allowable divergence (1.50 mg in Embodiment 3). Therefore, the controller 7 gives a display similar to that in FIG. 16d on the display component 35 (S530 in FIG. 31).

The display here is "Ready for injection," "Skipped injection," "Dose short by: 1.20 mg," "Extra 0.30 mg will be injected," and "Current dose: 1.30 mg," and since an injection was skipped, the display tells the user that the dose will be slightly higher this time, for example.

Therefore, if the pharmaceutical injection button 33 in FIG. 1 is pressed in this state after the air venting operation, as discussed above, the needle insertion and retraction drive motor 12 is driven, the injection needle 14 is inserted into the body, the piston drive motor 10 is driven in this state, and the above-mentioned 1.30 mg of pharmaceutical is injected.

As discussed above, in S528, if the remainder obtained by subtracting the actual cumulative pharmaceutical dose up to the last time from the planned cumulative pharmaceutical dose (the initial planned cumulative pharmaceutical dose) up to the last time based on the pharmaceutical injection schedule set by a physician is at or above a specific value (allowable divergence), the controller 7 gives the display shown in FIG. 16e on the display component 35, and this situation is one in which injection has been skipped twice, such as when pharmaceutical injection was skipped again on April 12 from the state shown in FIG. 40 (in which pharmaceutical injection had been skipped on April 11). The initial planned cumulative pharmaceutical dose on April 13 when pharmaceutical injection is performed is 10.00 mg, the actual cumulative pharmaceutical dose is 7.80 mg, and the difference is 2.20 mg. The specific value (allowable divergence) is 1.50 mg, so control proceeds from S528 to S529, and the display shown in FIG. 16e is given. As shown in FIG. 16e, the display is "Cumulative dose is too low" and "Please consult with a physician," and a message recommending consultation with a physician is displayed on the display component 35.

However, since the pharmaceutical this time is a growth hormone, for example, it is preferably injected without interruption, and at this point control proceeds to S530, and the controller 7 gives a display similar to that in FIG. 16d on the display component 35.

When control then proceeds from S529 to S530, in S530, a display of "Ready for injection," "Skipped injection," "Dose short by: 2.20 mg," "Extra 0.30 mg will be injected," and "Current dose: 1.30 mg" is given.

Thus, when an injection has been skipped, the schedule is updated so that the dose is increased slightly the next time in order to make for the shortage, but if the injection has been skipped many times, it will take a long time to make up for this, so the user is urged to consult a physician.

3-2-5. Pharmaceutical Injection Preparatory Operation After Schedule Resetting Due to Skipped Injection Continuing from the above, when a correction amount is injected after the schedule has been reset due to a skipped injection, with the pharmaceutical injection schedule shown in FIG. 40, for example, a case will be described of performing pharmaceutical injection after resetting the schedule on April 12, and performing pharmaceutical injection on April 13. When the power is switched on, control proceeds to S501, S502, S503, S506, S509, and S510. In S510, since pharmaceutical injection was performed the last time (April 12), control proceeds to S511. In the control on April 12, since the balance check flag is in its OFF state (S524), control proceeds to S531.

Here, just as in S528 and S529, it is determined whether or not the difference between the initial planned cumulative dose and the actual cumulative dose is greater than the allowable divergence. More specifically, prior to pharmaceutical injection on April 13, the initial planned cumulative pharmaceutical dose is 10.00 mg, the actual cumulative pharmaceutical dose is 9.10 mg, and the difference is 0.90 mg. Since the specific value (allowable divergence) is 1.50 mg, control proceeds from S531 to S533, and in S533 a message of "Ready for injection," "Dose still short," "Dose short by: 0.90 mg," "Extra 0.30 mg will be injected," and "Current dose: 1.30 mg" is given, and control moves to the injection standby mode (S521).

In S531, if the remainder obtained by subtracting the actual cumulative pharmaceutical dose up to the last time from the planned cumulative pharmaceutical dose (the initial planned cumulative pharmaceutical dose) up to the last time based on the pharmaceutical injection schedule preset by the physician is greater than a specific value (allowable divergence), the controller 7 gives the display shown in FIG. 16e on the display component 35, and this is a case in which pharmaceutical injection was skipped twice, as when, for instance, injection was skipped again on April 12 from the state shown in FIG. 40 (a state in which pharmaceutical injection was skipped on April 11), and the schedule was reset on April 13 and pharmaceutical injection is to be performed on April 14. On April 14 when pharmaceutical injection is performed, the initial planned cumulative pharmaceutical dose is 11.00 mg, the actual cumulative pharmaceutical dose is 9.10 mg, and the difference is 1.90 mg. Since the specific value (allowable divergence) is 1.50 mg, control proceeds from S531 to S532, and the display shown in FIG. 16e is given. The display shown in FIG. 16e is "Cumulative dose too low" and "Please consult a physician," and a message recommending a consultation with a physician is displayed on the display component 35.

However, since the pharmaceutical this time is a growth hormone, it is preferably injected without interruption, and at this point control proceeds to S533, the controller 7 gives a display similar to that in FIG. 16f, which is "Ready for injection," "Dose still short," "Dose short by: 1.90 mg," "Extra 0.30 mg will be injected," and "Current dose: 1.30 mg," and the control moves to the injection standby mode (S521).

The pharmaceutical dose is corrected in Embodiments 1 to 3 above, but since an upper limit to the dose taken within a specific period is provided for each type of pharmaceutical, the injection schedule can be set within that range. In the case of Embodiment 2, the upper limit for seven days is 6.5 mg (the planned dose of 1.0 mg×5 (the number of planned injection days)+the allowable divergence of 1.5 mg).

4. Features of Pharmaceutical Injection Device

The pharmaceutical injection device in this embodiment comprises the main body case 2, the pharmaceutical syringe mounting component 3, the piston 5, the drive mechanism 6, the display component 35, the memory 46, and the controller 7. The main body case 2 has an injection needle insertion and retraction opening 1 (an example of an opening) through which the injection needle 14 is inserted and retracted. The pharmaceutical syringe mounting component 3 is provided inside the main body case 2, and the pharmaceutical syringe 4 is mounted thereto. The piston 5 is provided movably with respect to the pharmaceutical syringe 4 mounted onto the pharmaceutical syringe mounting component 3. The drive mechanism 6 drives the piston 5. The display component 35 displays information related to the injection of a pharmaceutical. The memory 46 is provided inside the main body case 2 and stores a preset pharmaceutical injection schedule. The controller 7 is electrically connected to the drive mechanism 10, the display component 35, and the memory 46, and resets the current pharmaceutical dose by comparing a planned cumulative pharmaceutical dose, which is the planned cumulative amount of pharmaceutical injected up to the last time on the basis of the pharmaceutical injection schedule stored in the memory 46, and the actual cumulative pharmaceutical dose, which is the cumulative amount of pharmaceutical actually injected up to the last time.

Consequently, if a pharmaceutical injection is skipped, or if injection is performed on an unplanned day, the current pharmaceutical dose is reset automatically, so there is no need for the patient to visit a physician and have him reset the pharmaceutical injection schedule, which makes the device more convenient to use.

Also, with the pharmaceutical injection device in this embodiment, the controller 7 resets the future pharmaceutical injection schedule including the current pharmaceutical injection dose.

Consequently, the pharmaceutical injection schedule can be reset for not only the current pharmaceutical injection dose, but also the pharmaceutical injection period set by the physician at the outset. Also, the schedule for future pharmaceutical injection can be checked.

Also, with the pharmaceutical injection device in this embodiment, the reset future pharmaceutical injection schedule is stored in the memory 46, and the preset pharmaceutical injection schedule (the pharmaceutical injection schedule set by the physician) is kept.

Also, with the pharmaceutical injection device in this embodiment, when a reset future pharmaceutical injection schedule is further reset, the reset pharmaceutical injection schedule stored in the memory 46 is updated to the pharmaceutical injection schedule that has been further reset.

Consequently, even when the pharmaceutical injection schedule is reset a number of times, pharmaceutical injection can also be performed according to the newest pharmaceutical injection schedule.

Also, with the pharmaceutical injection device in this embodiment, the display component displays the current planned pharmaceutical dose, which is planned on the basis of the reset future pharmaceutical injection schedule.

Consequently, the patient can view the current planned pharmaceutical dose, which makes the device more convenient to use.

Also, with the pharmaceutical injection device in this embodiment, the display component displays whether the actual cumulative pharmaceutical dose is too high or too low, which is arrived at by comparison of the actual cumulative pharmaceutical dose up to the last time and the planned cumulative pharmaceutical dose up to the last time.

Consequently, the patient can view whether the current pharmaceutical injection is too high or too low, which makes the device more convenient to use.

Also, with the pharmaceutical injection device in this embodiment, the display component displays the reason why the actual cumulative pharmaceutical dose is too high or too low (such as adjustment injection), which is arrived at by comparison of the actual cumulative pharmaceutical dose up to the last time and the planned cumulative pharmaceutical dose up to the last time.

Consequently, the patient can view the reason why the current pharmaceutical injection is too high or too low, which makes the device more convenient to use.

Also, with the pharmaceutical injection device in this embodiment, the display component displays a message recommending a consultation with a physician when the amount by which the actual cumulative pharmaceutical dose is too high or too low, which is arrived at by comparison of the actual cumulative pharmaceutical dose up to the last time and the planned cumulative pharmaceutical dose up to the last time, exceeds a specific value.

Consequently, the patient can be prompted to consult with a physician when there is a large divergence from the pharmaceutical injection schedule set by the physician, which is very important to the patient.

Also, the method for controlling the pharmaceutical injection device in this embodiment comprises a resetting step of resetting a future pharmaceutical injection schedule by comparing a cumulative planned pharmaceutical dose, which is the planned cumulative amount of pharmaceutical injected up to the last time on the basis of a pharmaceutical injection schedule stored in the memory, and the actual cumulative pharmaceutical dose, which is the cumulative amount of pharmaceutical actually injected up to the last time. An example of this resetting step corresponds to the pharmaceutical dose correction operation and the rescheduling operation in this embodiment.

Consequently, even if a pharmaceutical injection is skipped, or if injection is performed on an unplanned day, the future pharmaceutical injection schedule is reset automatically, so there is no need for the patient to visit a physician and have him reset the pharmaceutical injection schedule, which makes the device more convenient to use.

5. Other Embodiments (A)

In the above embodiment, a future pharmaceutical injection schedule was reset, but all that really needs to be done is to correct at least the pharmaceutical dose for the time when the pharmaceutical is injected.

An embodiment in which just the pharmaceutical dose on a given day is corrected will now be described.

(A-1)

An example will be described in which the operation in Embodiment 1 is changed to an operation in which just the pharmaceutical dose on a given day is corrected.

Figure 41:
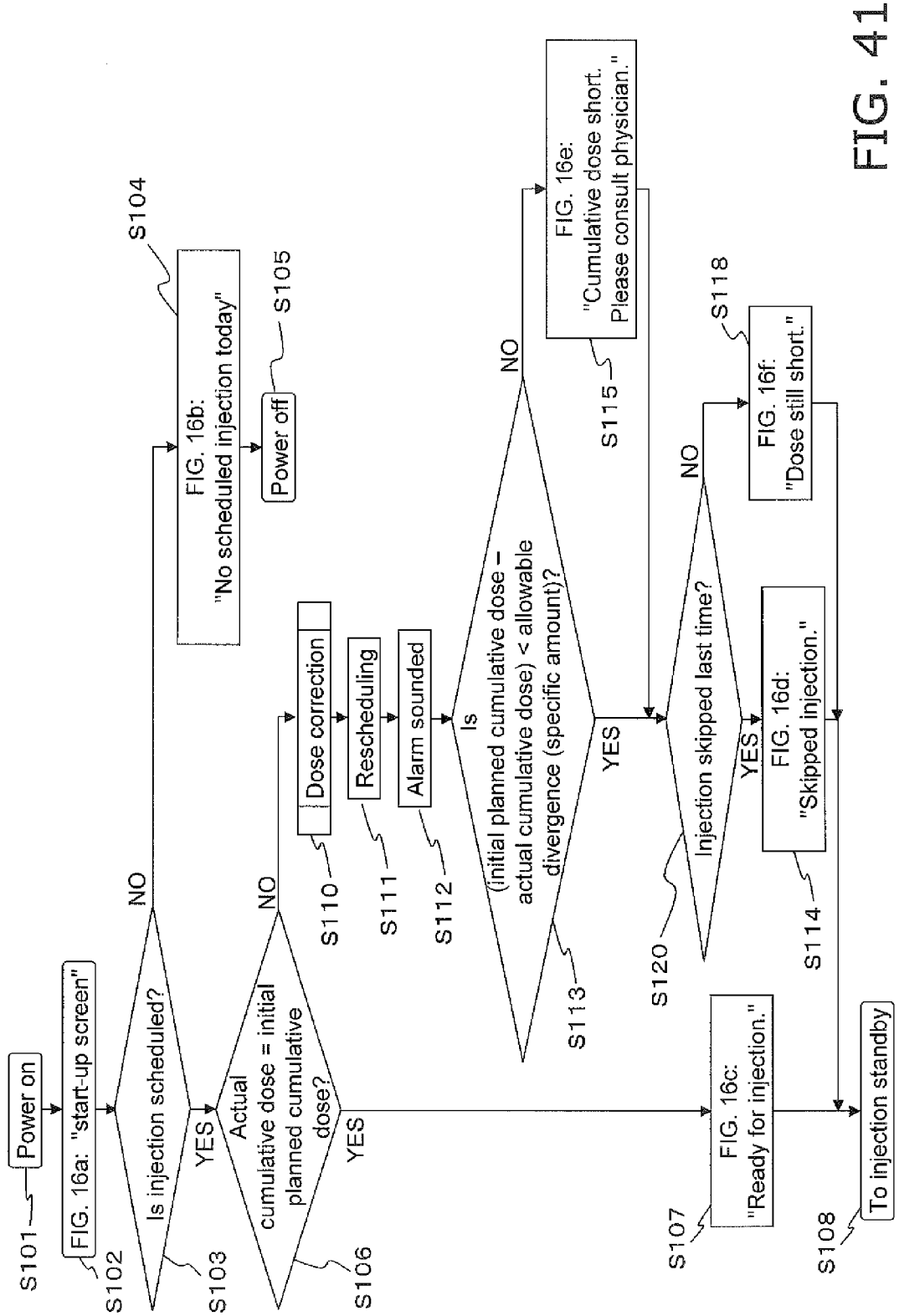
FIG. 41 is a flowchart of the operation of the pharmaceutical injection device pertaining to a modification example of Embodiment 1 of the present invention.
Figure 42:
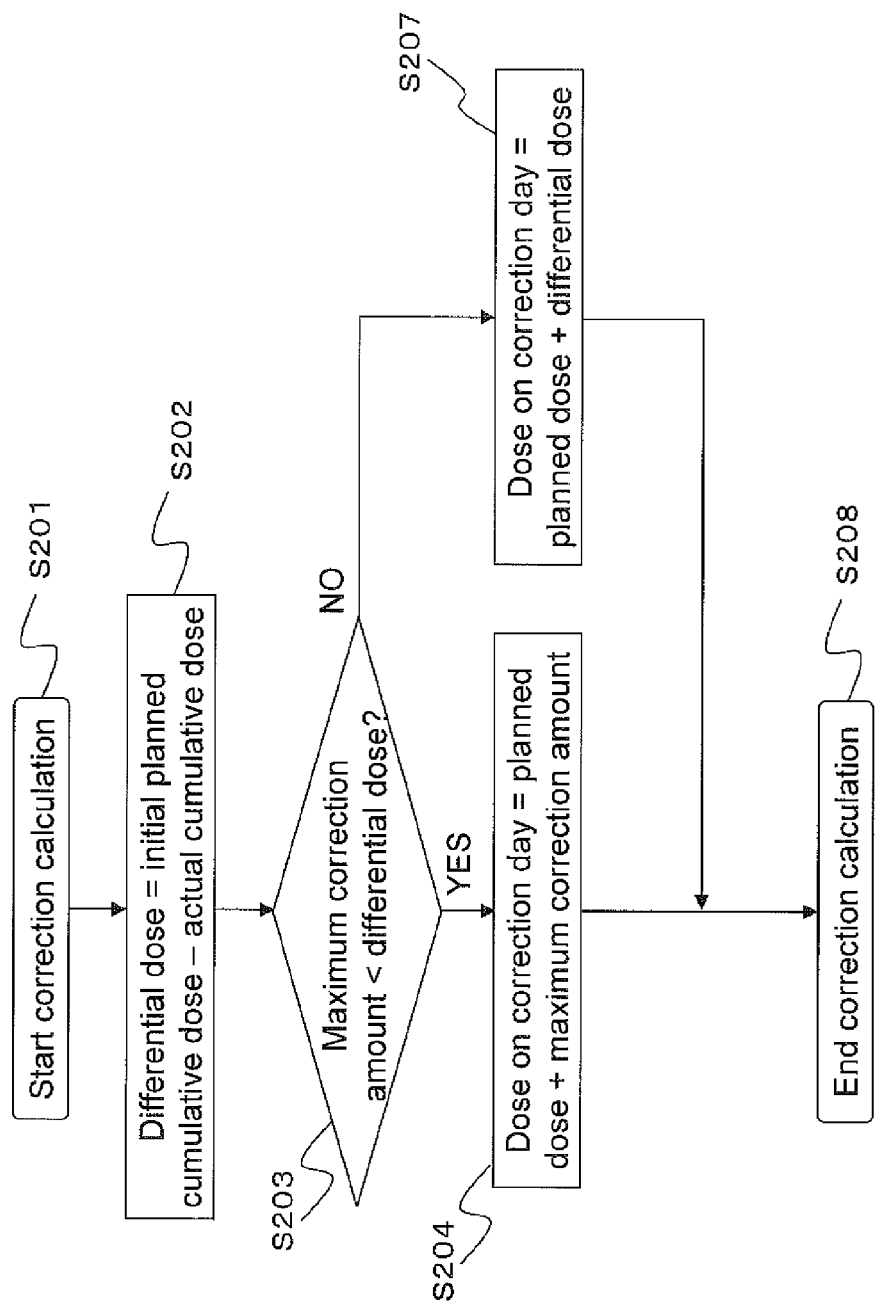
FIG. 42 is a flowchart of the operation of the pharmaceutical injection device pertaining to a modification example of Embodiment 1 of the present invention.

FIG. 41 shows the control flow in a pharmaceutical injection preparatory operation in the correction of just the pharmaceutical dose on a given day. FIG. 42 shows the control flow in a dose correction operation in which just the pharmaceutical dose on a given day is corrected. The control flows in FIGS. 41 and 42 are basically the same as the control flows described for FIGS. 15 and 17 in Embodiment 1, so the description will focus on the differences.

With the control flow shown in FIG. 15, the step of determining whether the last injection was skipped was provided between S106 and S110, but with the control flow shown in FIG. 41, it is provided between S113/S115 and S114, and the steps S116 and S117 shown in FIG. 15 are not provided in FIG. 41. Also, the steps S205 and S206 shown in FIG. 17 are not provided with the control flow in FIG. 42.

We will describe a case in which the pharmaceutical injection schedule shown in FIG. 23 has been preset by a physician, and pharmaceutical injection was skipped on April 8 as shown in FIG. 24.

When the power is switched on to the device on April 10, control proceeds to S101, S102, S103, and S106. Just as in Embodiment 1, in S106 there is a discrepancy between the initial cumulative planned dose (6.00 mg) and the actual cumulative dose (7.00 mg), so control proceeds to S110, and the dose is corrected in S110. As shown in FIG. 42, when correction calculation begins in S201, 1.00 mg is calculated as the differential dose in S202 by using the formula: (initial planned cumulative dose−actual cumulative dose). Since the differential dose is greater than the maximum correction amount (0.30 mg, just as in Embodiment 1), the current dose (a correction day) is calculated as 1.30 mg by using the formula: (planned dose+maximum correction amount), and correction calculation is ended (S208). The schedule is reset as shown in FIG. 43 on the basis of this correction calculation (S111). As shown in FIG. 43, only the dose for April 10 (the current injection day) is corrected. The alarm then sounds (S112). Also, the steps S113 and S115 are provided just as in Embodiment 1. After S113 or S115, it is determined in S120 whether or not the last injection was skipped. Since injection was skipped on April 8, control proceeds to S114 and the display shown in FIG. 16d is given, after which the device goes into injection standby mode (S108), air venting is performed, and the pharmaceutical injection button 33 is pressed, causing 1.30 mg of pharmaceutical to be injected.

When power switched on to the device on April 11, control proceeds to S101, S102, S103, S106, and S110, and the dose for April 11 is corrected. In this correction, the current dose is calculated as 1.30 mg by using the formula: (planned dose+maximum correction amount), the correction calculation is ended, and the pharmaceutical injection schedule is reset as shown in FIG. 44. Similarly, correction is also performed in injection on April 12, and the dose is set to 1.30 mg. In S120, since the last injection was not skipped, control proceeds to S118, and the display in FIG. 16f or similar to that in FIG. 16f is given. For example, prior to the pharmaceutical injection on April 11, the initial planned cumulative dose is 8.00 mg and the actual cumulative dose is 7.30 mg, so in this case a display of "Ready for injection," "Dose still short," "Dose short by: 0.70 mg," "Extra 0.30 mg will be injected," and "Current dose: 1.30 mg" is given.

Meanwhile, on April 13, in S202, since the initial planned cumulative dose up to the last time is 11.00 mg, and the actual cumulative dose is 10.90, the differential dose is 0.10 mg, which is less than the maximum correction amount (0.30 mg), so control proceeds to S207, and the dose for the correction day is found to be 1.10 mg by using the formula: (planned dose+differential dose).

By thus correcting the dose every injection day and using that correction amount to reset the pharmaceutical injection schedule, the patient need not visit a physician, so the device is more convenient to use.

(A-2)

Figure 45:
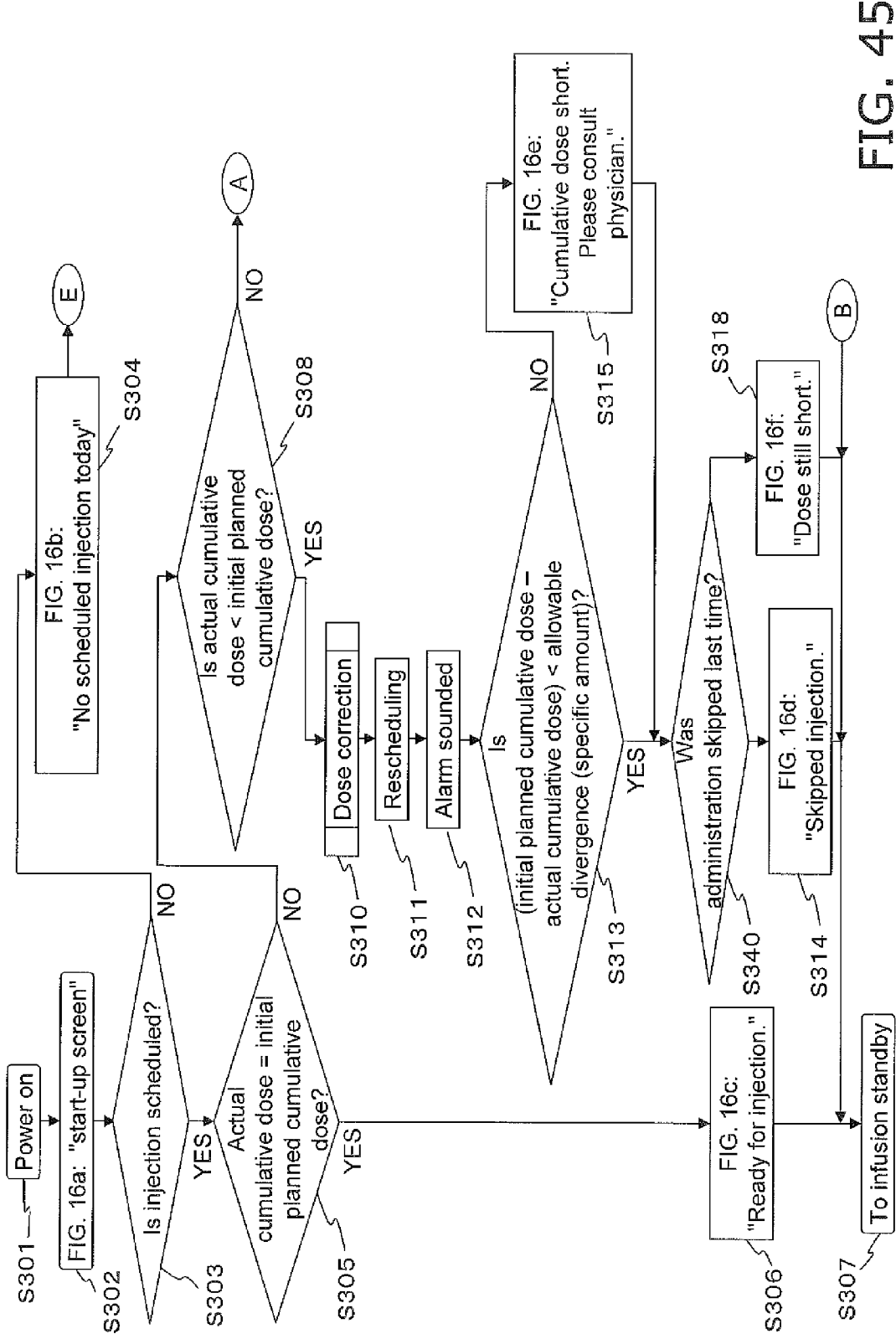
FIG. 45 is a flowchart of the operation of the pharmaceutical injection device pertaining to a modification example of Embodiment 2 of the present invention.

What is described in section A-1 above can be applied not only to Embodiment 1, but also to Embodiment 2. FIGS. 45, 46, 47, and 48 are modification examples of FIGS. 18, 20, 21, and 22 in Embodiment 2, and show the control flow of the pharmaceutical injection preparatory operation in correcting only the pharmaceutical dose for a given day. In FIG. 45, unlike S309 in FIG. 18, the step (S340) of determining whether the last injection was skipped is provided between S313/S315 and S314. Also, in FIG. 45, the steps S316 and S317 are not provided. Consequently, whether the injection was skipped last time is determined after performing the dose correction in S310, so correction can be performed on every pharmaceutical injection day.

Figure 46:
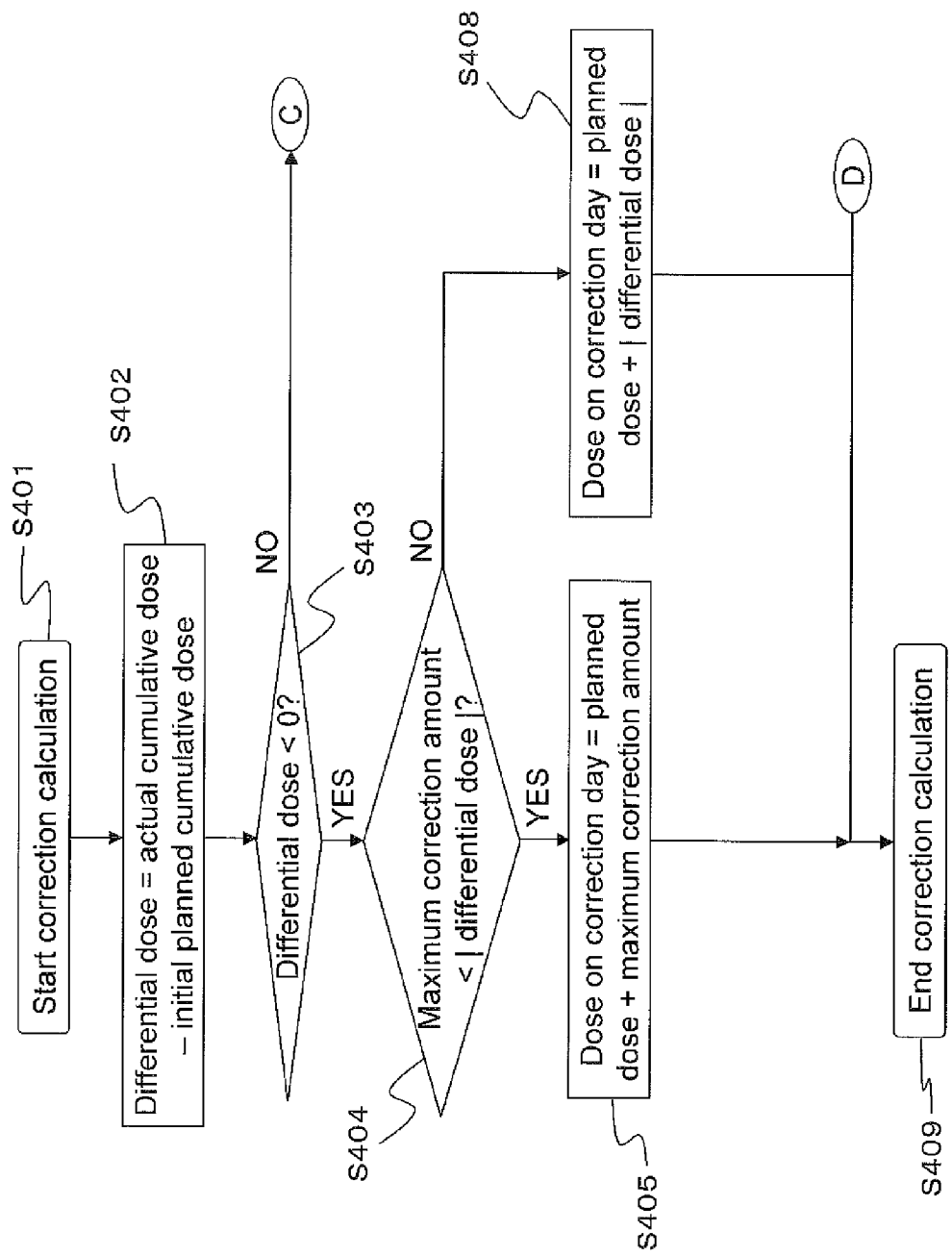
FIG. 46 is a flowchart of the operation of the pharmaceutical injection device pertaining to a modification example of Embodiment 2 of the present invention.

In FIG. 46, unlike in FIG. 20, the steps S406 and S407 are not provided, and after S405 control proceeds to S409. In Embodiment 2, the correction amount is calculated for all the injection days on which the dose needs to be corrected, but with the control in FIG. 46, only the pharmaceutical injection days are corrected.

Figure 47:
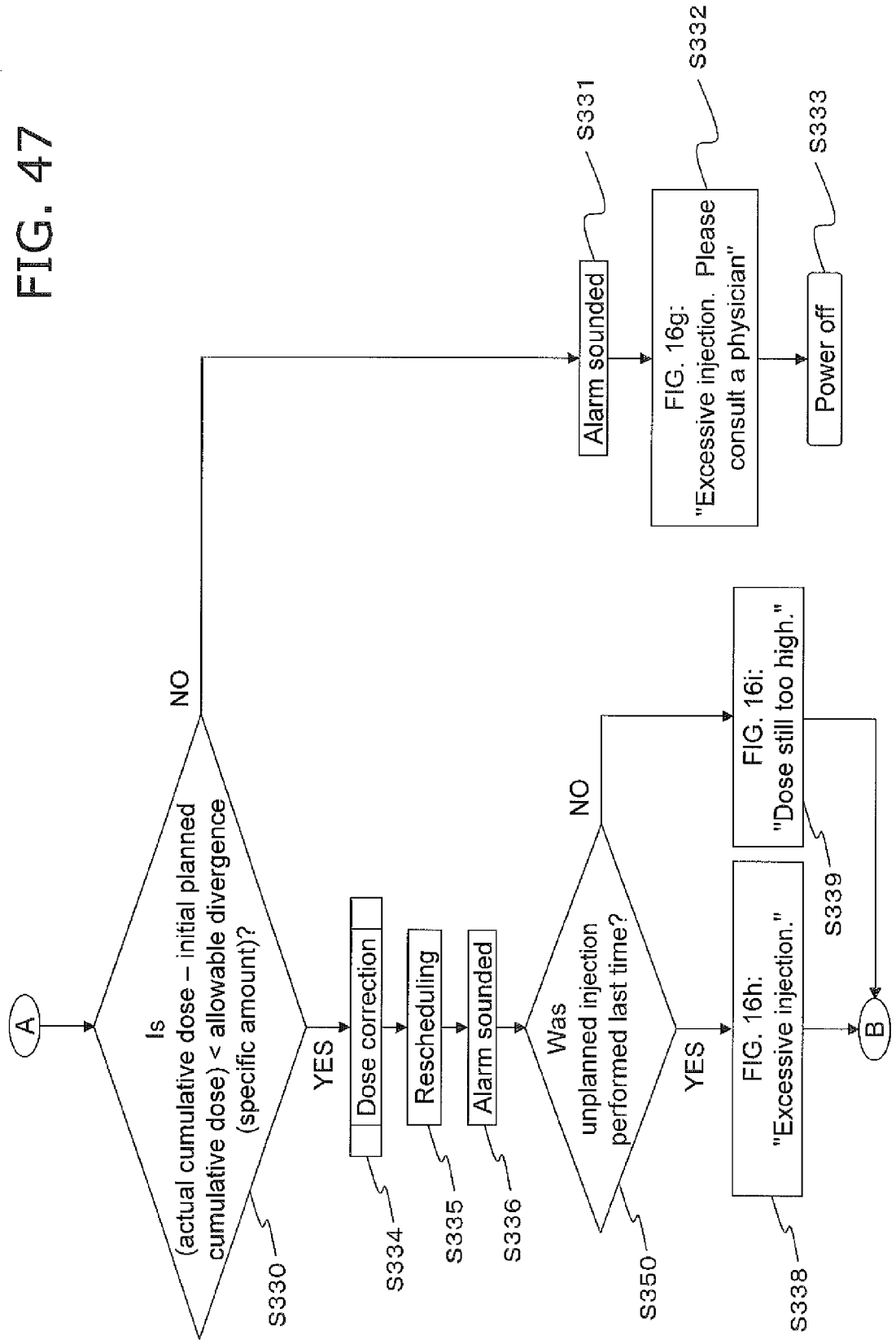
FIG. 47 is a flowchart of the operation of the pharmaceutical injection device pertaining to a modification example of Embodiment 2 of the present invention.

In FIG. 47, a step of determining whether or not unplanned injection was performed the last time in S334 in FIG. 21 is provided as S350 between S336 and S338. Consequently, it is determined (S350) whether or not unplanned injection was performed the last time after performing dose correction in S334, so correction is performed every pharmaceutical injection day.

Figure 48:
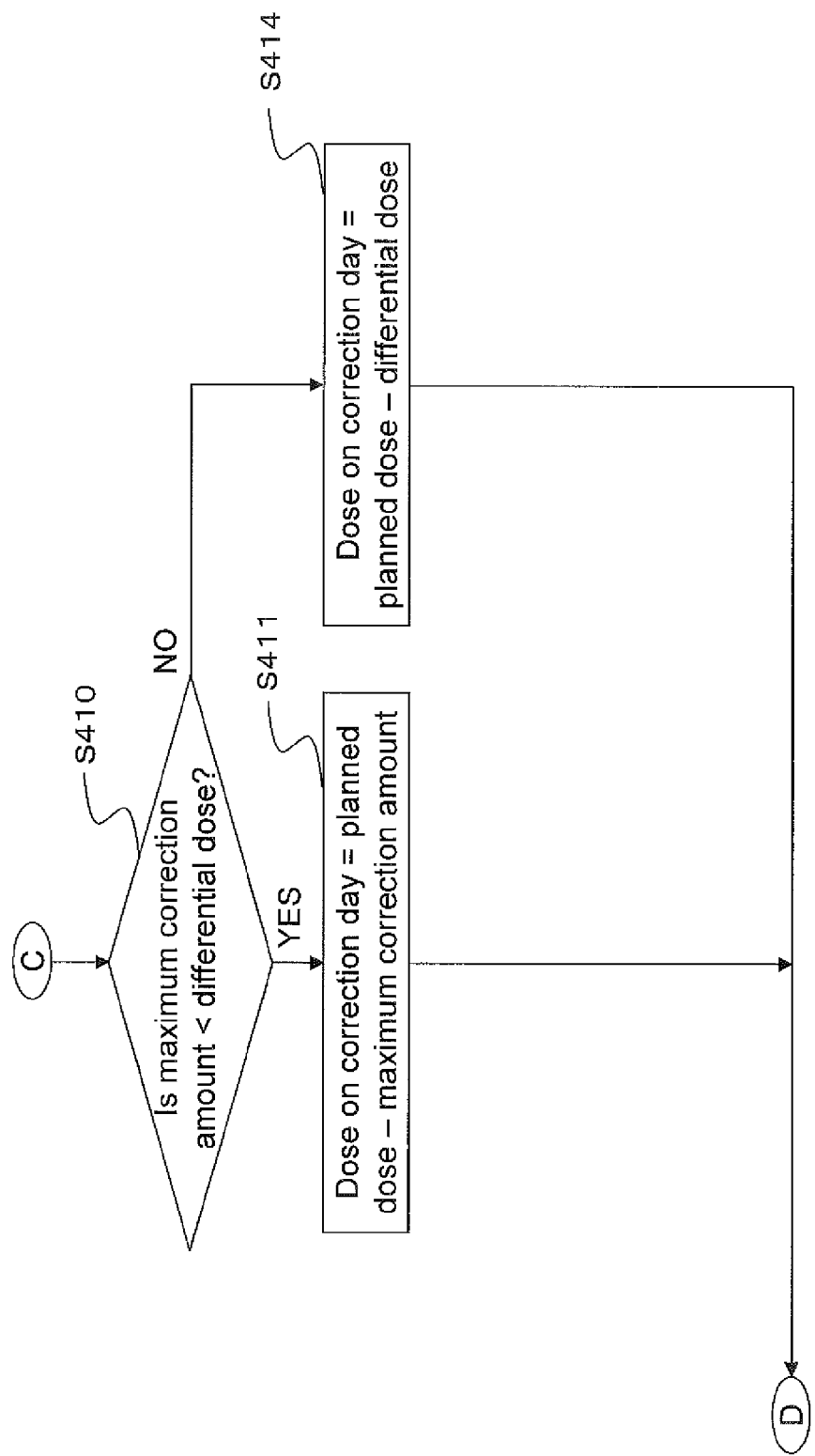
FIG. 48 is a flowchart of the operation of the pharmaceutical injection device pertaining to a modification example of Embodiment 2 of the present invention.

In FIG. 48, unlike FIG. 22, the steps S412 and S413 are not provided, and after S411 control proceeds to S409 (see FIG. 46). In Embodiment 2, the correction amount is calculated for all the injection days on which the dose needs to be corrected, but in the control in FIG. 46, only correction of the pharmaceutical injection days is performed.

The above control flow allows the dose to be corrected on every injection day.

(A-3)

Figure 49:
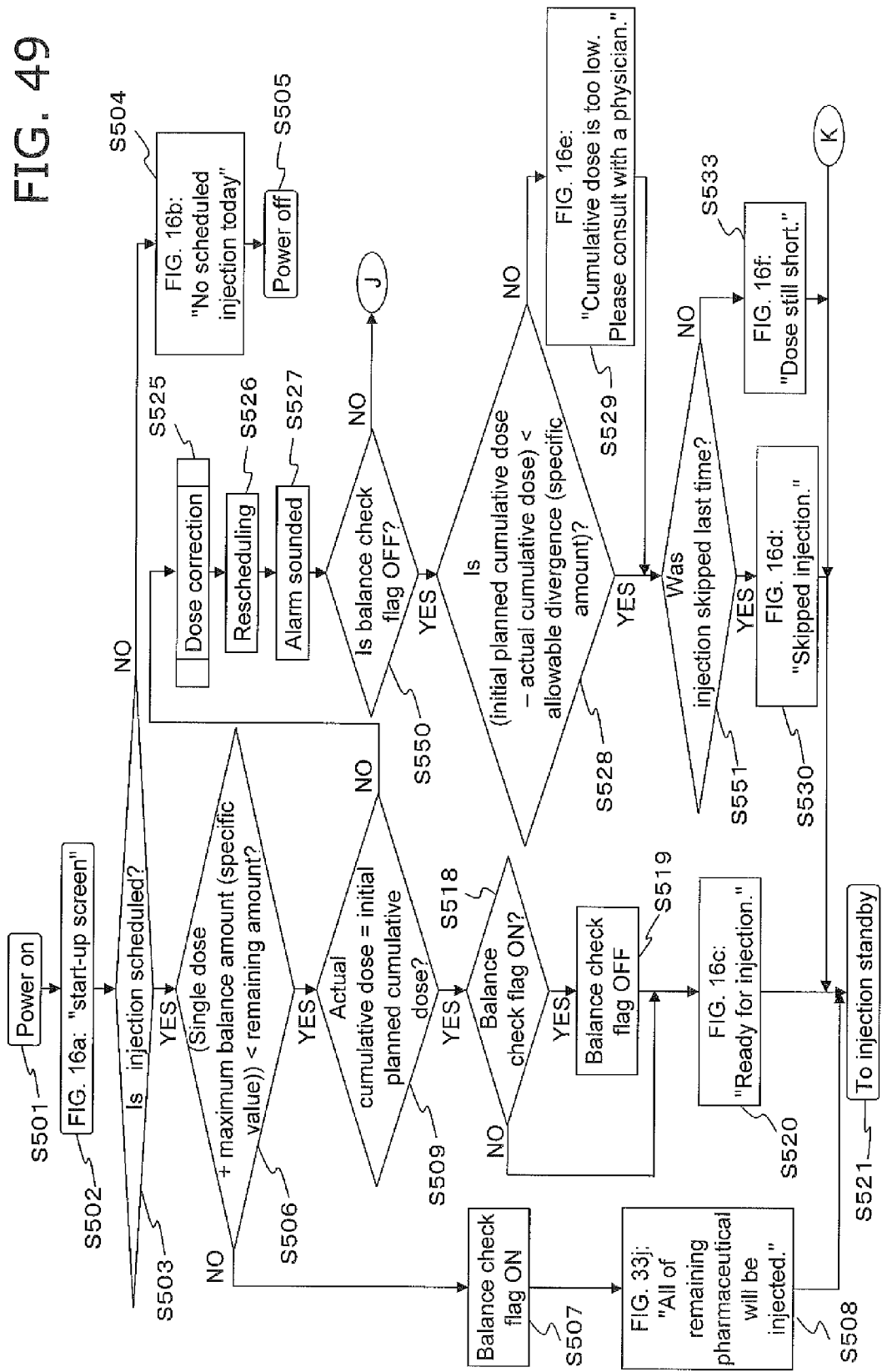
FIG. 49 is a flowchart of the operation of the pharmaceutical injection device pertaining to a modification example of Embodiment 3 of the present invention.

FIGS. 49 and 50 show the control flow when control for correcting only the pharmaceutical injection dose on a given day is applied to Embodiment 3.

For instance, we will give an example of the pharmaceutical injection schedule and injection results shown in FIG. 35. As discussed above, in injection on April 8, the balance check flag is in its ON state. In pharmaceutical injection on April 10, control proceeds to S501, S502, S503, S506, S509, and S525, and in S525 the dose is corrected. In S525, the correction operation shown in FIG. 42 is performed, and the correction amount is calculated for just the pharmaceutical injection days, as discussed above in section A-1. Then, in S550, since the balance check flag is not OFF, control proceeds to S516, the actual cumulative dose is compared with the initial planned cumulative dose, and the display in FIG. 33k (S517) or the display in FIG. 33l (S522) is given, according to the comparison result.

Meanwhile, if no adjustment injection is performed, and an injection is skipped, then in the next injection the correction amount for that time is calculated in S525, but since the balance check flag is OFF, control proceeds from S550 to S528. Then, in S528, if the difference between the initial planned cumulative dose and the actual cumulative dose is at or above the allowable divergence, a message recommending consultation with a physician is displayed (S529), and control proceeds to S551. In S551 it is determined whether or not injection was skipped the last time, and if injection was skipped the last time, the display in FIG. 16d is given (S530), but if injection was not skipped the last time, the display in FIG. 16f or one similar to that in FIG. 16f is given (S533).

(B)

In Embodiments 1 to 3 above, when pharmaceutical injection was skipped during the period of corrected pharmaceutical injection (the period when the pharmaceutical injection dose is different from that set by the physician at the outset), when the injection was unplanned, or when adjustment injection occurred, the pharmaceutical injection schedule was further reset, and the reset pharmaceutical injection schedule was updated to a pharmaceutical injection schedule that was further reset, but both may be stored in the memory 46.

(C)

In the above embodiments, the pharmaceutical injection schedule set by the physician at the outset, and the pharmaceutical injection schedule reset by the pharmaceutical injection device were stored in the same memory 46, but may instead be stored in separate memories.

(D)

Some or all of the resetting steps in the method for controlling the pharmaceutical injection device in the above embodiments may be realized by using a program, for example. Also, some or all of the various steps, processing, and so forth may be carried out by a central processing unit (CPU) of a computer. The above-mentioned programs may operate in conjunction with a computer.

As a utilization mode for the above-mentioned program, it may be recorded to a ROM or other such recording medium that can be read by a computer, for example. As another utilization mode for the program, it may be transmitted over the Internet or another such transmission medium, or through light, radio waves, or another such transmission medium, and read by a computer. For example, the pharmaceutical injection device in the above embodiments may be connected by USB or the like to a computer, and a program for carrying out the above-mentioned information reading method may be transmitted over the Internet. This computer is not limited to a CPU or other such hardware, and may instead be firmware or an OS. Also, some or all of the various steps, processing, and so forth of the information reading method of the embodiments may be realized with hardware, or with software. Furthermore, a mixture of software and hardware may be used.

INDUSTRIAL APPLICABILITY

As discussed above, with the pharmaceutical injection device of the present invention, even if the injection of a pharmaceutical is skipped, for example, this device itself will reset the future pharmaceutical injection schedule, and as a result there is no need for the user to visit a physician to have the schedule reset, and this makes the device more convenient to use. Therefore, the present invention is expected to find wide application in the field of pharmaceutical injection devices and so forth in which a pharmaceutical mixing operation is required.

REFERENCE SIGNS LIST 1 injection needle insertion and retraction opening
2 main body case 3 pharmaceutical syringe mounting component
4 pharmaceutical syringe
5 piston
6 drive mechanism
7 controller
7a substrate
8 orientation sensor
9 bolt
10 piston drive motor
11 female threads
12 needle insertion and retraction drive motor
13 bolt
14 injection needle cylinder
16 distal end gasket
17 push-in gasket
18 separation gasket
19 solid pharmaceutical liquid pharmaceutical
21 bypass
22 housing
23 distal end cap
24 window syringe cover
26 encoder
27 control rod
28 distal end cap detector switch
29 control rod
30 syringe cover detector switch
31 power button
32 mix button
33 pharmaceutical injection button
34 end button
35 display component
36 rechargeable battery
37 central processing unit
38 ROM
39 orientation detecting section
39a orientation determination component
40 piston movement distance sensor
41 motor rotation controller
42 motor drive circuit
43 over-current detection circuit
44 buzzer
45 vibrator
46 memory

The invention claimed is:

1. A pharmaceutical injection device, comprising:
a main body case that has an opening through which an injection needle is inserted and retracted;
a pharmaceutical syringe mounting component that is provided inside the main body case and onto which a pharmaceutical syringe is mounted;
a piston that is provided movably with respect to the pharmaceutical syringe mounted onto the pharmaceutical syringe mounting component;
a drive mechanism that drives the piston;
a display component that displays information related to the injection of a pharmaceutical;
a memory that is provided inside the main body case and stores a preset pharmaceutical injection schedule to use up all of the pharmaceutical, the preset pharmaceutical injection schedule being set beforehand to divide a pharmaceutical into a plurality of injections; and
a controller that is electrically connected to the drive mechanism, the display component, and the memory,
wherein the controller resets a current or future pharmaceutical dose automatically to allocate a differential dose to a current or future pharmaceutical dose so as not to exceed a maximum correction amount when, in an injection of the pharmaceutical, the controller determines there is a difference by comparing a planned cumulative pharmaceutical dose, which is a planned cumulative amount of pharmaceutical injected up to a last time on the basis of the preset pharmaceutical injection schedule stored in the memory, with an actual cumulative pharmaceutical dose, which is a cumulative amount of pharmaceutical actually injected up to the last time, and when the absolute value of the differential dose is at or under an allowable divergence.

2. The pharmaceutical injection device according to claim 1,
wherein when the controller determines that the actual cumulative pharmaceutical dose is short of the planned cumulative amount of pharmaceutical dose, the controller resets a current or future pharmaceutical dose to a dose greater than a planned amount of the pharmaceutical to be injected on the basis of the preset pharmaceutical injection schedule so as to compensate the shortage until the differential dose is at or under the maximum correction amount, or
wherein when the controller determines the actual cumulative pharmaceutical dose is in excess of the planned cumulative amount of pharmaceutical dose, the controller resets a current or future pharmaceutical dose to a dose less than a planned amount of pharmaceutical to be injected on the basis of the preset pharmaceutical injection schedule so as to reduce the excess amount until the differential dose is at or under the maximum correction amount.

3. The pharmaceutical injection device according to claim 2, wherein the controller stores the reset future pharmaceutical injection schedule in the memory, and holds the preset pharmaceutical injection schedule.

4. The pharmaceutical injection device according to claim 3, wherein, when the reset future pharmaceutical injection schedule has been further reset, the controller updates the reset pharmaceutical injection schedule stored in the memory to the further reset pharmaceutical injection schedule.

5. The pharmaceutical injection device according to claim 2, wherein the controller causes the display component to display the current planned pharmaceutical dose that is planned on the basis of the reset future pharmaceutical injection schedule.

6. The pharmaceutical injection device according to claim 5, wherein the controller causes the display component to display whether the actual pharmaceutical dose produced by comparing the cumulative planned pharmaceutical dose up to the last time with the actual pharmaceutical dose up to the last time is too high or too low.

7. The pharmaceutical injection device according to claim 6, wherein the controller causes the display component to display the excess amount or the deficient amount of the actual cumulative pharmaceutical dose produced by comparing the cumulative planned pharmaceutical dose up to the last time with the actual cumulative pharmaceutical dose up to the last time.

8. The pharmaceutical injection device according to claim 7, wherein the controller causes the display component to display a reason why the actual cumulative pharmaceutical dose produced by comparing the cumulative planned pharmaceutical dose up to the last time with the actual cumulative pharmaceutical dose up to the last time is too high or too low.

9. The pharmaceutical injection device according to claim 6, wherein the controller causes the display component to display a message prompting the user to consult a physician when the excess amount or the deficient amount of the actual cumulative pharmaceutical dose produced by comparing the cumulative planned pharmaceutical dose up to the last time with the actual cumulative pharmaceutical dose up to the last time has exceeded the allowable divergence.

10. The pharmaceutical injection device according to claim 1, wherein the pharmaceutical is a growth hormone.

11. A method for controlling a pharmaceutical injection device comprising a main body case that has an opening through which an injection needle is inserted and retracted; a pharmaceutical syringe mounting component that is provided inside the main body case and onto which a pharmaceutical syringe is mounted; a piston that is provided movably with respect to the pharmaceutical syringe mounted onto the pharmaceutical syringe mounting component; a drive mechanism that drives the piston; a display component that displays information related to the injection of a pharmaceutical; and a memory that is provided inside the main body case and stores a preset pharmaceutical injection schedule being set beforehand to divide a pharmaceutical into a plurality of injections to use up all of the pharmaceutical;

wherein said method includes a resetting step of resetting a current or future pharmaceutical injection schedule automatically to allocate a differential dose to a current or future pharmaceutical dose so as not to exceed a maximum correction amount when there is a difference by comparing a cumulative planned pharmaceutical dose, which is a planned cumulative amount of pharmaceutical injected up to a last time on the basis of the preset pharmaceutical injection schedule stored in the memory, and an actual cumulative pharmaceutical dose, which is a cumulative amount of pharmaceutical actually injected up to the last time, and when the absolute value of the differential dose is at or under an allowable divergence.

* * * * *